United States Patent
Phan et al.

(10) Patent No.: US 12,129,302 B2
(45) Date of Patent: Oct. 29, 2024

(54) ANTI-CD-25 ANTIBODY

(71) Applicant: iBio, Inc., Bryan, TX (US)

(72) Inventors: Dillon Phan, La Jolla, CA (US); Martin Brenner, Bryan, TX (US); Brian Berquist, Bryan, TX (US); Peter Kipp, Bryan, TX (US); Tam Phuong, San Diego, CA (US); Kevin Babilonia, Bryan, TX (US); Tom Hsu, Chino, CA (US); Lufei Hu, Escondido, CA (US); James Talmage Taylor, Jr., College Station, TX (US); Cory Schwartz, San Diego, CA (US)

(73) Assignee: iBio, Inc., Bryan, TX (US)

( * ) Notice: Subject to any disclaimer, the term of this patent is extended or adjusted under 35 U.S.C. 154(b) by 0 days.

(21) Appl. No.: 17/821,295

(22) Filed: Aug. 22, 2022

(65) Prior Publication Data

US 2023/0159646 A1 May 25, 2023

Related U.S. Application Data

(60) Provisional application No. 63/339,182, filed on May 6, 2022, provisional application No. 63/312,213, filed on Feb. 21, 2022, provisional application No. 63/237,100, filed on Aug. 25, 2021.

(51) Int. Cl.
*C07K 16/28* (2006.01)
*A61P 35/00* (2006.01)

(52) U.S. Cl.
CPC .......... *C07K 16/2866* (2013.01); *A61P 35/00* (2018.01); *C07K 2317/24* (2013.01); *C07K 2317/567* (2013.01); *C07K 2317/732* (2013.01); *C07K 2317/92* (2013.01)

(58) Field of Classification Search
None
See application file for complete search history.

(56) References Cited

U.S. PATENT DOCUMENTS

| | | |
|---|---|---|
| 3,832,253 A | 8/1974 | DiPalma et al. |
| 3,854,480 A | 12/1974 | Zaffaroni |
| 4,452,775 A | 6/1984 | Kent |
| 4,522,752 A | 6/1985 | Sisto et al. |
| 4,667,014 A | 5/1987 | Nestor, Jr. et al. |
| 4,683,195 A | 7/1987 | Mullis et al. |
| 4,748,034 A | 5/1988 | de Rham |
| 5,075,109 A | 12/1991 | Tice et al. |
| 5,091,309 A | 2/1992 | Schlesinger et al. |
| 5,093,258 A | 3/1992 | Cohen et al. |
| 5,217,879 A | 6/1993 | Huang et al. |
| 5,225,538 A | 7/1993 | Capon et al. |
| 5,239,660 A | 8/1993 | Ooi |
| 5,707,632 A | 1/1998 | Williams et al. |
| 5,726,044 A | 3/1998 | Lo et al. |
| 5,925,351 A | 7/1999 | Browning et al. |
| 6,015,692 A | 1/2000 | Gyuris et al. |
| 6,165,460 A | 12/2000 | Schlom et al. |
| 6,218,371 B1 | 4/2001 | Krieg et al. |
| 6,406,697 B1 | 6/2002 | Capon et al. |
| 6,551,592 B2 | 4/2003 | Lindhofer et al. |
| 6,656,728 B1 | 12/2003 | Kavanaugh et al. |
| 6,998,252 B1 | 2/2006 | Moss et al. |
| 7,491,509 B2 | 2/2009 | Fedorkin et al. |
| 8,962,278 B2 * | 2/2015 | Yusibov .................... A61P 9/00 435/69.6 |
| 2009/0297529 A1 | 12/2009 | Li et al. |
| 2012/0148592 A1 | 6/2012 | Imai et al. |
| 2014/0294836 A1 * | 10/2014 | Chu .................... C07K 16/2812 435/328 |
| 2017/0029530 A1 | 2/2017 | Saunders et al. |
| 2021/0107985 A1 | 4/2021 | Schuurman et al. |

FOREIGN PATENT DOCUMENTS

| | | | |
|---|---|---|---|
| TW | 201938588 A | 1/2019 | |
| WO | 0001720 A2 | 1/2000 | |
| WO | 20000001720 | 1/2000 | |
| WO | 0046350 A1 | 8/2000 | |
| WO | 2004004798 A2 | 1/2004 | |
| WO | 2020142659 A2 | 7/2020 | |
| WO | WO-2021161287 A2 * | 8/2021 | ........... A61K 39/395 |
| WO | WO-2023025249 A1 * | 3/2023 | |

OTHER PUBLICATIONS

Rabia et al. 2018, J Biochem Eng, vol. 137: 365-374 (Year: 2018).*
Scott et al., 2012, Nat Rev, vol. 12 278-287 (Year: 2012).*
Chan et al., 2010 Nat Rev, vol. 10: 301-316 (Year: 2010).*
Janeway, The generation of diversity in immunoglobulins. 2001 (Year: 2001).*
Huss et al., 2016, Immunol vol. 148: 276-286 (Year: 2016).*
Chadd, et al. "Therapeutic antibody expression technology" Current Opinion in Biotechnology 2001, 12:188-194.
Frenzel, et al. "Expressin of recombinant antibodies" Frontiers in Immunology, published Jul. 29, 2013, doi: 10.3389/fimmu.2013.00217.
Gleba, et al. "Viral vectors for the expression of proteins in plants" Current Opinion in Biotechnology 2007, 18:134-141, available online Mar. 23, 2007, DOI 10.1016/j.copbio.2007.03.002.
Taiwan Intellectual Property Office, Examination Report for Taiwan Patent Appl. No. 11132095 dated Dec. 20, 2023 with translation, 19 pp.
United States Patent & Trademark Office (ISA), International Search Report & Written Opinion for PCT/US2022/075266 dated Jan. 20, 2023, 25 pp.

* cited by examiner

*Primary Examiner* — Daniel E Kolker
*Assistant Examiner* — Maureen Varina Driscoll
(74) *Attorney, Agent, or Firm* — Edwin S. Flores; Daniel J. Chalker; Chalker Flores, LLP

(57) ABSTRACT

Materials and methods for using polypeptides containing fragments and variants of the antibody(ies) or portion(s) thereof that bind CD25 to treat cancer alone or in combination with other anti-neoplastic agents.

22 Claims, 36 Drawing Sheets

Specification includes a Sequence Listing.

| Theoretical Average MW | Observed Average MW | Error (Da) | Modifications | Protein Name |
|---|---|---|---|---|
| 23554.9 | 23555.0 | 0.14 | | hD11 (c105) Light chain |
| 49772.4 | 49773.5 | 1.12 | G0 - 1;Gln->pyro-Glu - 1;Protein Terminal Lys-loss - 1 | hD11 (c105) Heavy chain |
| 49900.6 | 49901.3 | 0.75 | G0 - 1;Gln->pyro-Glu - 1 | hD11 (C105) Heavy chain |

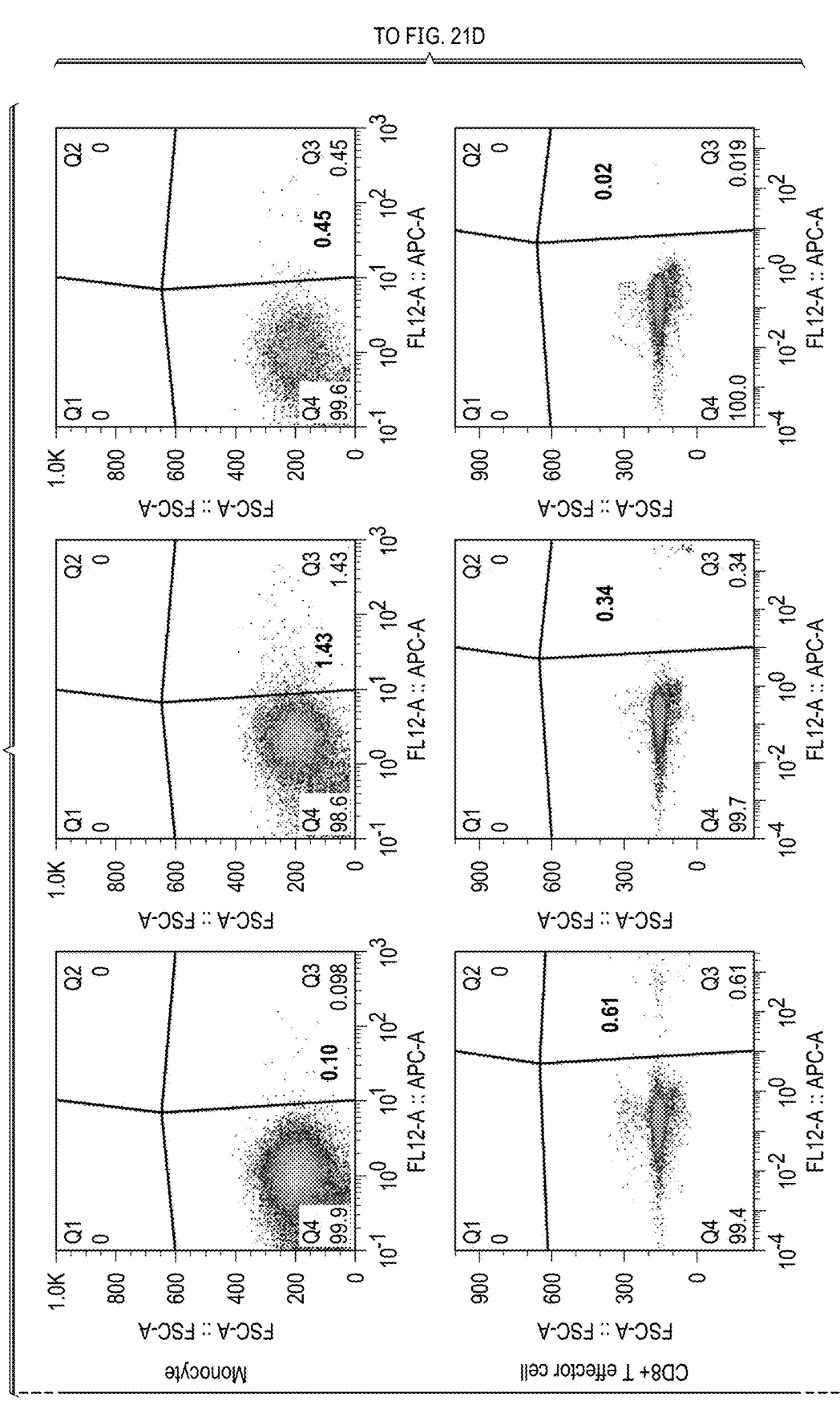

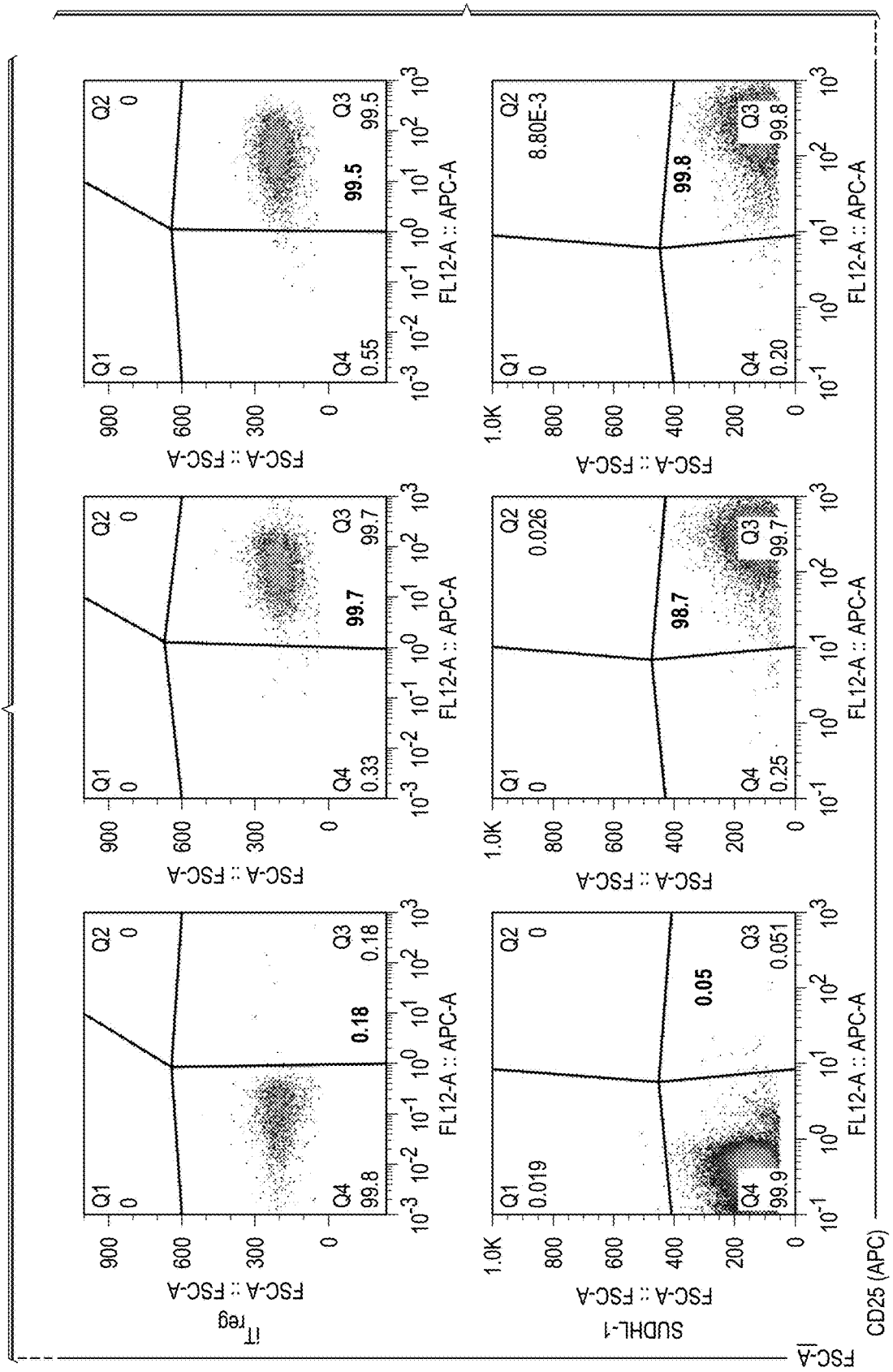

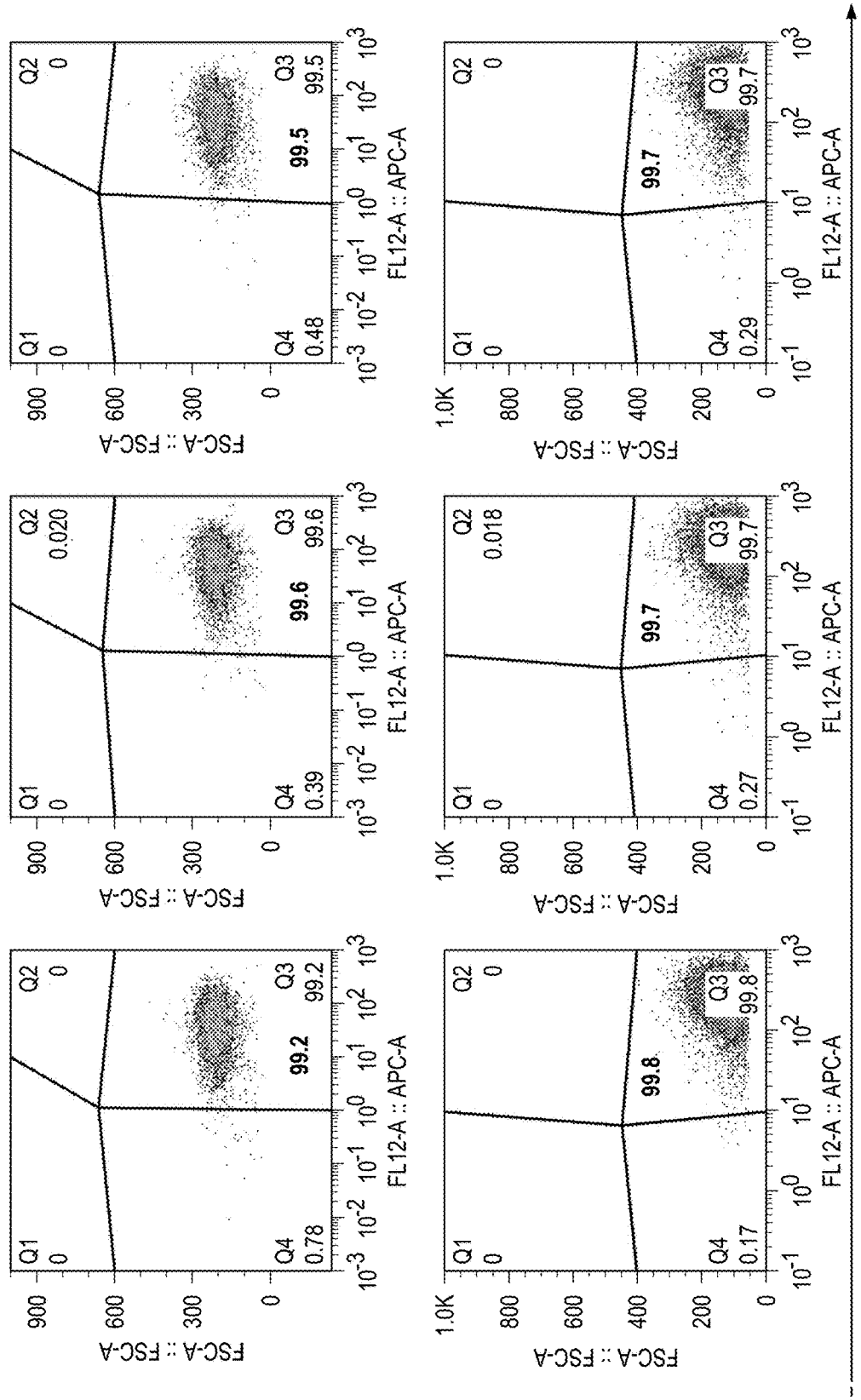

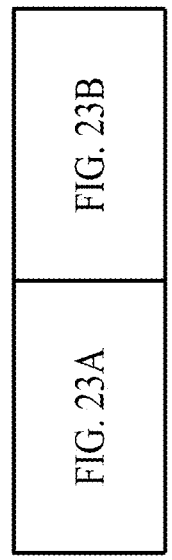

SEQUENCE LISTING

```
Sequence total quantity: 12
SEQ ID NO: 1         moltype = AA  length = 471
FEATURE              Location/Qualifiers
REGION               1..471
                     note = Synthetic: ExtSP-hD11 heavy Chain (HC)
source               1..471
                     mol_type = protein
```

```
                        organism = synthetic construct
SEQUENCE: 1
MGKMASLFAT FLVVLVSLSL ASESSAQVQL VQSGAEVKKP GASLKISCKG SGYTFTDYAM    60
HWVRQAPGQG LEWIGVISTY SGDAIYAQKF QGRATMTVDT STSTAYLELS SLRSEDTAVY   120
YCARGVTFDY WGQGTTVTVS SASTKGPSVF PLAPSSKSTS GGTAALGCLV KDYFPEPVTV   180
SWNSGALTSG VHTFPAVLQS SGLYSLSSVV TVPSSSLGTQ TYICNVNHKP SNTKVDKRVE   240
PKSCDKTHTC PPCPAPELLG GPSVFLFPPK PKDTLMISRT PEVTCVVVDV SHEDPEVKFN   300
WYVDGVEVHN AKTKPREEQY NSTYRVVSVL TVLHQDWLNG KEYKCKVSNK ALPAPIEKTI   360
SKAKGQPREP QVYTLPPSRE EMTKNQVSLT CLVKGFYPSD IAVEWESNGQ PENNYKTTPP   420
VLDSDGSFFL YSKLTVDKSR WQQGNVFSCS VMHEALHNHY TQKSLSLSPG K            471

SEQ ID NO: 2            moltype = DNA  length = 1416
FEATURE                 Location/Qualifiers
misc_feature            1..1416
                        note = Synthetic: ExtSP-hD11 HC, Codon optimized version 1
source                  1..1416
                        mol_type = other DNA
                        organism = synthetic construct
SEQUENCE: 2
atgggaaaaa tggcttctct ttttgctact tccttgttg tgttggttag tctttctcta    60
gctagtgaga gtagtgctca agttcagctg gtgcagagtg gtgctgaggt gaagaaacct   120
ggtgcctcat tgaaaatttc gtgcaaaggg agcgggtaca ctttcaccga ctacgcaatg   180
cattgggtaa ggcaagcacc aggtcaaggc ttagaatgga ttggagtcat cagcacctac   240
tctggtgatg ccatatatgc tcaaaagttt cagggaagag cgacaatgac tgttgataca   300
tcaacttcta cagcatatct tgagttgtca tccctccgta gtgaagatac tgctgtttat   360
tattgtgcta gaggcgtaac atttgattat tgggacaaga gaacaactgt cacggtttct   420
tccgctagca ccaaaggtcc ttcagtcttc ccacttgcgc caagttccaa aagcacttct   480
ggcggcactg ctgcgcttgg ctgtctcgta aaagactatt ttccagagcc agtgacagtc   540
agttggaata gcggtgctct cacaagtggc gttcatacat ttcctgctgt tctgcaatct   600
tctggtttat actctttatc gagcgtagta acagttcctt catcatcact tgggactcaa   660
acttatatat gtaatgtcaa ccacaagccg tccaacacta agtagacaa gagggttgaa   720
ccaaaatctt gtgataagac acacacttgc cctccttgtc ctgcaccaga gctcttgggt   780
ggtccatcag tgtttctatt cccgccaaag ccaaaggata cactcatgat atcacgcacc   840
cctgaggtta cttgtgttgt agttgatgtt agtcatgaag atccggaagt gaagtttaat   900
tggtatgttg atggagtgga agttcacaat gcaaaaacca agcctcgtga agagcagtac   960
aattcaacat atcgtgttgt ttcagttcta acagtcctc atcaagattg gttgaatgga  1020
aaagaatata aatgcaaggt gagcaacaaa gcacttccag ctccaattga aaaacaatt   1080
agcaaggcaa agggacaacc aagagaacct caagtttaca cgcttcctcc ctcccgagaa  1140
gaaatgacaa agaatcaggt cagtctgact tgcttggtta aagggtttta ccctctgat   1200
attgcagtgg aatgggaatc taatggtcag cctgaaaata actacaagac caccccccca  1260
gtacttgatt cagatggttc tttcttttta tattctaaat taactgtgga taaatcaaga  1320
tggcaacaag ggaatgtttt cagttgctcc gtgatgcatg aggccttaca taatcattat  1380
actcagaagt cccttagtct gtcaccgggt aagtga                            1416

SEQ ID NO: 3            moltype = DNA  length = 1416
FEATURE                 Location/Qualifiers
misc_feature            1..1416
                        note = Synthetic: ExtSP-hD11 HC, Codon optimized version 2
source                  1..1416
                        mol_type = other DNA
                        organism = synthetic construct
SEQUENCE: 3
atgggaaaaa tggcttctct ttttgctact tccttgttg tgttggttag tctttctcta    60
gctagtgaga gtagtgctca agttcagctt gtacagtctg gggctgaggt gaagaaacca   120
ggggcatcct taaaaatttc ttgcaaagga tcaggctaca cttttcactga ttatgcaatg   180
cattgggtta ggcaagctcc tggtcaaggt ctcgaatgga ttggagtcat ctcaacctac   240
tctggtgatg caatatatgc tcaaaagttt caaggaagag cgacaatgac tgttgacacc   300
tcaacagta cagcctattt ggagctgagc agcctaagaa gtgaagatac tgccgtttat   360
tattgtgctc gtggcgtaac atttgattac tggggtcagg gaactacggt gacagtctcg   420
tccgctagca ccaaaggtcc ttcagtcttc ccacttgcgc caagttccaa aagcacttct   480
ggcggcactg ctgcgcttgg ctgtctcgta aaagactatt ttccagagcc agtgacagtc   540
agttggaata gcggtgctct cacaagtggc gttcatacat ttcctgctgt tctgcaatct   600
tctggtttat actctttatc gagcgtagta acagttcctt catcatcact tgggactcaa   660
acttatatat gtaatgtcaa ccacaagccg tccaacacta agtagacaa gagggttgaa   720
ccaaaatctt gtgataagac acacacttgc cctccttgtc ctgcaccaga gctcttgggt   780
ggtccatcag tgtttctatt cccgccaaag ccaaaggata cactcatgat atcacgcacc   840
cctgaggtta cttgtgttgt agttgatgtt agtcatgaag atccggaagt gaagtttaat   900
tggtatgttg atggagtgga agttcacaat gcaaaaacca agcctcgtga agagcagtac   960
aattcaacat atcgtgttgt ttcagttcta acagtcctc atcaagattg gttgaatgga  1020
aaagaatata aatgcaaggt gagcaacaaa gcacttccag ctccaattga aaaacaatt   1080
agcaaggcaa agggacaacc aagagaacct caagtttaca cgcttcctcc ctcccgagaa  1140
gaaatgacaa agaatcaggt cagtctgact tgcttggtta aagggtttta ccctctgat   1200
attgcagtgg aatgggaatc taatggtcag cctgaaaata actacaagac caccccccca  1260
gtacttgatt cagatggttc tttcttttta tattctaaat taactgtgga taaatcaaga  1320
tggcaacaag ggaatgtttt cagttgctcc gtgatgcatg aggccttaca taatcattat  1380
actcagaagt cccttagtct gtcaccgggt aagtga                            1416

SEQ ID NO: 4            moltype = AA  length = 240
FEATURE                 Location/Qualifiers
```

| | | |
|---|---|---|
| REGION | 1..240 | |
| | note = Synthetic: ExtSP-hD11 Light Chain (LC) | |
| source | 1..240 | |
| | mol_type = protein | |
| | organism = synthetic construct | |

SEQUENCE: 4
```
MGKMASLFAT FLVVLVSLSL ASESSADIQM TQSPSSLSAS VGDRVTITCR ASQDISNYLE    60
WYQQKPGKAP KLLVYNAKTL AEGVPSRFSG SGSGTDFTLT ISSLQPEDFG TYYCQHHYDT   120
PYTFGQGTKL EIKRTVAAPS VFIFPPSDEQ LKSGTASVVC LLNNFYPREA KVQWKVDNAL   180
QSGNSQESVT EQDSKDSTYS LSSTLTLSKA DYEKHKVYAC EVTHQGLSSP VTKSFNRGEC   240
```

| | | |
|---|---|---|
| SEQ ID NO: 5 | moltype = DNA  length = 723 | |
| FEATURE | Location/Qualifiers | |
| misc_feature | 1..723 | |
| | note = Synthetic: ExtSP-hD11 Light Chain (LC), codon optimized version 1 | |
| source | 1..723 | |
| | mol_type = other DNA | |
| | organism = synthetic construct | |

SEQUENCE: 5
```
atgggaaaaa tggcttctct ttttgctact ttccttgttg tgttggttag tctttctcta    60
gctagtgaga gtagtgctga cattcaaatg acacagagtc catcaagcct cagtgcttct   120
gttggagacc gtgttacaat tacatgcagg gcctctcaag atatatccaa ctacttggaa   180
tggtatcaac agaaacccgg aaaagcacca aagcttttag tgtacaatgc taaaactctg   240
gcagagggtg taccttcaag attcagcggt tcaggcagtg gcactgattt cacactaacg   300
atctcttctc ttcagccgga agattttggg acttattatt gtcaacatca ctatgatacc   360
ccttacactt ttggtcaagg aaccaagttg agattaaga gaactgttgc tgctccttct   420
gtgttcattt tccaccatc tgatgaacaa ctgaagagcg gcacagcgtc agtcgtttgt   480
ttgttgaata atttttaccc tagagaggct aaagtacagt ggaaagttga taatgctctg   540
cagtctggaa attcccaaga atcagtaaca gagcaagatt caaaggattc cacctacagt   600
ctttcgtcta ctttaacatt gtctaaagca gactatgaaa agcacaaagt gtatgcttgt   660
gaagttactc atcaaggtct cagctcgccg gtgacaaaat cgttcaacag gggtgaatgt   720
tga                                                                 723
```

| | | |
|---|---|---|
| SEQ ID NO: 6 | moltype = DNA  length = 723 | |
| FEATURE | Location/Qualifiers | |
| misc_feature | 1..723 | |
| | note = Synthetic: ExtSP-hD11 Light Chain (LC) | |
| source | 1..723 | |
| | mol_type = other DNA | |
| | organism = synthetic construct | |

SEQUENCE: 6
```
atgggaaaaa tggcttctct ttttgctact ttccttgttg tgttggttag tctttctcta    60
gctagtgaga gtagtgctga cattcaaatg actcaatctc cgagcagctt atctgcctca   120
gtaggtgata gagtgacaat aacttgcagg gcatctcaag atatttcaaa ctacctggaa   180
tggtatcagc agaaaccagg gaaagctcca aagctccttg tttacaatgc aaagacattg   240
gctgagggtg ttccttcacg ttttctctgga agtgggtcgg gcaccgactt cacgctaacc   300
atcagttccc ttcagcctga agattttgga acttattatt gtcaacatca ctatgatact   360
ccctacacat ttggtcaagg aacaaagttg agattaaaa gaactgttgc tgctccttct   420
gtgttcattt tccaccatc tgatgaacaa ctgaagagcg gcacagcgtc agtcgtttgt   480
ttgttgaata atttttaccc tagagaggct aaagtacagt ggaaagttga taatgctctg   540
cagtctggaa attcccaaga atcagtaaca gagcaagatt caaaggattc cacctacagt   600
ctttcgtcta ctttaacatt gtctaaagca gactatgaaa agcacaaagt gtatgcttgt   660
gaagttactc atcaaggtct cagctcgccg gtgacaaaat cgttcaacag gggtgaatgt   720
tga                                                                 723
```

| | | |
|---|---|---|
| SEQ ID NO: 7 | moltype = DNA  length = 699 | |
| FEATURE | Location/Qualifiers | |
| misc_feature | 1..699 | |
| | note = Synthetic: Fc portion of human IgG1 which includes the hingeregion, and domains CH2 and CH3 | |
| source | 1..699 | |
| | mol_type = other DNA | |
| | organism = synthetic construct | |

SEQUENCE: 7
```
gagcccaaat cttgtgacaa aactcacaca tgcccaccgt gcccagcacc tgaactcctg    60
gggggaccgt cagtcttcct cttcccccca aaacccaagg acaccctcat gatctcccgg   120
acccctgagg tcacatgcgt ggtggtggac gtgagccacg aagaccctga ggtcaagttc   180
aactggtacg tggacggcgt ggaggtgcat aatgccaaga caaagccgcg ggaggagcag   240
tacaacagca cgtaccgtgt ggtcagcgtc ctcaccgtcc tgcaccagga ctggctgaat   300
ggcaaggagt acaagtgcaa ggtctccaac aaagccctcc cagcccccat cgagaaaacc   360
atctccaaag ccaaagggca gccccgagaa ccacaggtgt acaccctgcc cccatcccgg   420
gatgagctga ccaagaacca ggtcagcctg acctgcctgg tcaaaggctt ctatcccagc   480
gacatcgccg tggagtggga gagcaatggg cagccggaga acaactacaa gaccacgcct   540
cccgtgctgg actccgacgg ctccttcttc ctctacagca agctcaccgt ggacaagagc   600
aggtggcagc aggggaacgt cttctcatgc tccgtgatgc atgaggctct gcacaaccac   660
tacacgcaga agagcctctc cctgtctccg ggtaaatga                           699
```

| | | |
|---|---|---|
| SEQ ID NO: 8 | moltype = AA  length = 232 | |

```
FEATURE                     Location/Qualifiers
REGION                      1..232
                            note = Synthetic: Fc portion of human IgG1 which includes
                             the hingeregion, and domains CH2 and CH3
source                      1..232
                            mol_type = protein
                            organism = synthetic construct
SEQUENCE: 8
EPKSCDKTHT CPPCPAPELL GGPSVFLFPP KPKDTLMISR TPEVTCVVVD VSHEDPEVKF  60
NWYVDGVEVH NAKTKPREEQ YNSTYRVVSV LTVLHQDWLN GKEYKCKVSN KALPAPIEKT 120
ISKAKGQPRE PQVYTLPPSR DELTKNQVSL TCLVKGFYPS DIAVEWESNG QPENNYKTTP 180
PVLDSDGSFF LYSKLTVDKS RWQQGNVFSC SVMHEALHNH YTQKSLSLSP GK         232

SEQ ID NO: 9                moltype = AA  length = 471
FEATURE                     Location/Qualifiers
REGION                      1..471
                            note = Synthetic: Heavy_Chain_Amino_Acid
source                      1..471
                            mol_type = protein
                            organism = synthetic construct
SEQUENCE: 9
MGKMASLFAT FLVVLVSLSL ASESSAQVQL VQSGAEVKKP GASLKISCKG SGYTFTDYAM  60
HWVRQAPGQG LEWIGVISTY SGDAIYAQKF QGRATMTVDT STSTAYLELS SLRSEDTAVY 120
YCARGVTFDY WGQGTTVTVS SASTKGPSVF PLAPSSKSTS GGTAALGCLV KDYFPEPVTV 180
SWNSGALTSG VHTFPAVLQS SGLYSLSSVV TVPSSSLGTQ TYICNVNHKP SNTKVDKKVE 240
PKSCDKTHTC PPCPAPELLG GPSVFLFPPK PKDTLMISRT PEVTCVVVDV SHEDPEVKFN 300
WYVDGVEVHN AKTKPREEQY NSTYRVVSVL TVLHQDWLNG KEYKCKVSNK ALPAPIEKTI 360
SKAKGQPREP QVYTLPPSRE EMTKNQVSLT CLVKGFYPSD IAVEWESNGQ PENNYKTTPP 420
VLDSDGSFFL YSKLTVDKSR WQQGNVFSCS VMHEALHNHY TQKSLSLSPG K          471

SEQ ID NO: 10               moltype = DNA  length = 1416
FEATURE                     Location/Qualifiers
misc_feature                1..1416
                            note = Synthetic: Heavy_Chain_DNA
source                      1..1416
                            mol_type = other DNA
                            organism = synthetic construct
SEQUENCE: 10
atgggaaaaa tggcttctct ttttgctact ttccttgttg tgttggttag tctttctcta   60
gctagtgaga gtagtgctca agttcagctg gtgcagagtg gtgctgaggt gaagaaacct  120
ggtgcctcat tgaaaatttc gtgcaaaggg agcgggtaca ctttcaccga ctacgcaatg  180
cattgggtaa ggcaagcacc aggtcaaggc ttagaatgga ttggagtcat cagcacctac  240
tctggtgatg ccatatatgc tcaaaagttt cagggaagac gcacaatgac tgttgataca  300
tcaacttcta cagcatatct tgagttgtca tccctccgta gtgaagatac tgctgtttat  360
tattgtgcta gaggcgtaac atttgattat tggggacaag gaacaactgt cacggtttct  420
tccgctagca ccaaaggtcc ttcagtcttc ccacttgcgc caagttccaa aagcacttct  480
ggcggcactg ctgcgcttgg ctgtctcgta aaagacttt ttccagagcc agtgacagtc  540
agttggaata gcgtgctctc cacaagtggc gttcatacat ttcctgctgt tctgcaatct  600
tctggttttat actctttatc gagcgtagta acagttcctt catcatcact tgggactcaa  660
acttatatat gtaatgtcaa ccacaagccg tccaacacta agtagacaa gaaggttgaa  720
ccaaaatctt gtgataagac acacacttgc cctccttgtc ctgcaccaga gctcttgggt  780
ggtccatcag tgtttctatt cccgccaaag ccaaaggata cactcatgat atcacgcacc  840
cctgaggtta cttgtgttgt agttgatgtt agtcatgaag atccggaagt gaagtttaat  900
tggtatgttg atggagtgga agttcacaat gcaaaaacca gcctcgtga agagcagtac  960
aattcaacat atcgtgtcgt ttcagttcta acagtccttc atcaagattg gttgaatgga 1020
aaagaatata aatgcaaggt gagcaacaaa gcacttccag ctccaattga gaaaacaatt 1080
agcaaggcaa agggacaacc aagagaacct caagtttaca cgcttcctcc ctcccgagaa 1140
gaaatgacaa agaatcaggt cagtctgact tgcttggtta aagggtttta cccctctgat 1200
attgcagtgg aatgggaatc taatggtcag cctgaaaata actacaagac caccccccca 1260
gtacttgatt cagatggttc tttcttttta tattctaaat taactgtgga taaatccaga 1320
tggcaacaag ggaatgtttt cagttgctcc gtgatgcatg aggccttaca taatcattat 1380
actcagaagt ccccttagtct gtcaccgggt aagtga                          1416

SEQ ID NO: 11               moltype = AA  length = 240
FEATURE                     Location/Qualifiers
REGION                      1..240
                            note = Synthetic: Light_Chain_Amino_Acid
source                      1..240
                            mol_type = protein
                            organism = synthetic construct
SEQUENCE: 11
MGKMASLFAT FLVVLVSLSL ASESSADIQM TQSPSSLSAS VGDRVTITCR ASQDISNYLE  60
WYQQKPGKAP KLLVYNAKTL AEGVPSRFSG SGSGTDFTLT ISSLQPEDFG TYYCQHHYDT 120
PYTFGQGTKL EIKRTVAAPS VFIFPPSDEQ LKSGTASVVC LLNNFYPREA KVQWKVDNAL 180
QSGNSQESVT EQDSKDSTYS LSSTLTLSKA DYEKHKVYAC EVTHQGLSSP VTKSFNRGEC 240

SEQ ID NO: 12               moltype = DNA  length = 723
FEATURE                     Location/Qualifiers
misc_feature                1..723
```

-continued

```
                      note = Synthetic: Light_Chain_DNA
source                1..723
                      mol_type = other DNA
                      organism = synthetic construct
SEQUENCE: 12
atgggaaaaa tggcttctct ttttgctact ttccttgttg tgttggttag tctttctcta    60
gctagtgaga gtagtgctga cattcaaatg actcaatctc cgagcagctt atctgcctca   120
gtaggtgata gagtgacaat aacttgcagg gcatctcaag atatttcaaa ctacctggaa   180
tggtatcagc agaaaccagg gaaagctcca aagctccttg tttacaatgc aaagacattg   240
gctgagggtg ttccttcacg tttctctgga agtgggtcgg gcaccgactt cacgctaacc   300
atcagttccc ttcagcctga agattttgga acttattatt gtcaacatca ctatgatact   360
ccctacacat ttggtcaagg aacaaagttg gagattaaaa gaactgttgc tgctccttct   420
gtgttcattt ttccaccatc tgatgaacaa ctgaagagcg gcacagcgtc agtcgtttgt   480
ttgttgaata attttacccc tagagaggct aaagtacagt ggaaagttga taatgctctg   540
cagtctggaa attcccaaga atcagtaaca gagcaagatt caaaggattc cacctacagt   600
ctttcgtcta ctttaacatt gtctaaagca gactatgaaa agcacaaagt gtatgcttgt   660
gaagttactc atcaaggtct cagctcgccg gtgacaaaat cgttcaacag gggtgaatgt   720
tga                                                                 723
```

ANTI-CD-25 ANTIBODY

CROSS-REFERENCE TO RELATED APPLICATIONS

This application claims priority to U.S. Provisional Application Ser. No. 63/237,100, filed Aug. 25, 2021, U.S. Provisional Application Ser. No. 63/312,213, filed Feb. 21, 2022 and U.S. Provisional Application Ser. No. 63/339,182, filed May 6, 2022 the entire contents of which are incorporated herein by reference.

TECHNICAL FIELD OF THE INVENTION

This document relates to materials and methods for treating cancer, and particularly to the use of anti-CD25 antibodies to reduce or eliminate regulator T cells, increase effector T cells, and to treat cancer.

INCORPORATION-BY-REFERENCE OF MATERIALS FILED ON COMPACT DISC

The present application includes a Sequence Listing which has been submitted in ASCII format via EFS-Web and is hereby incorporated by reference in its entirety. Said ASCII copy, created on Aug. 22, 2022, is named txt_IBIO1025.xml and is 16,384 bytes in size.

BACKGROUND OF THE INVENTION

Without limiting the scope of the invention, its background is described in connection with CD25 (alpha chain of the IL-2 receptor).

CD25 (which is the alpha chain of the Interleukin-2 receptor) in humans is a protein encoded by the IL2RA gene. The interleukin 2 (IL2) receptor alpha (IL2RA) chain, (IL2RB) chain, and gamma chain (IL2RG), together form the high-affinity IL-2 receptor. Homodimeric alpha chains (IL2RA) result in low-affinity receptor. Homodimeric beta (IL2RB) chains produce a medium-affinity receptor.

CD25 is expressed by regulatory T cells. Regulatory T cells constitutively express CD25 and act to suppress the expansion of effector T cells, and maintain the healthy state and inhibit effector T cells from reacting against self-antigens or over-reacting to foreign antigens. In the case of proliferative diseases, cancer cells disable the healthy immune response by increasing the amount of regulatory T cells and thereby limiting the generation of effector T cells against them.

What are needed are novel agents that alter the proliferation of CD25-expressing regulatory T cells, for example to dampen the immune system for use in cancer therapies or to upregulate the immune system for use in autoimmune diseases.

SUMMARY OF THE INVENTION

As embodied and broadly described herein, an aspect of the present disclosure relates to a humanized antibody or binding fragments that binds human CD25, wherein the antibody or binding fragment thereof comprises: a variable heavy chain amino acid sequence of SEQ ID NO:1 or 9, or a sequence comprising at least 70% sequence identity thereto; and a variable light chain amino acid sequence of SEQ ID NO: 4 or 11, or a sequence comprising at least 70% sequence identity thereto. In one aspect, the antibody or binding fragments comprises a variable heavy chain amino acid sequence of SEQ ID NO: 1 or 9, or a sequence comprising at least 75, 80, 85, 90, 91, 92, 93, 94, 95, 96, 97, 98, 99, or 100% sequence identity to SEQ ID NO:1 or 9. In another aspect, the antibody or binding fragment comprises a variable light chain amino acid sequence of SEQ ID NO: 4 or 11, or a sequence comprising at least 75, 80, 85, 90, 91, 92, 93, 94, 95, 96, 97, 98, 99, or 100% sequence identity to SEQ ID NO: 4 or 11. In another aspect, a nucleic acid that encodes SEQ ID NO: 1 or 9, has at least 75, 80, 85, 90, 91, 92, 93, 94, 95, 96, 97, 98, 99, or 100% sequence identity to the nucleic acid sequence as set forth in SEQ ID NO: 2, 3, or 10, respectively. In another aspect, a nucleic acid that encodes SEQ ID NO: 4 or 11, has at least 75, 80, 85, 90, 91, 92, 93, 94, 95, 96, 97, 98, 99, or 100% sequence identity to the nucleic acid sequence as set forth in SEQ ID NO: 5, 6, or 12, respectively. In another aspect, the nucleic acid that encodes SEQ ID NO: 4 or 9 are sequence optimized for expression in plants. In another aspect, the antibody further comprises one or more mutations to the framework region. In another aspect, the antibody binds human CD25 and cynomologous monkey CD25, but not mouse or rat CD25. In another aspect, an $EC_{50}$ ratio of binding to human CD25 and cynomologous monkey CD25 is from about 0.75 to about 1.25. In another aspect, the antibody is afucosylated. In another aspect, the antibody is afucosylated in cellulo in a CHO cell or a plant cell. In another aspect, the antibody or binding fragment increases effector T cell function when contacted with the antibody or binding fragment.

In another embodiment, the present invention is a pharmaceutical composition comprising any one of the humanized CD25 antibodies or fragments thereof described hereinabove.

In another embodiment, the present invention is an isolated nucleic acid sequence encoding any one of the humanized CD25 antibodies described hereinabove.

In another embodiment, the present invention is an expression vector comprising the isolated nucleic acid described hereinabove.

In another embodiment, the present invention is a vector comprising the nucleic acid sequence described hereinabove.

In another embodiment, the present invention is a method of treating a subject in need thereof comprising administering to the subject a therapeutically effective amount of any one of the humanized CD25 antibodies or the pharmaceutical composition described hereinabove.

In another embodiment, the present invention is a method of depleting the number of regulatory T cells in a subject comprising administering to the subject a therapeutically effective amount of any one of the humanized CD25 antibodies or the pharmaceutical composition described hereinabove. In one aspect, the subject suffers from cancer. In another aspect, the subject suffers from an autoimmune-related disease or disorder. In another aspect, the subject is provided a co-therapy.

In another embodiment, the present invention is a method of depleting the number of regulatory T cells in a sample comprising peripheral blood mononuclear cells comprising contacting the sample with any one of the humanized CD25 antibodies described hereinabove.

In another embodiment, the present invention is a kit comprising any one of the antibodies or the pharmaceutical composition described hereinabove.

In another embodiment, the present invention is an *Agrobacterium tumefaciens* cell comprising the expression vector described hereinabove.

In another embodiment, the present invention is a method for making the polypeptide having anti-cancer activity, the method comprising: (a) introducing into a plant a plant viral vector that includes a polynucleotide encoding the polypeptide of SEQ ID NO:1 and 2 having anticancer activity; and (b) maintaining the plant under conditions and for a time sufficient that the polypeptide is expressed in at least some plant cells. In another aspect, the introducing comprises vacuum infiltration. In another aspect, the plant comprises the polypeptide having anti-cancer activity. In another aspect, the polypeptide having anti-cancer activity from the plant. In another aspect, the polypeptide having anti-cancer activity.

DESCRIPTION OF DRAWINGS

For a more complete understanding of the features and advantages of the present invention, reference is now made to the detailed description of the invention along with the accompanying figures and in which.

DETAILED DESCRIPTION

Figures 1, 2:
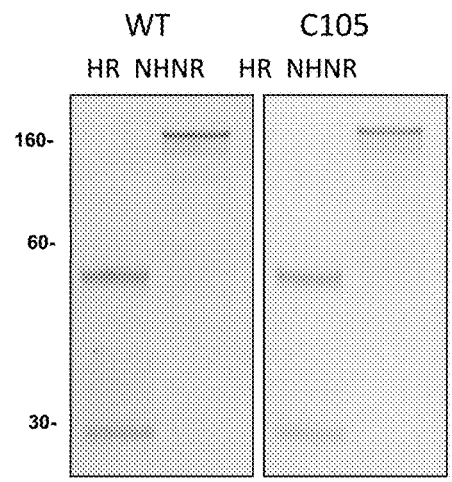
FIG. 1 is a Coomassie blue-stained gels showing recovered antibody expressed in the plant expression system, the anti-CD25 antibody made in a wild-type plant is also referred to as SD-889825-PW-A (IBIO-101, wild type Plant), and the anti-CD25 antibody manufactured in the c-105 strain is SD-889825-PC-A (IBIO-101, c-105 Plant Afucosylated).
FIG. 2 Representative Mass Spectrometry Analysis of Masses of Plant-made hD11Heavy and Light Chains (C105 plants).

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

Terms. In order to facilitate review of the various embodiments of this disclosure, the following explanations of specific terms are provided.

Unless otherwise noted, technical terms are used according to conventional usage. Definitions of common terms in molecular biology may be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: A Comprehensive Desk Reference, published by VCH Publishers, Inc., 1995 (ISBN 1-56081-569-8), relevant portions incorporated herein by reference.

Animal: Living multi-cellular vertebrate organisms, a category that includes, for example, mammals and birds. The term mammal includes both human and non-human mammals. Similarly, the term "subject" includes both human and veterinary subjects.

cDNA (complementary DNA): A piece of DNA lacking internal, non-coding segments (introns) and regulatory sequences that determine transcription. cDNA is synthesized in the laboratory by reverse transcription from messenger RNA extracted from cells.

Conservative variants: "Conservative" amino acid substitutions are those substitutions that do not substantially affect or decrease an activity of the antibody(ies) or portion(s) thereof, such as the ability of the polypeptide to prevent, reduce or eliminate a cancer and/or regulatory T cells, alone, or in combination with another anti-neoplastic therapy. Specific, non-limiting examples of conservative substitutions include the following:

| Original Residue | Conservative Substitution(s) |
|---|---|
| Ala | Ser |
| Arg | Lys |
| Asn | Gln, His |
| Asp | Glu |
| Cys | Ser |
| Gln | Asn |
| Glu | Asp |
| His | Asn; Gln |
| Ile | Leu, Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

The term conservative variation also includes the use of a substituted amino acid in place of an unsubstituted parent amino acid, provided that antibodies raised to the substituted polypeptide also immunoreact with the unsubstituted polypeptide. Non-conservative substitutions are those that reduce an activity, such as the ability of a protein to inhibit fibrosis.

As used herein, the transition phrase "consists of" refers to a polypeptide, a polypeptide that consists essentially of a specified amino acid sequence does not include any additional amino acid residues. A polypeptide that consists of a specified amino acid sequence does not include any additional amino acid residues, nor does it include additional biological components, such as nucleic acids lipids, sugars, nor does it include labels.

The transition phrase "consists essentially of" refers to a polypeptide that can include additional non-peptide components, such as labels (for example, fluorescent, radioactive, or solid particle labels), sugars or lipids, that do not materially affect the basic and novel characteristics of the polypeptide. A polypeptide that consists or consists essentially of a specified amino acid sequence can be glycosylated or have an amide modification. With regard to a polynucleotide, a polynucleotide that consists essentially of a specified nucleic acid sequence does not include any additional nucleic acid residues. However, the polynucleotide can include additional non-nucleic acid components, such as labels (for example, fluorescent, radioactive, or solid particle labels) or polypeptides, that do not materially affect the basic and novel characteristic(s)" of the polynucleotides. A polynucleotide that consists of a specified nucleic acid sequence does not include any additional nucleic acid residues, nor does it include additional biological components or labels.

Degenerate variant: A polynucleotide encoding a polypeptide that includes a sequence that is degenerate as a result of the genetic code. There are 20 natural amino acids, most of which are specified by more than one codon. Therefore, all degenerate nucleotide sequences are included in this disclosure as long as the amino acid sequence of the antibody polypeptide encoded by the nucleotide sequence is unchanged.

Expression Control Sequences: Nucleic acid sequences that regulate the expression of a heterologous nucleic acid sequence to which it is operatively linked. Expression control sequences are operatively linked to a nucleic acid sequence when the expression control sequences control and regulate the transcription and, as appropriate, translation of the nucleic acid sequence. Thus, expression control sequences can include appropriate promoters, enhancers, transcription terminators, a start codon (i.e., ATG) in front of a protein-encoding gene, splicing signal for introns, maintenance of the correct reading frame of that gene to permit proper translation of mRNA, and stop codons. The term "control sequences" is intended to include, at a minimum, components whose presence can influence expression, and can also include additional components whose presence is advantageous, for example, leader sequences and fusion partner sequences. Expression control sequences can include a promoter.

A promoter is a minimal sequence sufficient to direct transcription. Also included are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters are included (see e.g., Bitter et al., *Meth Enzymol* 153:516-544, 1987). For example, when cloning in bacterial systems, inducible promoters such as pL of bacteriophage lambda, plac, ptrp, ptac (ptrp-lac hybrid promoter) and the like can be used. In some embodiments, when cloning in mammalian cell systems, promoters derived from the genome of mammalian cells (such as the metallothionein promoter) or from mammalian viruses (such as the retrovirus long terminal repeat; the adenovirus late promoter; the vaccinia virus 7.5K promoter) can be used. Promoters produced by recombinant DNA or synthetic techniques can also be used to provide for transcription of the nucleic acid sequences.

Host cells: Cells in which a vector can be propagated, and its DNA expressed. The cell may be prokaryotic or eukaryotic. The cell can be mammalian, such as a human cell. The term also includes any progeny of the subject host cell. It is understood that all progeny may not be identical to the parental cell since there may be mutations that occur during replication. However, such progeny are included when the term "host cell" is used.

Inhibiting or treating a disease: Inhibiting a disease, such as cancer, refers to inhibiting the full development of a disease. In several examples, inhibiting a disease refers to reducing or eliminating a cancer. "Treatment" refers to a therapeutic intervention that ameliorates a sign or symptom of a disease or pathological condition related to the disease, such as the cancer.

Isolated: An "isolated" biological component (such as a nucleic acid or protein or organelle) has been substantially separated or purified away from other biological components in the cell of the organism in which the component naturally occurs, e.g., other chromosomal and extra-chromosomal DNA and RNA, proteins and organelles. Nucleic acids and proteins that have been "isolated" include nucleic acids and proteins purified by standard purification methods. The term also embraces nucleic acids and proteins prepared by recombinant expression in a host cell as well as chemically synthesized nucleic acids.

Label: A detectable compound or composition that is conjugated directly or indirectly to another molecule to facilitate detection of that molecule. Specific, non-limiting examples of labels include fluorescent tags, enzymatic linkages, and radioactive isotopes.

Linker sequence: A linker sequence is an amino acid sequence that covalently links two polypeptide domains. Linker sequences can be included in the between the Antibody or portions thereof disclosed herein to provide rotational freedom to the linked polypeptide domains and thereby to promote proper domain folding and presentation to the MHC. By way of example, in a recombinant polypeptide containing antibody polypeptides, linker sequences can be provided between them, such as a polypeptide containing antibody or portions thereof-linker-antibody or portions thereof. Linker sequences, which are generally between 2 and 25 amino acids in length, are well known in the art and include, but are not limited to, the glycine(4)-serine spacer (×3) described by Chaudhary et al., *Nature* 339:394-397, 1989.

Mammal: This term includes both human and non-human mammals. Similarly, the term "subject" includes both human and veterinary subjects.

Oligonucleotide: A linear polynucleotide sequence of up to about 100 nucleotide bases in length.

Open reading frame (ORF): A series of nucleotide triplets (codons) coding for amino acids without any internal termination codons. These sequences are usually translatable into a polypeptide.

Operably linked: A first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence, such as a sequence that encodes the antibody(ies) or portion(s) thereof. Generally, operably linked DNA sequences are contiguous and, where necessary to join two protein-coding regions, in the same reading frame.

Peptide Modifications: Antibody or portions thereof include synthetic embodiments of polypeptides described herein. In addition, analogs (non-peptide organic molecules), derivatives (chemically functionalized polypeptide molecules obtained starting with the disclosed polypeptide sequences) and variants (homologs) of these proteins can be utilized in the methods described herein. Each polypeptide of this disclosure is comprised of a sequence of amino acids, which may be either L- and/or D-amino acids, naturally occurring and otherwise.

Pharmaceutically acceptable carriers: The pharmaceutically acceptable carriers of use are conventional. Remington's Pharmaceutical Sciences, by E. W. Martin, Mack Publishing Co., Easton, Pa., 15th Edition (1975), relevant portions incorporated herein by reference, describes compositions and formulations suitable for pharmaceutical delivery of the fusion proteins herein disclosed.

In general, the nature of the carrier will depend on the particular mode of administration being employed. For instance, parenteral formulations usually include injectable fluids that include pharmaceutically and physiologically acceptable fluids such as water, physiological saline, balanced salt solutions, aqueous dextrose, glycerol or the like as a vehicle. For solid compositions (such as powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

A "therapeutically effective amount" is a quantity of a composition to achieve a desired effect in a subject being treated. For instance, this can be the amount necessary to induce an immune response, inhibit cancer, reduce scar volume, or measurably alter outward symptoms of the fibrotic condition. When administered to a subject, a dosage will generally be used that will achieve target tissue concentrations (for example, in skin cells or lung tissue) that has been shown to achieve an in vitro effect.

Polynucleotide: The term polynucleotide or nucleic acid sequence refers to a polymeric form of nucleotide at least 10 bases in length. A recombinant polynucleotide includes a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides can be ribonucleotides, deoxyribonucleotides, or modified forms of either nucleotide. The term includes single- and double-stranded forms of DNA.

Peptide or Polypeptide: Any chain of amino acids, regardless of length or post-translational modification (e.g., glycosylation or phosphorylation). In some embodiments, the polypeptide is the antibody(ies) or portion(s) thereof. A polypeptide can be between 5 and 60 amino acids in length.

In some embodiments, a polypeptide is from about 10 to about 55 amino acids in length. In yet another embodiment, a polypeptide is from about 20 to about 50 amino acids in length. In yet another embodiment, polypeptide is about 50 amino acids in length. With regard to polypeptides, the word "about" indicates integer amounts. Thus, in one example, a polypeptide "about" 50 amino acids in length is from 49 to 51 amino acids in length. In some embodiments, a polypeptide can be in multimeric form.

Post-translational modification: The modification of a newly formed protein; may involve deletion of amino acids, chemical modification of certain amino acids (for example, amidation, acetylation, phosphorylation, glycosylation, formation of pyroglutamate, oxidation/reduction of sulfa group on a methionine, or addition of similar small molecules) to certain amino acids.

Probes and primers: A probe includes an isolated nucleic acid attached to a detectable label or reporter molecule. Primers are short nucleic acids, preferably DNA oligonucleotides, of about 15 nucleotides or more in length. Primers may be annealed to a complementary target DNA strand by nucleic acid hybridization to form a hybrid between the primer and the target DNA strand, and then extended along the target DNA strand by a DNA polymerase enzyme. Primer pairs can be used for amplification of a nucleic acid sequence, for example by polymerase chain reaction (PCR) or other nucleic-acid amplification methods known in the art. One of skill in the art will appreciate that the specificity of a particular probe or primer increases with its length. Thus, for example, a primer containing 20 consecutive nucleotides will anneal to a target with a higher specificity than a corresponding primer of only 15 nucleotides. Thus, in order to obtain greater specificity, probes and primers can be selected that contain about 20, 25, 30, 35, 40, 50 or more consecutive nucleotides.

Purified: The Antibody or portions thereof disclosed herein can be purified (and/or synthesized) by any of the means known in the art (see, e.g., Guide to Protein Purification, ed. Deutscher, Meth. Enzymol. 185, Academic Press, San Diego, 1990; and Scopes, Protein Purification: Principles and Practice, Springer Verlag, New York, 1982), relevant portions incorporated herein by reference. Substantial purification denotes purification from other proteins or cellular components. A substantially purified protein is at least about 60%, 70%, 80%, 90%, 95%, 98% or 99% pure. Thus, in one specific, non-limiting example, a substantially purified protein is 90% free of other proteins or cellular components.

Native antibodies and immunoglobulins are usually heterotetrameric glycoproteins of about 150,000 daltons, composed of two identical light (L) chains and two identical heavy (H) chains. Each light chain is linked to a heavy chain by one covalent disulfide bond. While the number of disulfide linkages varies between the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end. The constant domain of the light chain is aligned with the first constant domain of the heavy chain, and the light chain variable domain is aligned with the variable domain of the heavy chain. Particular amino acid residues are believed to form an interface between the light and heavy chain variable domains (Clothia et al., J. Mol. Biol. 186, 651-66, 1985); Novotny and Haber, Proc. Natl. Acad. Sci. USA 82 4592-4596 (1985), relevant portions incorporated herein by reference.

Thus, the term purified does not require absolute purity; rather, it is intended as a relative term. For example, a purified nucleic acid is one in which the nucleic acid is more enriched than the nucleic acid in its natural environment within a cell. In additional embodiments, a nucleic acid or cell preparation is purified such that the nucleic acid or cell represents at least about 60% (such as, but not limited to, 70%, 80%, 90%, 95%, 98% or 99%) of the total nucleic acid or cell content of the preparation, respectively.

Recombinant: A recombinant nucleic acid is one that has a sequence that is not naturally occurring or has a sequence that is made by an artificial combination of two otherwise separated segments of sequence. This artificial combination is often accomplished by chemical synthesis or, more commonly, by the artificial manipulation of isolated segments of nucleic acids, e.g., by genetic engineering techniques.

Selectively hybridize: Hybridization under moderately or highly stringent conditions that excludes non-related nucleotide sequences.

In nucleic acid hybridization reactions, the conditions used to achieve a particular level of stringency will vary, depending on the nature of the nucleic acids being hybridized. For example, the length, degree of complementarity, nucleotide sequence composition (for example, GC v. AT content), and nucleic acid type (for example, RNA versus DNA) of the hybridizing regions of the nucleic acids can be considered in selecting hybridization conditions. An additional consideration is whether one of the nucleic acids is immobilized, for example, on a filter.

A specific example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). One of skill in the art can readily determine variations on these conditions (e.g., Molecular Cloning: A Laboratory Manual, 2nd ed., vol. 1-3, ed. Sambrook et al., Cold Spring Harbor Laboratory Press, Cold Spring Harbor, N.Y., 1989), relevant portions incorporated herein by reference. Washing can be carried out using only one of these conditions, e.g., high stringency conditions, or each of the conditions can be used, e.g., for 10-15 minutes each, in the order listed above, repeating any or all of the steps listed. However, as mentioned above, optimal conditions will vary, depending on the particular hybridization reaction involved, and can be determined empirically.

Sequence identity: The similarity between amino acid sequences is expressed in terms of the similarity between the sequences, otherwise referred to as sequence identity. Sequence identity is frequently measured in terms of percentage identity (or similarity or homology); the higher the percentage, the more similar the two sequences are. Homologs or variants of the antibody(ies) or portion(s) thereof will possess a relatively high degree of sequence identity when aligned using standard methods.

Methods of alignment of sequences for comparison are well known in the art. Various programs and alignment algorithms are described in: Smith and Waterman, Adv. Appl. Math. 2:482, 1981; Needleman and Wunsch, J. Mol. Biol. 48:443, 1970; Higgins and Sharp, Gene 73:237, 1988; Higgins and Sharp, CABIOS 5:151, 1989; Corpet et al., *Nucleic Acids Research* 16:10881, 1988; and Pearson and Lipman, *Proc. Natl. Acad. Sci. USA* 85:2444, 1988. Altschul et al., *Nature Genet.* 6:119, 1994, presents a detailed consideration of sequence alignment methods and homology calculations, relevant portions incorporated herein by reference.

The NCBI Basic Local Alignment Search Tool (BLAST) (Altschul et al., *J. Mol. Biol.* 215:403, 1990), relevant portions incorporated herein by reference, is available from several sources, including the National Center for Biotechnology Information (NCBI, Bethesda, Md.) and on the internet, for use in connection with the sequence analysis programs blastp, blastn, blastx, tblastn and tblastx. A description of how to determine sequence identity using this program is available on the NCBI website on the internet.

Homologs and variants of the antibody(ies) or portion(s) thereof are typically characterized by possession of at least 75%, for example at least 80%, sequence identity counted over the full length alignment with the amino acid sequence of the antibody(ies) or portion(s) thereof using the NCBI Blast 2.0, gapped blastp set to default parameters. For comparisons of amino acid sequences of greater than about 30 amino acids, the Blast 2 sequences function is employed using the default BLOSUM62 matrix set to default parameters, (gap existence cost of 11, and a per residue gap cost of 1). When aligning short peptides (fewer than around 30 amino acids), the alignment should be performed using the Blast 2 sequences function, employing the PAM30 matrix set to default parameters (open gap 9, extension gap 1 penalties). Proteins with even greater similarity to the reference sequences will show increasing percentage identities when assessed by this method, such as at least 80%, at least 85%, at least 90%, at least 95%, at least 98%, or at least 99% sequence identity. When less than the entire sequence is being compared for sequence identity, homologs and variants will typically possess at least 80% sequence identity over short windows of 10-20 amino acids, and can possess sequence identities of at least 85% or at least 90% or 95% depending on their similarity to the reference sequence. Methods for determining sequence identity over such short windows are available at the NCBI website on the internet. One of skill in the art will appreciate that these sequence identity ranges are provided for guidance only; it is entirely possible that strongly significant homologs could be obtained that fall outside of the ranges provided.

Therapeutically effective amount: A quantity of compound, such as the antibody(ies) or portion(s) thereof sufficient to achieve a desired effect in a subject being treated. For instance, this can be the amount necessary to treat or ameliorate cancer, such as skin or lung cancer, in a subject. In some embodiments, it is the amount necessary to treat a subject by a measurable amount over a period of time, or to measurably inhibit progression of disease, in a subject. In other embodiments, a therapeutically effective amount is the amount necessary to prophylactically inhibit a disease.

An effective amount of the antibody(ies) or portion(s) thereof may be administered in a single dose, or in several doses, for example daily, during a course of treatment. However, the effective amount will be dependent on the compound applied, the subject being treated, the severity and type of the affliction, and the manner of administration of the compound.

The present invention can be provided with one or more anti-neoplastic agents. Example of co-therapies with other anti-neoplastic agents include, e.g., aclarubicin, aldesleukin, alemtuzumab, alitretinoin, altretamine, amifostine, aminolevulinic acid, amrubicin, amsacrine, anagrelide, anastrozole, ANGER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, imiquimod, interferon alfa or interferon alfa family members, interferon beta or interferon beta family members, interferon gamma or interferon gamma family members, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburiembodiment, rhenium $^{186}$Re etidronate, RII retinamide, rituximab, romurtide, $^{153}$samarium lexidronam, sargramostim, sizofiran, sobuzoxane, sonermin, $^{89}$strontium chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-$^{131}$iodine, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SD01, fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb, idiotypic 105AD7 MAb, idiotypic CEA MAb (Trilex), LYM-1-$^{131}$iodine MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), or valspodar.

Non-limiting examples of PD-1 (programmed cell death-1) receptor is expressed on the surface of activated T cells. Its ligands, PD-L1 and PD-L2, are expressed on the surface of dendritic cells or macrophages. PD-1 and PD-L1/PD-L2 belong to the family of immune checkpoint proteins that act as co-inhibitory factors that can halt or limit the development of the T cell response. The PD-1/PD-L1 interaction ensures that the immune system is activated only at the appropriate time in order to minimize the possibility of chronic autoimmune inflammation. Example of blocking immune checkpoint proteins, include anti-PD-1, anti-PD-L1 and anti-CTLA-4, with monoclonal antibodies, Transduced: A transduced cell is a cell into which has been introduced a nucleic acid molecule by molecular biology techniques. As used herein, the term transduction encompasses all techniques by which a nucleic acid molecule might be introduced into such a cell, including transfection with viral vectors, transformation with plasmid vectors, and introduction of naked DNA by electroporation, lipofection, and particle gun acceleration.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker gene and other genetic elements known in the art. Vectors include plasmid vectors, including plasmids for expression in gram negative and gram positive bacterial cell. Exemplary vectors include those for expression in *E. coli* and *Salmonella*. Vectors also include viral vectors, such as, but are not limited to, retrovirus, orthopox, avipox, fowlpox, capripox, suipox, adenoviral, herpes virus, alpha virus, baculovirus, Sindbis virus, vaccinia virus and poliovirus vectors. Vectors also include vectors for expression in yeast cells and insect cells.

Other amino acids that can be substituted, inserted or deleted at these or other locations can be identified by mutagenesis studies coupled with biological assays. The above alignment is provided only as a guideline.

In exemplary embodiments, the antibody is engineered to be bispecific, trispecific, or multi-specific, and the antibody comprises two or more distinct antigen-binding regions. In one example, the antibody is a bispecific or trispecific antibody specific for CD25. Methods of making bispecific or trispecific antibodies are known in the art. See, for example, Marvin and Zhu, Acta Pharmacologica Sinica 26: 649-658 (2005) and U.S. Pat. No. 6,551,592, relevant portions incorporated herein by reference. In another example, the binding construct is a bi-specific antigen-binding construct specific for a first epitope of CD25 and a second epitope of CD25. The antibody can be a quadroma, heterodimeric bispecific antibody, bispecific antibody fusion protein, a bispecific antibody fragment, a bispecific T-cell engager (BiTE), or a multi-specific antibody. The antibody can be engineered to be bivalent, trivalent, or multivalent. See, e.g., Cuesta et al., "Multivalent antibodies: when design surpasses evolution" *Trends in Biotechnology* 28, 355-362 (2010); Holliger et al., "Engineered antibody fragments and the rise of single domains" *Nat. Biotechnol.* 23, 1126-1136 (2005); Chan et al., "Therapeutic antibodies for autoimmunity and inflammation" *Nat Rev Immunol* 10, 301-316 (2010); Byrne et al., "A tale of two specificities: bispecific antibodies for therapeutic and diagnostic applications" *Trends Biotechnol.* 31, 621-632 (2013), relevant portions incorporated herein by reference. If the antibody is in monomeric form, the antibody can also be conjugated to one or more other antibodies (i.e., that recognize the same or a different epitope than the first antibody). Thus, the antibody can be dimeric, polymeric, oligomeric, or multimeric form.

An antigen-binding fragment of the antibody comprises the "antigen-binding domain" or "antigen-binding portion" of the antibody. The antigen-binding fragment has at least one antigen binding site and includes, but is not limited to: Fab, F(ab')$_2$, a monospecific or bispecific Fab$_2$, a trispecific Fabs, a monovalent IgG, scFv, dsFv, scFv-Fc, bispecific diabodies, trispecific triabodies, minibodies, or a fragment of IgNAR (e.g., V-NAR), bis-scFvs, or fragments expressed by a Fab expression library.

The antibody or binding fragments thereof can be monomeric or polymeric, bispecific or trispecific, bivalent or trivalent. In exemplary aspects, the fusion proteins provided herein are monospecific, bispecific or trispecific, bivalent or trivalent and can be fully human.

Antibody fragments that contain the antigen-binding domain of the antibody molecule may be generated by techniques known in the art. For example, such fragments include, but are not limited to, the F(ab')$_2$ fragment which may be produced by pepsin digestion of the antibody molecule; the Fab' fragments which may be generated by reducing the disulfide bridges of the F(ab')$_2$ fragment; and the two Fab' fragments which may be generated by treating the antibody molecule with papain and a reducing agent.

A single-chain variable region fragment (sFv) antibody fragment is a truncated Fab fragment comprising the variable (V) domain of an antibody heavy chain linked to a V domain of a light antibody chain via a synthetic peptide and can be generated using routine recombinant DNA technology techniques. Disulfide-stabilized variable region fragments (dsFv) can be prepared by recombinant DNA technology (see, e.g., Reiter et al., *Protein Engineering*, 7, 697-704 (1994)), relevant portions incorporated herein by reference.

Recombinant antibody fragments, such as scFvs, can also be engineered to assemble into stable multimeric oligomers of high binding avidity and specificity to different target antigens. Such diabodies (dimers), triabodies (trimers) or tetrabodies (tetramers) are well known in the art, see e.g., Kortt et al., Biomol Eng. 2001 18:95-108, (2001) and Todorovska et al., J Immunol Methods. 248:47-66, (2001), relevant portions incorporated herein by reference.

In certain examples, the antigen-binding fragment can include two or more distinct antigen-binding domains. In one example, the binding construct is a bi-specific antigen-binding fragment specific for a first epitope of CD25 and a second epitope of CD25. In one example, the binding domain can be dimerized, trimerized or made multi-valent via the helix-turn-helix motif.

Also encompassed herein are multimers of polypeptides containing an antibody or portions thereof, including fusion polypeptides as described below. In some embodiments, a multimer can be a dimer, trimer, tetramer, or pentamer.

Also encompassed herein are antibody or portions thereof that are fused to a heterologous peptide, such as a peptide that can be used for detecting, purifying, stabilizing, or solubilizing the antibody(ies) or portion(s) thereof. In some embodiments, a C-terminal polypeptide can be linked to an immunoglobulin (Ig) constant heavy or light chain domain or portion thereof at its N-terminus. For example, a polypeptide may be linked to a CH1, CH2 and/or CH3 domain of a heavy chain. If the constant region is from a light chain, it can be from a kappa or lambda light chain. If the constant region is from a heavy chain, it can be from an antibody of any one of the following classes of antibodies: IgG, IgA, IgE, IgD, and IgM. IgG can be an IgG1, IgG2, IgG3 or IgG4. The constant domain may be an Fc fragment. The constant domain can be from a mammalian antibody, such as a human antibody. Soluble receptor-IgG fusion proteins are common immunological reagents and methods for their construction are known in the art (see, for example, U.S. Pat. Nos. 5,225,538, 5,726,044; 5,707,632; 750,375, 5,925,351, 6,406,697 and Bergers et al. Science 1999 284: 808-12). In one example, the immunoglobulin is the constant part of the heavy chain of human IgG, particularly IgG1, where dimerization between two heavy chains takes place at the hinge region. It is recognized that inclusion of the CH2 and CH3 domains of the Fc region as part of the fusion polypeptide increases the in vivo circulation half-life of the polypeptide comprising the Fc region, and that of the oligomer or dimer comprising the polypeptide.

The following sequences include the nucleic acid and amino acid sequences for the various light and heavy chains of the monoclonal antibodies, in these specific cases made into scFvs. Further, the Complementarity Determining Regions (CDRs) were determined using the software available from IMGT.org using Kabat rules. The tables that follow include alternative CDR sequences comparing Kabat, Clothia, and IMGT rules, all of which can be used with the present invention to modify an antibody backbone (e.g., a human antibody) with the CDRs disclosed herein.

Sequences Example 1. SEQ ID NO:1 is ExtSP-hD11 heavy Chain (HC). Underlined is the heavy chain constant region, Bold, extensin signal peptide, CDR.

MGKMASLFATFLVVLVSLSLASESSAQVQLVQSGAEVKKPGASLKISCK
GS<u>GYTFTDY</u>AMHWVRQAPGQGLEWIGV<u>ISTYSGDA</u>IYAQKFQGRATMTV
DTSTS<u>TAYL</u>ELSSLRSEDTAVYYCARGVTFDYWGQGTTVTVSSA<u>STKGP
SVFPLAPSSKSTSGGTAALGCLVKDYFPEPVTVSWNSGALTSGVHTFPA
VLQSSGLYSLSSVVTVPSSSLGTQTYICNVNHKPSNTKVDKRVEPKSCD
KTHTCPPCPAPELLGGPSVFLFPPKPKDTLMISRTPEVTCVVVDVSHED
PEVKFNWYVDGVEVHNAKTKPREEQYNSTYRVVSVLTVLHQDWLNGKEY
KCKVSNKALPAPIEKTISKAKGQPREPQVYTLPPSREEMTKNQVSLTCL
VKGFYPSDIAVEWESNGQPENNYKTTPPVLDSDGSFFLYSKLTVDKSRW
QQGNVFSCSVMHEALHNHYTQKSLSLSPGK</u>

SEQ ID NO:2 is ExtSP-hD11 HC, Codon optimized version 1, Underlined is the heavy chain constant region, Bold, extensin signal peptide.

**ATGGGAAAAATGGCTTCTCTTTTTGCTACTTTCCTTGTTGTGTTGGTTA
GTCTTTCTCTAGCTAGTGAGAGTAGTGCT**CAAGTTCAGCTGGTGCAGAG
TGGTGCTGAGGTGAAGAAACCTGGTGCCTCATTGAAATTTCGTGCAAA
GGGAGCGGGTACACTTTCACCGACTACGCAATGCATTGGGTAAGGCAAG
CACCAGGTCAAGGCTTAGAATGGATTGGAGTCATCAGCACCTACTCTGG
TGATGCCATATATGCTCAAAAGTTTCAGGGAAGAGCGACAATGACTGTT
GATACATCAACTTCTACAGCATATCTTGAGTTGTCATCCCTCCGTAGTG
AAGATACTGCTGTTTATTATTGTGCTAGAGGCGTAACATTTGATTATTG
GGGACAAGGAACAACTGTCACGGTTTCTTCC<u>GCTAGCACCAAAGGTCCT
TCAGTCTTCCCACTTGCGCCAAGTTCCAAAAGCACTTCTGGCGGCACTG
CTGCGCTTGGCTGTCTCGTAAAAGACTATTTTCCAGAGCCAGTGACAGT
CAGTTGGAATAGCGGTGCTCTCACAAGTGGCGTTCATACATTTCCTGCT
GTTCTGCAATCTTCTGGTTTATACTCTTTATCGAGCGTAGTAACAGTTC
CTTCATCATCACTTGGGACTCAAACTTATATATGTAATGTCAACCACAA
GCCGTCCAACACTAAAGTAGACAAGAGGGTTGAACCAAAATCTTGTGAT
AAGACACACACTTGCCCTCCTTGTCCTGCACCAGAGCTCTTGGGTGGTC
CATCAGTGTTTCTATTCCCGCCAAAGCCAAAGGATACACTCATGATATC
ACGCACCCCTGAGGTTACTTGTGTTGTAGTTGATGTTAGTCATGAAGAT
CCGGAAGTGAAGTTTAATTGGTATGTTGATGGAGTGGAAGTTCACAATG
CAAAAACCAAGCCTCGTGAAGAGCAGTACAATTCAACATATCGTGTTGT
TTCAGTTCTAACAGTCCTTCATCAAGATTGGTTGAATGGAAAAGAATAT
AAATGCAAGGTGAGCAACAAAGCACTTCCAGCTCCAATTGAGAAAACAA
TTAGCAAGGCAAAGGGACAACCAAGAGAACCTCAAGTTTACACGCTTCC
TCCCTCCCGAGAAGAAATGACAAAGAATCAGGTCAGTCTGACTTGCTTG
GTTAAAGGGTTTTACCCCTCTGATATTGCAGTGGAATGGGAATCTAATG
GTCAGCCTGAAAATAACTACAAGACCACCCCCCCAGTACTTGATTCAGA
TGGTTCTTTCTTTTTATATTCTAAATTAACTGTGGATAAATCAAGATGG
CAACAAGGGAATGTTTTCAGTTGCTCCGTGATGCATGAGGCCTTACATA
ATCATTATACTCAGAAGTCCCTTAGTCTGTCACCGGGTAAGTGA</u>

SEQ ID NO:3 is ExtSP-hD11 HC, Codon optimized version 2, Underlined is the heavy chain constant region, Bold, extensin signal peptide.

**ATGGGAAAAATGGCTTCTCTTTTTGCTACTTTCCTTGTTGTGTTGGTTA
GTCTTTCTCTAGCTAGTGAGAGTAGTGCT**CAAGTTCAGCTTGTACAGTC
TGGGGCTGAGGTGAAGAAACCAGGGGCATCCTTAAAAATTTCTTGCAAA
GGATCAGGCTACACTTTCACTGATTATGCAATGCATTGGGTTAGGCAAG
CTCCTGGTCAAGGTCTCGAATGGATTGGAGTCATCTCAACCTACTCTGG
TGATGCAATATATGCTCAAAAGTTTCAAGGAAGAGCGACAATGACTGTT
GACACCTCAACAAGTACAGCCTATTTGGAGCTGAGCAGCCTAAGAAGTG
AAGATACTGCCGTTTATTATTGTGCTCGTGGCGTAACATTTGATTACTG
GGGTCAGGGAACTACGGTGACAGTCTCGTCC<u>GCTAGCACCAAAGGTCCT
TCAGTCTTCCCACTTGCGCCAAGTTCCAAAAGCACTTCTGGCGGCACTG
CTGCGCTTGGCTGTCTCGTAAAAGACTATTTTCCAGAGCCAGTGACAGT
CAGTTGGAATAGCGGTGCTCTCACAAGTGGCGTTCATACATTTCCTGCT
GTTCTGCAATCTTCTGGTTTATACTCTTTATCGAGCGTAGTAACAGTTC
CTTCATCATCACTTGGGACTCAAACTTATATATGTAATGTCAACCACAA
GCCGTCCAACACTAAAGTAGACAAGAGGGTTGAACCAAAATCTTGTGAT
AAGACACACACTTGCCCTCCTTGTCCTGCACCAGAGCTCTTGGGTGGTC
CATCAGTGTTTCTATTCCCGCCAAAGCCAAAGGATACACTCATGATATC
ACGCACCCCTGAGGTTACTTGTGTTGTAGTTGATGTTAGTCATGAAGAT
CCGGAAGTGAAGTTTAATTGGTATGTTGATGGAGTGGAAGTTCACAATG
CAAAAACCAAGCCTCGTGAAGAGCAGTACAATTCAACATATCGTGTTGT
TTCAGTTCTAACAGTCCTTCATCAAGATTGGTTGAATGGAAAAGAATAT</u>

AAATGCAAGGTGAGCAACAAAGCACTTCCAGCTCCAATTGAGAAAACAA

TTAGCAAGGCAAAGGGACAACCAAGAGAACCTCAAGTTTACACGCTTCC

TCCCTCCCGAGAAGAAATGACAAAGAATCAGGTCAGTCTGACTTGCTTG

GTTAAAGGGTTTTACCCCTCTGATATTGCAGTGGAATGGGAATCTAATG

GTCAGCCTGAAAATAACTACAAGACCACCCCCCCAGTACTTGATTCAGA

TGGTTCTTTCTTTTTATATTCTAAATTAACTGTGGATAAATCAAGATGG

CAACAAGGGAATGTTTTCAGTTGCTCCGTGATGCATGAGGCCTTACATA

ATCATTATACTCAGAAGTCCCTTAGTCTGTCACCGGGTAAGTGA

SEQ ID NO:4 is ExtSP-hD11 Light Chain (LC), Italics, light chain constant region, Bold, extensin signal peptide, CDR.

MGKMASLFATFLVVLVSLSLASESSADIQMTQSPSSLSASVGDRVTITC RASQ<u>DISNYL</u>EWYQQKPGKAPKLLVY<u>NAKT</u>LAEGVPSRFSGSGSGTD<u>FT LTI</u>SSLQPEDFGTYYCQHHYDTPYTFGQGTKLEIKR*TVAAPSVFIFPPS DEQLKSGTASVVCLLNNFYPREAKVQWKVDNALQSGNSQESVTEQDSKD STYSLSSTLTLSKADYEKHKVYACEVTHQGLSSPVTKSFNRGEC*

SEQ ID NO:5 is ExtSP-hD11 Light Chain (LC), codon optimized version 1, Italics, light chain constant region, Bold, extensin signal peptide.

atgggaaaaatggcttctcttttgctactttccttgttgtgttggta gtctttctctagctagtgagagtagtgctGACATTCAAATGACACAGAG

TCCATCAAGCCTCAGTGCTTCTGTTGGAGACCGTGTTACAATTACATGC

AGGGCCTCTCAAGATATATCCAACTACTTGGAATGGTATCAACAGAAAC

CCGGAAAAGCACCAAAGCTTTTAGTGTACAATGCTAAAACTCTGGCAGA

GGGTGTACCTTCAAGATTCAGCGGTTCAGGCAGTGGCACTGATTTCACA

CTAACGATCTCTTCTCTTCAGCCGGAAGATTTTGGGACTTATTATTGTC

AACATCACTATGATACCCCTTACACTTTTGGTCAAGGAACCAAGTTGGA

GATTAAGAGAACTGTTGCTGCTCCTTCTGTGTTCATTTTTCCACCATCT

*GATGAACAACTGAAGAGCGGCACAGCGTCAGTCGTTTGTTTGTTGAATA

ATTTTTACCCTAGAGAGGCTAAAGTACAGTGGAAAGTTGATAATGCTCT

GCAGTCTGGAAATTCCCAAGAATCAGTAACAGAGCAAGATTCAAAGGAT

TCCACCTACAGTCTTTCGTCTACTTTAACATTGTCTAAAGCAGACTATG

AAAAGCACAAAGTGTATGCTTGTGAAGTTACTCATCAAGGTCTCAGCTC

GCCGGTGACAAAATCGTTCAACAGGGGTGAATGTTGA*

SEQ ID NO:6 is ExtSP-hD11 Light Chain (LC), codon optimized version 2, Italics, light chain constant region, Bold, extensin signal peptide.

ATGGGAAAAATGGCTTCTCTTTTTGCTACTTTCCTTGTTGTGTTGGTTA GTCTTTCTCTAGCTAGTGAGAGTAGTGCTGACATTCAAATGACTCAATC

TCCGAGCAGCTTATCTGCCTCAGTAGGTGATAGAGTGACAATAACTTGC

AGGGCATCTCAAGATATTTCAAACTACCTGGAATGGTATCAGCAGAAAC

CAGGGAAAGCTCCAAAGCTCCTTGTTTACAATGCAAAGACATTGGCTGA

GGGTGTTCCTTCACGTTTCTCTGGAAGTGGGTCGGGCACCGACTTCACG

CTAACCATCAGTTCCCTTCAGCCTGAAGATTTTGGAACTTATTATTGTC

AACATCACTATGATACTCCCTACACATTTGGTCAAGGAACAAAGTTGGA

GATTAAAAGAACTGTTGCTGCTCCTTCTGTGTTCATTTTTCCACCATCT

*GATGAACAACTGAAGAGCGGCACAGCGTCAGTCGTTTGTTTGTTGAATA

ATTTTTACCCTAGAGAGGCTAAAGTACAGTGGAAAGTTGATAATGCTCT

GCAGTCTGGAAATTCCCAAGAATCAGTAACAGAGCAAGATTCAAAGGAT

TCCACCTACAGTCTTTCGTCTACTTTAACATTGTCTAAAGCAGACTATG

AAAAGCACAAAGTGTATGCTTGTGAAGTTACTCATCAAGGTCTCAGCTC

GCCGGTGACAAAATCGTTCAACAGGGGTGAATGTTGA*

An Fc portion of human IgG1 which includes the hinge region, and domains CH2 and CH3 has the nucleotide sequence (SEQ ID NO:7):

GAG CCC AAA TCT TGT GAC AAA ACT CAC ACA TGC CCA
CCG TGC CCA GCA CCT GAA CTC CTG GGG GGA CCG TCA
GTC TTC CTC TTC CCC CCA AAA CCC AAG GAC ACC CTC
ATG ATC TCC CGG ACC CCT GAG GTC ACA TGC GTG GTG
GTG GAC GTG AGC CAC GAA GAC CCT GAG GTC AAG TTC
AAC TGG TAC GTG GAC GGC GTG GAG GTG CAT AAT GCC
AAG ACA AAG CCG CGG GAG GAG CAG TAC AAC AGC ACG
TAC CGT GTG GTC AGC GTC CTC ACC GTC CTG CAC CAG
GAC TGG CTG AAT GGC AAG GAG TAC AAG TGC AAG GTC
TCC AAC AAA GCC CTC CCA GCC CCC ATC GAG AAA ACC
ATC TCC AAA GCC AAA GGG CAG CCC CGA GAA CCA CAG
GTG TAC ACC CTG CCC CCA TCC CGG GAT GAG CTG ACC
AAG AAC CAG GTC AGC CTG ACC TGC CTG GTC AAA GGC
TTC TAT CCC AGC GAC ATC GCC GTG GAG TGG GAG AGC
AAT GGG CAG CCG GAG AAC AAC TAC AAG ACC ACG CCT
CCC GTG CTG GAC TCC GAC GGC TCC TTC TTC CTC TAC
AGC AAG CTC ACC GTG GAC AAG AGC AGG TGG CAG CAG
GGG AAC GTC TTC TCA TGC TCC GTG ATG CAT GAG GCT
CTG CAC AAC CAC TAC ACG CAG AAG AGC CTC TCC CTG
TCT CCG GGT AAA TGA, which encodes a polypeptide having the amino acid sequence (SEQ ID NO:8):

```
Glu Pro Lys Ser Cys Asp Lys Thr His Thr Cys Pro Pro Cys Pro
Ala Pro Glu Leu Leu Gly Gly Pro Ser Val Phe Leu Phe Pro Pro
Lys Pro Lys Asp Thr Leu Met Ile Ser Arg Thr Pro Glu Val Thr
Cys Val Val Val Asp Val Ser His Glu Asp Pro Glu Val Lys Phe
Asn Trp Tyr Val Asp Gly Val Glu Val His Asn Ala Lys Thr Lys
Pro Arg Glu Glu Gln Tyr Asn Ser Thr Tyr Arg Val Val Ser Val
Leu Thr Val Leu His Gln Asp Trp Leu Asn Gly Lys Glu Tyr Lys
Cys Lys Val Ser Asn Lys Ala Leu Pro Ala Pro Ile Glu Lys Thr Ile
Ser Lys Ala Lys Gly Gln Pro Arg Glu Pro Gln Val Tyr Thr Leu
Pro Pro Ser Arg Asp Glu Leu Thr Lys Asn Gln Val Ser Leu Thr
Cys Leu Val Lys Gly Phe Tyr Pro Ser Asp Ile Ala Val Glu Trp Glu
Ser Asn Gly Gln Pro Glu Asn Asn Tyr Lys Thr Thr Pro Pro Val
Leu Asp Ser Asp Gly Ser Phe Phe Leu Tyr Ser Lys Leu Thr Val
Asp Lys Ser Arg Trp Gln Gln Gly Asn Val Phe Ser Cys Ser Val
Met His Glu Ala Leu His Asn His Tyr Thr Gln Lys Ser Leu Ser
Leu Ser Pro Gly Lys
```

Sequence Example 2.
>Heavy_Chain_Amino_Acids SEQ ID NO:9, CDR

MGKMASLFATFLVVLVSLSLASESSAQVQLVQSGAEVKKPGASLKISCK
GS<u>GYTFTDY</u>AMHWVRQAPGQGLEWIGV<u>ISTYSGDA</u>IYAQKFQGRATMTV
DTSTS<u>TAYL</u>ELSSLRSEDTAVYYCARGVTFDYWGQGTTVTVSSASTKGP
SVFPLAPSSKSTSGGTAALGCLVKDYFPEPVTVSWNSGALTSGVHTFPA
VLQSSGLYSLSSVVTVPSSSLGTQTYICNVNHKPSNTKVDKKVEPKSCD
KTHTCPPCPAPELLGGPSVFLFPPKPKDTLMISRTPEVTCVVVDVSHED
PEVKFNWYVDGVEVHNAKTKPREEQYNSTYRVVSVLTVLHQDWLNGKEY
KCKVSNKALPAPIEKTISKAKGQPREPQVYTLPPSREEMTKNQVSLTCL
VKGFYPSDIAVEWESNGQPENNYKTTPPVLDSDGSFFLYSKLTVDKSRW
QQGNVFSCSVMHEALHNHYTQKSLSLSPGK*

>Heavy_Chain_DNA SEQ ID NO:10

<u>ATGGGAAAAATGGCTTCTCTTTTTGCTACTTTCCTTGTTGTGTTGGTTA
GTCTTTCTCTAGCTAGTGAGAGTAGTGCT</u>CAAGTTCAGCTGGTGCAGAG
TGGTGCTGAGGTGAAGAAACCTGGTGCCTCATTGAAAATTTCGTGCAAA
GGGAGCGGGTACACTTTCACCGACTACGCAATGCATTGGGTAAGGCAAG
CACCAGGTCAAGGCTTAGAATGGATTGGAGTCATCAGCACCTACTCTGG
TGATGCCATATATGCTCAAAAGTTTCAGGGAAGAGCGACAATGACTGTT
GATACATCAACTTCTACAGCATATCTTGAGTTGTCATCCCTCCGTAGTG
AAGATACTGCTGTTTATTATTGTGCTAGAGGCGTAACATTTGATTATTG

GGGACAAGGAACAACTGTCACGGTTTCTTCCGCTAGCACCAAAGGTCCT
TCAGTCTTCCCACTTGCGCCAAGTTCCAAAAGCACTTCTGGCGGCACTG
CTGCGCTTGGCTGTCTCGTAAAAGACTATTTTCCAGAGCCAGTGACAGT
CAGTTGGAATAGCGGTGCTCTCACAAGTGGCGTTCATACATTTCCTGCT
GTTCTGCAATCTTCTGGTTTATACTCTTTATCGAGCGTAGTAACAGTTC
CTTCATCATCACTTGGGACTCAAACTTATATATGTAATGTCAACCACAA
GCCGTCCAACACTAAAGTAGACAAGAAGGTTGAACCAAAATCTTGTGAT
AAGACACACACTTGCCCTCCTTGTCCTGCACCAGAGCTCTTGGGTGGTC
CATCAGTGTTTCTATTCCCGCCAAAGCCAAAGGATACACTCATGATATC
ACGCACCCCTGAGGTTACTTGTGTTGTAGTTGATGTTAGTCATGAAGAT
CCGGAAGTGAAGTTTAATTGGTATGTTGATGGAGTGGAAGTTCACAATG
CAAAAACCAAGCCTCGTGAAGAGCAGTACAATTCAACATATCGTGTTGT
TTCAGTTCTAACAGTCCTTCATCAAGATTGGTTGAATGGAAAAGAATAT
AAATGCAAGGTGAGCAACAAAGCACTTCCAGCTCCAATTGAGAAAACAA
TTAGCAAGGCAAAGGGACAACCAAGAGAACCTCAAGTTTACACGCTTCC
TCCCTCCCGAGAAGAAATGACAAAGAATCAGGTCAGTCTGACTTGCTTG
GTTAAAGGGTTTTACCCCTCTGATATTGCAGTGGAATGGGAATCTAATG
GTCAGCCTGAAAATAACTACAAGACCACCCCCCCAGTACTTGATTCAGA
TGGTTCTTTCTTTTTATATTCTAAATTAACTGTGGATAAATCAAGATGG
CAACAAGGGAATGTTTTCAGTTGCTCCGTGATGCATGAGGCCTTACATA
ATCATTATACTCAGAAGTCCCTTAGTCTGTCACCGGGTAAGTGA

>Light_Chain_Amino_Acids SEQ ID NO: 11, CDR

MGKMASLFATFLVVLVSLSLASESSAD IQMTQSPSSLSASVGDRVTITC
RAS<u>QDISNYL</u>EWYQQKPGKAPKLLVY<u>NAKT</u>LAEGVPSRFSGSGSGTD<u>FT
LT</u>ISSLQPEDFGTYYCQHHYDTPYTFGQGTKLEIKRTVAAPSVFIFPPS
DEQLKSGTASVVCLLNNFYPREAKVQWKVDNALQSGNSQESVTEQDSKD
STYSLSSTLTLSKADYEKHKVYACEVTHQGLSSPVTKSFNRGEC*

>Light_Chain_DNA SEQ ID NO:12

ATGGGAAAAATGGCTTCTCTTTTTGCTACTTTCCTTGTTGTGTTGGTTA
GTCTTTCTCTAGCTAGTGAGAGTAGTGCTGACATTCAAATGACTCAATC
TCCGAGCAGCTTATCTGCCTCAGTAGGTGATAGAGTGACAATAACTTGC
AGGGCATCTCAAGATATTTCAAACTACCTGGAATGGTATCAGCAGAAAC
CAGGGAAAGCTCCAAAGCTCCTTGTTTACAATGCAAAGACATTGGCTGA
GGGTGTTCCTTCACGTTTCTCTGGAAGTGGGTCGGGCACCGACTTCACG
CTAACCATCAGTTCCCTTCAGCCTGAAGATTTTGGAACTTATTATTGTC
AACATCACTATGATACTCCCTACACATTTGGTCAAGGAACAAAGTTGGA
GATTAAAAGAACTGTTGCTGCTCCTTCTGTGTTCATTTTTCCACCATCT
GATGAACAACTGAAGAGCGGCACAGCGTCAGTCGTTTGTTTGTTGAATA
ATTTTTACCCTAGAGAGGCTAAAGTACAGTGGAAAGTTGATAATGCTCT
GCAGTCTGGAAATTCCCAAGAATCAGTAACAGAGCAAGATTCAAAGGAT
TCCACCTACAGTCTTTCGTCTACTTTAACATTGTCTAAAGCAGACTATG
AAAAGCACAAAGTGTATGCTTGTGAAGTTACTCATCAAGGTCTCAGCTC
GCCGGTGACAAAATCGTTCAACAGGGGTGAATGTTGA

Constant Ig domains can also contain one or more mutations that reduce or eliminate one or more effector function, e.g., binding to Fc receptors and complement activation (see, for example, Morrison, *Annu. Rev. Immunol.*, 10, pp. 239-65 (1992); Duncan and Winter (1988) *Nature* 332: 738-740; and Xu et al. (1994) *J Biol. Chem.* 269: 3469-3474). For example, mutations of amino acids corresponding to Leu 235 and Pro 331 of human IgG1 to Glu and Ser respectively, are provided. Such constructs are further described in U.S. Pat. No. 6,656,728.

Peptides can be used as a substantially pure preparation, such as wherein at least about 90% of the peptides in the preparation are the desired peptide. Compositions comprising at least about 50%, 60%, 70%, or 80% of the desired peptide may also be used. Peptides can be denatured or non-denatured and may be aggregated or non-aggregated as a result thereof.

Other antibody(ies) or portion(s) thereof that are encompassed herein are those that include modified amino acids. Exemplary peptides are derivative peptides that may be one modified by glycosylation, pegylation, phosphorylation or any similar process that retains at least one biological function of the peptide from which it was derived. Peptides may also comprise one or more non-naturally occurring amino acids. For example, nonclassical amino acids or chemical amino acid analogs can be introduced as a substitution or addition into peptides. Non-classical amino acids include, but are not limited to, the D-isomers of the common amino acids, 2,4-diaminobutyric acid, alpha-amino isobutyric acid, 4-aminobutyric acid, Abu, 2-amino butyric acid, gamma-Abu, epsilon-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, beta-alanine, fluoro-amino acids, designer amino acids such as beta-methyl amino acids, Calpha-methyl amino acids, Nalpha-methyl amino acids, and amino acid analogs in general. In some embodiments, substitution with selenomethionine can be useful (e.g., for X-ray diffraction analysis). Further, the amino acid can be D (dextrorotary) or L (levorotary). In other specific embodiments, branched versions of the peptides listed herein are provided, such as by substituting one or more amino acids within the sequence with an amino acid or amino acid analog with a free side chain capable of forming a peptide bond with one or more amino acids (and thus capable of forming a "branch"). Cyclical peptides are also contemplated.

Also included are peptide derivatives which are differentially modified during or after synthesis, such as by benzylation, glycosylation, acetylation, phosphorylation, amidation, pegylation, derivatization by known protecting/blocking groups, proteolytic cleavage, linkage to an antibody molecule or other cellular ligand, etc. In specific embodiments, the peptides are acetylated at the N-terminus and/or amidated at the C-terminus.

Also provided are derivatives of antibody or portions thereof, such as chemically modified peptides and peptidomimetics. Peptidomimetics are compounds based on, or derived from, peptides and proteins. Peptidomimetics can be obtained by structural modification of known peptide sequences using unnatural amino acids, conformational restraints, isosteric replacement, and the like. The subject peptidomimetics constitute the continuum of structural space between peptides and non-peptide synthetic structures; peptidomimetics may be useful, therefore, in delineating pharmacophores and in helping to translate peptides into nonpeptide compounds with the activity of the parent peptides.

Mimetopes of the antibody or portions thereof are included in the present disclosure. Such peptidomimetics can have such attributes as being non-hydrolyzable (e.g., increased stability against proteases or other physiological conditions which degrade the corresponding peptide), increased specificity and/or potency for stimulating cell differentiation. For illustrative purposes, peptide analogs can be generated using, for example, benzodiazepines (e.g., see Freidinger et al. in Peptides: Chemistry and Biology, G. R. Marshall ed., ESCOM Publisher: Leiden, Netherlands, 1988), substituted gamma lactam rings (Garvey et al. in Peptides: Chemistry and Biology, G. R. Marshall ed., ESCOM Publisher: Leiden, Netherlands, 1988, p 123), C-7 mimics (Huffman et al. in Peptides: Chemistry and Biology, G. R. Marshall ed., ESCOM Publisher: Leiden, Netherlands, 1988, p. 105), keto-methylene pseudopeptides (Ewenson et al. (1986) *J Med Chem* 29:295; and Ewenson et al. in Peptides: Structure and Function (Proceedings of the 9th American Peptide Symposium) Pierce Chemical Co. Rockland, Ill., 1985), 3-turn dipeptide cores (Nagai et al. (1985) *Tetrahedron Lett* 26:647; and Sato et al. (1986) *J Chem Soc Perkin Trans* 1: 1231), β-aminoalcohols (Gordon et al. (1985) *Biochem Biophys Res Commun* 126:419; and Dann et al. (1986) *Biochem Biophys Res Commun* 134:71), diaminoketones (Nataraj an et al. (1984) *Biochem Biophys Res Commun* 124:141), and methyleneamino-modified (Roark et al. in Peptides: Chemistry and Biology, G. R. Marshall ed., ESCOM Publisher: Leiden, Netherlands, 1988, p 134). Also, see generally, Session III: Analytic and synthetic methods, in Peptides: Chemistry and Biology, G. R. Marshall ed., ESCOM Publisher: Leiden, Netherlands, 1988).

In addition to a variety of side-chain replacements which can be carried out to generate peptidomimetics, the present disclosure specifically contemplates the use of conformationally restrained mimics of peptide secondary structure. Numerous surrogates have been developed for the amide bond of peptides. Frequently exploited surrogates for the amide bond include the following groups (i) trans-olefins, (ii) fluoroalkene, (iii) methyleneamino, (iv) phosphonamides, and (v) sulfonamides. Additionally, peptidomimetics based on more substantial modifications of the backbone of a peptide can be used. Peptidomimetics which fall in this category include (i) retro-inverso analogs, and (ii)N-alkyl glycine analogs (so-called peptoids). Furthermore, the methods of combinatorial chemistry can be used to produce peptidomimetics. For example, some embodiments of a so-called "peptide morphing" strategy focus on the random generation of a library of peptide analogs that comprise a wide range of peptide bond substitutes. In an exemplary embodiment, the peptidomimetic can be derived as a retro-inverso analog of the peptide. Such retro-inverso analogs can be made according to the methods known in the art, such as that described by the Sisto et al. U.S. Pat. No. 4,522,752. A retro-inverso analog can be generated as described, for example in PCT Publication No. WO 00/01720. A mixed peptide, such as one including some normal peptide linkages, can be generated. As a general guide, sites which are most susceptible to proteolysis are typically altered, with less susceptible amide linkages being optional for mimetic switching. The final product, or intermediates thereof, can be purified by HPLC.

The antibody or portions thereof (including amidated forms of the peptides) can be readily synthesized by automated solid phase procedures well known in the art. Techniques and procedures for solid phase synthesis are described in Solid Phase Peptide Synthesis: A Practical Approach, by E. Atherton and R. C. Sheppard, published by IRL, Oxford University Press, 1989. Alternatively, these peptides may be prepared by way of segment condensation, as described, for example, in Liu et al., *Tetrahedron Lett.* 37:933-936, 1996; Baca et al., *J. Am. Chem. Soc.* 117:1881-1887, 1995; Tam et al., *Int. J. Peptide Protein Res.* 45:209-216, 1995; Schnolzer and Kent, *Science* 256:221-225, 1992; Liu and Tam, *J. Am.* Chem. Soc. 116:4149-4153, 1994; Liu and Tam, *Proc. Natl. Acad. Sci. USA* 91:6584-6588, 1994; and Yamashiro and Li, *Int. J. Peptide Protein Res.* 31:322-334, 1988). Other methods useful for synthesizing peptides of the present disclosure are described in Nakagawa et al., *J. Am. Chem. Soc.* 107:7087-7092, 1985. Peptides of the disclosure can also be readily purchased from commercial suppliers of synthetic peptides. Such suppliers include, for example, Advanced ChemTech (Louisville, Ky.), Applied Biosystems (Foster City, Calif), Anaspec (San Jose, Calif.), and Cell Essentials (Boston, Mass.).

Polynucleotides Encoding the Antibody or portions thereof and Host Cells.

Polynucleotides encoding the antibody(ies) or portion(s) thereof disclosed herein are also provided. These polynucleotides include DNA, cDNA and RNA sequences which encode the peptide of interest. Silent mutations in the coding sequence result from the degeneracy (i.e., redundancy) of the genetic code, whereby more than one codon can encode the same amino acid residue. Thus, for example, leucine can be encoded by CTT, CTC, CTA, CTG, TTA, or TTG; serine can be encoded by TCT, TCC, TCA, TCG, AGT, or AGC; asparagine can be encoded by AAT or AAC; aspartic acid can be encoded by GAT or GAC; cysteine can be encoded by TGT or TGC; alanine can be encoded by GCT, GCC, GCA, or GCG; glutamine can be encoded by CAA or CAG; tyrosine can be encoded by TAT or TAC; and isoleucine can be encoded by ATT, ATC, or ATA. Tables showing the standard genetic code can be found in various sources (see, for example, Stryer, 1988, Biochemistry, 3.sup.rd Edition, W. H. 5 Freeman and Co., NY).

A nucleic acid encoding antibody(ies) or portion(s) thereof can be cloned or amplified by in vitro methods, such as the polymerase chain reaction (PCR), the ligase chain reaction (LCR), the transcription-based amplification system (TAS), the self-sustained sequence replication system (3SR) and the QP replicase amplification system (QB). For example, a polynucleotide encoding the protein can be isolated by polymerase chain reaction of cDNA using primers based on the DNA sequence of the molecule. A wide variety of cloning and in vitro amplification methodologies are well known to persons skilled in the art. PCR methods are described in, for example, U.S. Pat. No. 4,683,195; Mullis et al., ColdSpring Harbor Symp. *Quant. Biol.* 51:263, 1987; and Erlich, ed., PCR Technology, (Stockton Press, N Y, 1989). Polynucleotides also can be isolated by screening genomic or cDNA libraries with probes selected from the sequences of the desired polynucleotide under stringent hybridization conditions.

The polynucleotides encoding antibody(ies) or portion(s) thereof include a recombinant DNA which is incorporated into a vector in an autonomously replicating plasmid or virus or into the genomic DNA of a prokaryote or eukaryote, or which exists as a separate molecule (such as a cDNA) independent of other sequences. The nucleotides can be ribonucleotides, deoxyribonucleotides, or modified forms of either nucleotide. The term includes single and double forms of DNA.

In some embodiments, vectors are used for expression in yeast such as *S. cerevisiae* or *Kluyveromyces lactis*. Several promoters are known to be of use in yeast expression systems such as the constitutive promoters plasma membrane $H^+$-ATPase (PMA1), glyceraldehyde-3-phosphate dehydrogenase (GPD), phosphoglycerate kinase-1 (PGK1), alcohol dehydrogenase-1 (ADH1), and pleiotropic drug-resistant pump (PDR5). In addition, many inducible promoters are of use, such as GAL1-10 (induced by galactose), PHO5 (induced by low extracellular inorganic phosphate), and tandem heat shock HSE elements (induced by temperature elevation to 37° C.). Promoters that direct variable expression in response to a titratable inducer include the methionine-responsive MET3 and MET25 promoters and copper-dependent CUPi promoters. Any of these promoters may be cloned into multicopy (2) or single copy (CEN) plasmids to give an additional level of control in expression level. The plasmids can include nutritional markers (such as URA3, ADE3, HIS1, and others) for selection in yeast and antibiotic resistance (AMP) for propagation in bacteria. Plasmids for expression on *K. lactis* are known, such as pKLAC1. Thus, in one example, after amplification in bacteria, plasmids can be introduced into the corresponding yeast auxotrophs by methods similar to bacterial transformation. The polynucleotides can also be designed to express in insect cells.

The antibody(ies) or portion(s) thereof can be expressed in a variety of yeast strains. For example, seven pleiotropic drug-resistant transporters, YOR1, SNQ2, PDR5, YCF1, PDR10, PDR11, and PDR15, together with their activating transcription factors, PDR1 and PDR3, have been simultaneously deleted in yeast host cells, rendering the resultant strain sensitive to drugs. Yeast strains with altered lipid composition of the plasma membrane, such as the erg6 mutant defective in ergosterol biosynthesis, can also be utilized. Proteins that are highly sensitive to proteolysis can be expressed in a yeast lacking the master vacuolar endopeptidase Pep4, which controls the activation of other vacuolar hydrolases. Heterologous expression in strains carrying temperature-sensitive (ts) alleles of genes can be employed if the corresponding null mutant is inviable.

Viral vectors can also be prepared encoding the antibody(ies) or portion(s) thereof disclosed herein. A number of viral vectors have been constructed, including polyoma, SV40 (Madzak et al., 1992, *J. Gen. Virol.*, 73:15331536), adenovirus (Berkner, 1992, Cur. Top. *Microbiol. Immunol.*, 158:39-6; Berliner et al., 1988, *Bio Techniques*, 6:616-629; Gorziglia et al., 1992, *J. Virol.*, 66:4407-4412; Quantin et al., 1992, *Proc. Natl. Acad. Sci. USA*, 89:2581-2584; Rosenfeld et al., 1992, *Cell*, 68:143-155; Wilkinson et al., 1992, *Nucl. Acids Res.*, 20:2233-2239; Stratford-Perricaudet et al., 1990, *Hum. Gene Ther.*, 1:241-256), vaccinia virus (Mackett et al., 1992, *Biotechnology*, 24:495-499), adeno-associated virus (Muzyczka, 1992, *Curr. Top. Microbiol. Immunol.* 158:91-123; On et al., 1990, *Gene*, 89:279-282), herpes viruses including HSV and EBV (Margolskee, 1992, *Curr. Top. Microbiol. Immunol.*, 158:67-90; Johnson et al., 1992, *J. Virol.*, 66:29522965; Fink et al., 1992, *Hum. Gene Ther.* 3:11-19; Breakfield et al., 1987, *Mol. Neurobiol.*, 1:337-371; Fresse et al., 1990, *Biochem. Pharmacol.* 40:2189-2199), Sindbis viruses (Herweijer et al., 1995, *Human Gene Therapy* 6:1161-1167; U.S. Pat. Nos. 5,091,309 and 5,217,879), alphaviruses (Schlesinger, 1993, *Trends Biotechnol.* 11:18-22; Frolov et al., 1996, *Proc. Natl. Acad. Sci. USA* 93:11371-11377) and retroviruses of avian (Brandyopadhyay et al., 1984, *Mol. Cell Biol.*, 4:749-754; Petropouplos et al., 1992, *J. Virol.*, 66:3391-3397), murine (Miller, 1992, *Curr. Top. Microbiol. Immunol.*, 158:1-24; Miller et al., 1985, *Mol. CellBiol.*, 5:431-437; Sorge et al., 1984, *Mol. CellBiol.*, 4:1730-1737; Mann et al., 1985, *J. Virol.*, 54:401-407), and human origin (Page et al., 1990, *J. Virol.*, 64:5370-5276; Buchschalcher et al., 1992, *J. Virol.*, 66:2731-2739). Baculovirus (*Autographa californica* multinuclear polyhedrosis virus; AcMNPV) vectors are also known in the art, and may be obtained from commercial sources (such as PharMingen, San Diego, Calif.; Protein Sciences Corp., Meriden, Conn.; Stratagene, La Jolla, Calif).

Thus, in some embodiments, the polynucleotide encoding antibody(ies) or portion(s) thereof are included in a viral vector. Suitable vectors include retrovirus vectors, orthopox vectors, avipox vectors, fowlpox vectors, capripox vectors, suipox vectors, adenoviral vectors, herpes virus vectors, alpha virus vectors, baculovirus vectors, Sindbis virus vectors, vaccinia virus vectors and poliovirus vectors. Specific exemplary vectors are poxvirus vectors such as vaccinia virus, fowlpox virus and a highly attenuated vaccinia virus (MVA), adenovirus, baculovirus and the like.

Pox viruses of use include orthopox, suipox, avipox, and capripox virus. Orthopox include vaccinia, ectromelia, and raccoon pox. One example of an orthopox of use is vaccinia. Avipox includes fowlpox, canary pox and pigeon pox. Capripox include goatpox and sheeppox. In one example, the suipox is swinepox. Examples of pox viral vectors for expression as described for example, in U.S. Pat. No. 6,165,460, which is incorporated herein by reference. Other viral vectors that can be used include other DNA viruses such as herpes virus and adenoviruses, and RNA viruses such as retroviruses and polio.

Suitable vectors are disclosed, for example, in U.S. Pat. No. 6,998,252, which is incorporated herein by reference. In one example, a recombinant poxvirus, such as a recombinant vaccinia virus is synthetically modified by insertion of a chimeric gene containing vaccinia regulatory sequences or DNA sequences functionally equivalent thereto flanking DNA sequences which in nature are not contiguous with the flanking vaccinia regulatory DNA sequences that encode the antibody(ies) or portion(s) thereof. The recombinant virus containing such a chimeric gene is effective at expressing the antibody(ies) or portion(s) thereof. In one example, the vaccine viral vector comprises (A) a segment comprised of (i) a first DNA sequence encoding the antibody(ies) or portion(s) thereof and (ii) a poxvirus promoter, wherein the poxvirus promoter is adjacent to and exerts transcriptional control over the DNA sequence encoding the antibody(ies) or portion(s) thereof, and, flanking said segment, (B) DNA from a nonessential region of a poxvirus genome. The viral vector can encode a selectable marker. In one example, the poxvirus includes, for example, a thymidine kinase gene (see U.S. Pat. No. 6,998,252, which is incorporated herein by reference).

Poxviral vectors that encode a fusion protein that includes: an extensin signal peptide and the antibody(ies) or portion(s) thereof, under the control of at least one expression control element operationally linked to the nucleic acid sequence encoding the antibody(ies) or portion(s) thereof. The expression control elements are inserted in the poxviral vector to control and regulate the expression of the nucleic acid sequence. Examples of expression control elements of use in these vectors includes, but is not limited to, lac system, operator and promoter regions of phage lambda, yeast promoters and promoters derived from polyoma, adenovirus, retrovirus or SV40. Additional operational elements include, but are not limited to, leader sequence, termination codons, polyadenylation signals and any other sequences necessary for the appropriate transcription and subsequent translation of the nucleic acid sequence encoding the antibody(ies) or portion(s) thereof in the host system. The expression vector can contain additional elements necessary for the transfer and subsequent replication of the expression vector containing the nucleic acid sequence in the host system. Examples of such elements include, but are not limited to, origins of replication and selectable markers. It will further be understood by one skilled in the art that such vectors are easily constructed using conventional methods (Ausubel et al., (1987) in *Current Protocols in Molecular Biology*, John Wiley and Sons, New York, N.Y.) and are commercially available.

Basic techniques for preparing recombinant DNA viruses containing a heterologous DNA sequence encoding the antibody(ies) or portion(s) thereof, are known in the art. Such techniques involve, for example, homologous recombination between the viral DNA sequences flanking the DNA sequence in a donor plasmid and homologous sequences present in the parental virus (Mackett et al., 1982, *Proc. Natl. Acad. Sci. USA* 79:7415-7419). In particular, recombinant viral vectors such as a poxviral vector can be used in delivering the gene. The vector can be constructed for example by steps known in the art, such as steps analogous to the methods for creating synthetic recombinants of the fowlpox virus described in U.S. Pat. No. 5,093,258, incorporated herein by reference. Other techniques include using a unique restriction endonuclease site that is naturally present or artificially inserted in the parental viral vector to insert the heterologous DNA.

DNA sequences encoding the antibody(ies) or portion(s) thereof can be expressed in vitro by DNA transfer into a suitable host cell. The cell may be prokaryotic or eukaryotic. The term also includes any progeny of the subject host cell. It is understood that all progeny may not be identical to the parental cell since there may be mutations that occur during replication. Methods of stable transfer, meaning that the foreign DNA is continuously maintained in the host, are known in the art.

As noted above, a polynucleotide sequence encoding the antibody(ies) or portion(s) thereof can be operatively linked to expression control sequences. An expression control sequence operatively linked to a coding sequence is ligated such that expression of the coding sequence is achieved under conditions compatible with the expression control sequences. The expression control sequences include, but are not limited to, appropriate promoters, enhancers, transcription terminators, a start codon (i.e., ATG) in front of a protein-encoding gene, splicing signal for introns, maintenance of the correct reading frame of that gene to permit proper translation of mRNA, and stop codons.

Hosts cells can include microbial, yeast, insect and mammalian host cells.

Methods of expressing DNA sequences having eukaryotic or viral sequences in prokaryotes are well known in the art. Non-limiting examples of suitable host cells include bacteria, archea, insect, fungi (for example, yeast), plant, and animal cells (for example, mammalian cells, such as human). Exemplary cells of use include *Escherichia coli, Bacillus subtilis, Saccharomyces cerevisiae, Salmonella typhimurium*, SF9 cells, C129 cells, 293 cells, *Neurospora*, and immortalized mammalian myeloid and lymphoid cell lines. Techniques for the propagation of mammalian cells in culture are well-known (see, Jakoby and Pastan (eds), 1979, *Cell Culture. Methods in Enzymology*, volume 58, Academic Press, Inc., Harcourt Brace Jovanovich, N.Y.). Examples of commonly used mammalian host cell lines are VERO and HeLa cells, CHO cells, and WI38, BHK, and COS cell lines, although cell lines may be used, such as cells designed to provide higher expression desirable glycosylation patterns, or other features. As discussed above, techniques for the transformation of yeast cells, such as polyethylene glycol transformation, protoplast transformation and gene guns are also known in the art (see Gietz and Woods, *Meth Enzymol* 350: 87-96, 2002).

Transformation of a host cell with recombinant DNA can be carried out by conventional techniques as are well known to those skilled in the art. Where the host is prokaryotic, such as, but not limited to, *E. coli*, competent cells which are capable of DNA uptake can be prepared from cells harvested after exponential growth phase and subsequently treated by the $CaCl_2$) method using procedures well known in the art. Alternatively, $MgCl_2$ or RbCl can be used. Transformation can also be performed after forming a protoplast of the host cell if desired, or by electroporation.

When the host is a eukaryote, such methods of transfection of DNA as calcium phosphate coprecipitates, conventional mechanical procedures such as microinjection, electroporation, insertion of a plasmid encased in liposomes, or virus vectors can be used. Eukaryotic cells can also be co-transformed with polynucleotide sequences encoding the antibody(ies) or portion(s) thereof, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, Eukaryotic Viral Vectors, Cold Spring Harbor Laboratory, Gluzman ed., 1982).

The antibody(ies) or portion(s) thereof and variants also can be produced in plants. For example, polypeptides can be expressed in plants using the IBIOLAUNCH™ gene expression platform (iBio, Inc., Newark, DE) as described in, for example, U.S. Pat. No. 7,491,509 (which is incorporated herein by reference in its entirety). The IBIOLAUNCH™ platform can be used to produce high levels of target proteins in non-transgenic plants. This platform can have benefits over methods utilizing animal cells, or microbes, and over systems that require transgenic plants.

To use this system, a desired gene is cloned into an IBIOLAUNCH™ vector, which is introduced into the leaves of plants (e.g., by automated vacuum infiltration). The vector is allowed to spread to cells in the stems and leaves, where the desired protein is expressed at extremely high levels over the next 4-7 days. The green plant material is then harvested and the protein product purified. The entire IBIOLAUNCH™ gene expression process can be repeated for a different protein with a new plant crop in the same facility, making this technology the most flexible and fastest way to produce protein drugs and vaccines. In one example, the light and heavy chains are on separate vector for infiltration, but can be expressed on the same vector.

A plant expression vector system can include one or more viral vector components. A wide variety of viruses are known that infect various plant species, and can be employed for polynucleotide expression. Families of viruses that infect plants include, without limitation, Tobamoviridae, Caulimoviridae (dsDNA), Geminiviridae (ssDNA), Reoviridae and Partitiviridae (dsRNA), and Rhabdoviridae, Bunyaviridae, Bromoviridae, and Comoviridae (ssRNA). Additional information can be found, for example, in "The Classification and Nomenclature of Viruses, Sixth Report of the International Committee on Taxonomy of Viruses" (Ed. Murphy et al.), Springer Verlag: New York, 1995, the entire contents of which are incorporated herein by reference (see also, Grierson et al., Plant Molecular Biology, Blackie, London, pp. 126-146, 1984; Gluzman et al., Communications in Molecular Biology: Viral Vectors, Cold Spring Harbor Laboratory, NY, pp. 172-189, 1988; and Mathew, Plant Viruses Online.

In order to successfully establish either a local (intraleaf) or systemic infection a virus must be able to replicate. Many viruses contain genes encoding one or more proteins that participate in the replication process (referred to herein as replication proteins or replicase proteins). For example, many RNA plant viruses encode an RNA polymerase. Additional proteins also may be required, such as helicase or methyltransferase protein(s). The viral genome may contain various sequence components in addition to functional genes encoding replication proteins, which are also required for or facilitate replication.

Any virus that infects plants can be used to prepare a viral vector or vector system in accordance with the methods described herein. ssRNA viruses can be particularly useful, especially those with a (+)-stranded genome. Techniques and reagents for manipulating the genetic material present in such viruses include those that are well known in the art. Typically, for example, a DNA copy of the viral genome is prepared and cloned into a microbial vector (e.g., a bacterial vector). Certain ssDNA viruses, including geminiviruses, are particularly useful. It will be appreciated that in general the vectors and viral genomes may exist in RNA or DNA form. In addition, where reference is made to a feature such as a genome or portion thereof of an RNA virus, which is present within a DNA vector, it is to be understood that the feature is present as the DNA copy of the RNA form.

Viruses of a number of different types may be used. Suitable viruses include, for example, members of the Bromoviridae (e.g., bromoviruses, alfamoviruses, ilarviruses) and Tobamoviridae. Useful virus species include, for example, Alfalfa Mosaic Virus (AlMV), Apple Chlorotic Leaf Spot Virus, Apple Stem Grooving Virus, Barley Stripe Mosaic Virus, Barley Yellow Dwarf Virus, Bean Yellow Dwarf Virus, Beet Yellow Virus, Broad Bean Mottle Virus, Broad Bean Wilt Virus, Brome Mosaic Virus (BMV), Carnation Latent Virus, Carnation Mottle Virus, Carnation Ringspot Virus, Carrot Mottle Virus, Cassava Latent Virus (CLV), Cowpea Chlorotic Mottle Virus, Cowpea Mosaic Virus (CPMV), Cucumber Green Mottle Mosaic Virus, Cucumber Mosaic Virus, Lettuce Infectious Yellow Virus, Maize Chlorotic Mottle Virus, Maize Rayado Fino Virus, Maize Streak Virus (MSV), Parsnip Yellow Fleck Virus, Pea Enation Mosaic Virus, Potato Virus X, Potato Virus Y, Raspberry Bushy Dwarf Virus, Rice Necrosis Virus (RNV), Rice Stripe Virus, Rice Tungro Spherical Virus, Ryegrass Mosaic Virus, Soil-borne Wheat Mosaic Virus, Southern Bean Mosaic Virus, Tobacco Etch Virus (TEV), Tobacco Mosaic Virus (TMV), Tobacco Necrosis Virus, Tobacco Rattle Virus, Tobacco Ring Spot Virus, Tomato Bushy Stunt Virus, Tomato Golden Mosaic Virus (TGMV), and Turnip Yellow Mosaic Virus (TYMV).

Elements of these plant viruses are genetically engineered according to known techniques (see, for example, (see, for example, Sambrook et al., Molecular Cloning, $2^{nd}$ Edition, Cold Spring Harbor Press, N Y, 1989; Clover et al., Molecular Cloning, IRL Press, Oxford, 1985; Dason et al., *Virology*, 172:285-292, 1989; Takamatsu et al., *EMBO J.* 6:307-311, 1987; French et al., *Science* 231: 1294-1297, 1986; Takamatsu et al., *FEBS Lett.* 269:73-76, 1990; Yusibov and Loesch-Fries, *Virology*, 208(1): 405-7, 1995; and Spitsin et al., Proc. *P Natl. Acad. Sci. USA*, 96(5): 2549-53, 1999) to generate viral vectors for use in plant production of polypeptides of interest, including the antibody(ies) or portion(s) thereof provided herein. At least two vectors are employed, one or both of which are incapable of systemic infection, but which together provide all functions needed to support systemic infection of at least one of the vectors and allow expression of a polynucleotide of interest throughout the plant. Thus, the viral components can complement each other in trans to provide systemic infection capability.

In particular, a producer vector is prepared. This vector includes a polynucleotide of interest (e.g., a polynucleotide encoding the antibody(ies) or portion(s) thereof) under control of regulatory sequences that direct expression in the relevant plant host. In some embodiments, the polynucleotide is placed under control of a viral promoter, for example the CP promoter. For instance, it can be desirable to replace the natural viral CP gene with the polynucleotide of interest. The producer vector lacks one or more components required for systemic movement. For example, the producer vector may not contain sequences sufficient for expression of functional CP (e.g., a CP gene), but may include a gene encoding a cell-to-cell movement protein. The producer vector may contain one or more sequence elements (e.g., an origin of assembly) that may be required in cis to facilitate spread of the virus when present in cis. For example, the producer vector may contain an origin of assembly that is needed for or facilitates activity of a CP, either from the same type of virus as the producer virus or from another virus. Such sequence elements may comprise a recognition site for a CP. In other embodiments, the producer vector may lack sequences sufficient for expression of functional MP and/or replicase proteins. In these embodiments, the producer vector may or may not lack sequences sufficient for expression of functional CP.

A carrier vector also is prepared. This vector complements the producer vector, such that it provides components needed for systemic infection that are missing in the producer vector. For example, certain carrier vectors include a functional coat protein encoding component. These carrier vectors are suitable for complementing a producer vector that lacks a functional coat protein encoding component. The carrier vector may lack at least one viral component (e.g., a gene encoding a replicase or movement protein) required for successful systemic infection of a plant, provided that such component is not also absent in the producer vector. The carrier vector may include a polynucleotide of interest (which may be the same as or different from the polynucleotide of interest in the producer vector). In such cases it may be desirable to use a carrier vector that is defective for systemic infection, e.g., because it lacks one or more necessary cis-acting sequences, in order to minimize spread of the recombinant carrier vector to non-target plants.

The carrier vector may (but need not) include a cell-to-cell movement component (e.g., a gene encoding a cell-to-cell movement protein or a noncoding component that is needed for cell-to-cell movement) and/or may lack one or more replicase protein encoding components. In embodiments in which the carrier vector does not include a cell-to-cell movement component (e.g., a functional MP encoding portion), such a component should be included in the producer vector.

A complete vector set includes all components necessary for successful systemic viral infection and expression of a polynucleotide of interest. The term "component" is intended to include both protein coding sequences and non-coding sequences such as cis-acting sequences (e.g., promoters, origin of assembly, portions corresponding to untranslated regions in mRNA). Different vectors, or vector elements, may be derived from different plant viruses. In fact, it may be desirable to prepare vectors from elements of different viruses in order to take advantage of different viral characteristics (e.g., host range, promoter activity level, virion dimensions, etc.).

In some embodiments, a producer vector is provided that includes a polynucleotide of interest, a replicase gene, and a movement protein gene, but lacks a functional coat protein encoding component, and a carrier vector is provided that expresses a coat protein gene. For example, a producer vector may include a TMV-based vector in which the TMV CP coding sequence has been replaced by a polynucleotide of interest, under control of the TMV CP promoter. This producer vector is unable to move systemically. A wild type AlMV vector can serve as the carrier vector. The AlMV vector contains a functional coat protein encoding component. Co-infection with both producer and carrier vectors allows the CP produced from the AlMV vector CP coding sequence to complement the TMV-based vector, resulting in systemic movement of the TMV-based vector and expression of the polynucleotide in leaves that were not initially infected. Alternately, an AlMV-based vector in which one or more viral components other than those required for expression of AlMV CP has been removed can be used (e.g., an AlMV-based vector lacking functional MP or replication protein coding components), provided that functional CP coding sequences and an operably linked promoter are present. The CP can be from A1MV or from another virus.

In some embodiments, the CP allows for systemic movement of the carrier vector, while in other embodiments a CP is selected that does not allow for systemic movement of the carrier vector but does allow for systemic movement of the producer vector. In those embodiments in which the carrier vector lacks one or more of the viral components other than those required for expression of A1MV CP, the producer vector may complement the carrier vector. For example, the producer vector may supply a component such as a functional MP or replicase protein coding sequence that allows for cell-to-cell movement or replication, respectively, of the carrier vector (and, in some cases, also the producer vector). It will be appreciated that where either the producer or the carrier is lacking a replication protein encoding component (e.g., a functional RNA polymerase coding component) and the other vector (carrier or producer, respectively) supplies the missing component, it will often be desirable to insert a promoter (e.g., a genomic promoter) from the vector that supplies the functional replication component into the vector lacking the functional replication protein coding component in order to achieve effective trans-complementation of replication function.

Another example of a useful viral vector system includes a producer vector in which a polynucleotide of interest is inserted into an A1MV vector, replacing the native A1MV CP encoding component. The polynucleotide of interest is placed under control of the A1MV CP promoter. This producer vector is incapable of systemic infection since it lacks CP but is able to replicate and move cell-to-cell within an infected leaf. The system also includes a cauliflower mosaic virus (CMV)-based carrier vector in which an A1MV CP encoding portion, with or without the A1MV CP 3' UTR is inserted into a CMV vector, replacing the CMV CP encoding component found in the genome of naturally occurring CMV. The A1MV CP encoding component is placed under control of the CMV CP promoter. This vector expresses A1MV CP. Co-infection with the producer and carrier vectors allows CP expressed from the carrier vector to trans-complement the producer vector's lack of functional CP encoding components, allowing systemic movement of the producer vector. The A1MV CP also allows systemic movement of the carrier vector.

In some embodiments, it can be desirable to insert a portion of coding or noncoding sequence from the carrier vector into the producer vector, or vice versa. For example, certain sequences may enhance replication or facilitate cell-to-cell or long distance movement. In particular, certain sequences may serve as recognition sites for formation of a complex between a viral transcript and a CP (e.g., an origin of assembly). In such a case, if systemic movement of a first viral vector is to be achieved using CP provided in trans from a second viral vector, it may be desirable to insert such sequences from the second viral vector that facilitate activity of the CP into the first viral vector. Such sequences may include, for example, part or all of a viral transcript 3' UTR. In some cases, part or all of the RNA3 3' UTR of A1MV is inserted into a different viral vector, e.g., a TMV-based vector. Including this component in the TMV-based vector facilitates the ability to A1MV CP to trans-complement a TMV-based vector that lacks a functional TMV CP encoding portion. It will be appreciated that this general principle may be applied to any viral vector system comprising trans-complementing vectors, e.g., trans-complementing producer and carrier vector systems.

As will be appreciated by those of ordinary skill in the art, so long as a vector set includes a producer vector that is incapable of systemic viral infection (e.g., lacking one or more functional replication protein, movement protein, or coat protein encoding components) and a carrier vector that provides the function(s) lacking in the producer vector, that set is appropriate for use in accordance with the methods described herein. In some embodiments, no individual vector is capable of systemic viral infection but, as a set, one or both of the vectors is/are competent for such infection and expression of the polynucleotide of interest. Such a system can offer a number of advantages. For example, it will be appreciated that if the producer vector infects a plant in the absence of the carrier vector, no systemic infection will result. This diminishes the risk that the polynucleotide of interest will be expressed in unintended (non-target) plants, even of the same species as the target plant. In particular, if the carrier vector is not competent for replication or cell-to-cell movement (because it lacks a component required for replication or cell-to-cell movement) or if it is incompetent for systemic infection (e.g., because it lacks a cis-acting sequence such as an origin of assembly that is required for long distance movement), the likelihood that both producer and carrier vectors will co-infect an unintended plant host are greatly reduced.

Generally, in order to preserve viral function and also simply for ease of genetic manipulation, vectors are prepared by altering an existing plant virus genome (e.g., by removing particular genes and/or by disrupting or substituting particular sequences so as to inactivate or replace them). In such circumstances, the vectors will show very high sequence identity with natural viral genomes. Of course, completely novel vectors may also be prepared, for example, by separately isolating individual desired genetic elements and linking them together, optionally with the inclusion of additional elements. Also, it should be noted that where a particular vector is said to lack a given gene, protein, or activity (e.g., the producer vector lacks a coat protein gene), it is sufficient if no such protein or activity is expressed from the vector under conditions of infection, even though the vector may still carry the relevant coding sequence. In general, however, it is typically desirable to remove the relevant coding sequences from the vector.

Analogously, when a vector is said to affirmatively express a particular protein or activity, it is not necessary that the relevant gene be identical to the corresponding gene found in nature. For instance, it has been found that the coat protein can sometimes tolerate small deletions (see, for example, WO 00/46350, which is incorporated herein by reference in its entirety). So long as the protein is functional, it may be used in accordance with the methods described herein. Very high sequence identity with the natural protein, however, is generally considered to be most useful. For instance, large deletions (e.g., greater than about 25 amino acids) generally should be avoided. Typically, viral proteins will show at least 50% (e.g., 60%, 70%, 80%, 85%, 90%, 91%, 92%, 93%, 94%, 95%, 96%, 97%, 98%, or 99%) sequence identity with the corresponding natural viral protein. More particularly, the viral protein typically should have 100% identity with critical functional portions (typically of at least several amino acids, often of at least 10, 20, 30, 40, 50 or more amino acids) of the relevant natural viral protein.

It is noted that in the case of many proteins, a number of amino acid changes can be made without significantly affecting the functional activity and/or various other properties of the protein such as stability, etc. In particular, many proteins tolerate conservative amino acid changes—the substitution of an amino acid with a different amino acid having similar properties, without significant reduction in activity. Conservative amino acid substitution is well known in the art and represents one approach to obtaining a polypeptide having similar or substantially similar properties to those of a given polypeptide while altering the amino acid sequence. In general, amino acids have been classified and divided into groups according to (1) charge (positive, negative, or uncharged); (2) volume and polarity; (3) Grantham's physico-chemical distance; and combinations of these. See, e.g., Zhang, *J. Mol. Evol.*, 50:56-68, 2000; Grantham, *Science*, 85:862-864, 1974; Dagan et al., *Mol. Biol. Evol.*, 19(7), 1022-1025, 2002; Biochemistry, 4th Ed., Stryer et al., W. Freeman and Co., 1995; and U.S. Pat. No. 6,015,692. For example, amino acids may be divided into the following categories based on volume and polarity: special (C); neutral and small (A, G, P, S, T); polar and relatively small (N, D, Q, E), polar and relatively large (R, H, K), nonpolar and relatively small (I, L, M, V), and nonpolar and relatively large (F, W, Y). A conservative amino acid substitution may be defined as one that replaces one amino acid with an amino acid in the same group. Thus a variety of functionally equivalent proteins can be derived by making one or more conservative amino acid substitutions in a given viral protein.

Any plant susceptible to viral infection may be utilized in accordance with the methods described herein. In general, it will often be desirable to utilize plants that are amenable to growth under defined conditions, for example in a greenhouse and/or in aqueous systems. It also may be desirable to select plants that are not typically consumed by human beings or domesticated animals and/or are not typically part of the human food chain, so that they may be grown outside without concern that the expressed polynucleotide may be undesirably ingested. In other embodiments, however, it will be desirable to employ edible plants.

Often, certain desirable plant characteristics will be determined by the particular polynucleotide to be expressed. To give but a few examples, when the polynucleotide encodes a protein to be produced in high yield (as will often be the case, for example, when therapeutic proteins are to be expressed), it will often be desirable to select plants with relatively high biomass (e.g., tobacco, which has the additional advantages that it is highly susceptible to viral infection, has a short growth period, and is not in the human food chain). Where the polynucleotide encodes a protein whose full activity requires (or is inhibited by) a particular post-translational modification, the ability (or inability) of certain plant species to accomplish the relevant modification (e.g., a particular glycosylation) may direct selection.

In some embodiments, crop plants, or crop-related plants, are utilized. In some embodiments, edible plants are utilized.

Plants suitable for use in accordance with the methods described herein include, without limitation, Angiosperms, Bryophytes (e.g., Hepaticae, Musci, etc.), Pteridophytes (e.g., ferns, horsetails, lycopods), Gymnosperms (e.g., conifers, cycase, Ginko, Gnetales), and Algae (e.g., Chlorophyceae, Phaeophyceae, Rhodophyceae, Myxophyceae, Xanthophyceae, and Euglenophyceae). In some embodiments, members of the family Leguminosae (Fabaceae; e.g., pea, alfalfa, soybean); Gramineae (Poaceae; e.g., corn, wheat, rice); Solanaceae, particularly of the genus *Lycopersicon* (e.g., tomato), *Solanum* (e.g., potato, eggplant), Capsium (e.g., pepper), or *Nicotiana* (e.g., tobacco); Umbelliferae, particularly of the genus *Daucus* (e.g., carrot), *Apium* (e.g., celery), or Rutaceae (e.g., oranges); Compositae, particularly of the genus *Lactuca* (e.g., lettuce); and Brassicaceae (Cruciferae), particularly of the genus *Brassica* or *Sinapis*, can be particularly useful. For example, useful Brassicaceae family members include *Brassica campestris*, *B. carinata, B. juncea, B. napus, B. nigra, B. oleraceae*, B. tournifortii, *Sinapis alba*, and *Raphanus sativus*. exemplary *Nicotiana* plant include those taught by Schneider et al. (*Plant Physiology and Biochemistry* 92 (2015), 39-47), relevant portions incorporated herein by reference, such as GalT-dXT/FT *Nicotiana benthamiana* plants with modified N-glycosylation, or C105 dXT/FT *Nicotiana benthamiana* plants with modified N-glycosylation.

The expression system may be employed to infect, and/or to express a polynucleotide in plants at any stage of development including, for example, mature plants, seedlings, sprouts, and seeds. The system may be employed to infect any part of a plant (e.g., roots, leaves, stems, etc.). In some embodiments, the system is used to infect sprouts. Generally, a plant is considered to be a sprout when it is a seedling that does not require external nutrients or energy in the form of light or heat beyond what is required to achieve normal germination temperatures. Often, a seedling that is less than two weeks old, and typically less than 10 days old, is considered to be a sprout.

In general, viral vectors may be delivered to plants according to known techniques. For example, the vectors themselves may be directly applied to plants (e.g., via abrasive inoculations, mechanized spray inoculations, vacuum infiltration, particle bombardment, or electroporation). Alternatively, virions may be prepared (e.g., from already infected plants), and may be applied to other plants according to known techniques.

As noted above, in some embodiments, viral vectors are applied to sprouts (e.g., through infiltration or mechanical inoculation [spray]).

Where infection is to be accomplished by direct application of a viral genome to a plant, any available technique may be used to prepare the genome. For example, many viruses that are usefully employed in accordance with the methods described herein have ssRNA genomes. ssRNA may be prepared by transcription of a DNA copy of the genome, or by replication of an RNA copy, either in vivo or in vitro. Given the readily availability of easy-to-use in vitro transcription systems (e.g., SP6, T7, reticulocyte lysate, etc.), and also the convenience of maintaining a DNA copy of an RNA vector, it is expected that ssRNA vectors will often be prepared by in vitro transcription, particularly with T7 or SP6 polymerase.

In some embodiments, it will be desirable to isolate polynucleotide expression products from the plant tissues that express them. It also may be desirable to formulate such isolated products for their intended use (e.g., as a pharmaceutical or diagnostic agents, as reagents, etc.). In other embodiments, it will be desirable to formulate the products together with some or all of the plant tissues that express them.

To isolate the expression product from some or all of the plant tissue that expresses it, any available purification techniques may be employed. Those of ordinary skill in the art are familiar with a wide range of fractionation and separation procedures (see, for example, Scopes et al., Protein Purification: Principles and Practice, $3^{rd}$ Ed., Janson et al., "Protein Purification: Principles, High Resolution Methods, and Applications," Wiley-VCH, 1998; Springer-Verlag, NY, 1993; and Roe, Protein Purification Techniques, Oxford University Press, 2001, each of which is incorporated herein by reference in its entirety). Often, it will be desirable to render the product more than about 50%, preferably more than about 60%, 70%, 80%, 85%, 90%, 91%, 92%, 93%, 94%, 95%, 96%, 97%, 98%, or 99% pure.

To formulate the product together with the plant material, it will often be desirable to have utilized a plant that is not toxic to the relevant recipient (e.g., a human or other animal). Relevant plant tissue (e.g., leaves) may simply be harvested and processed according to techniques known in the art, with due consideration to maintaining activity of the expressed product. In some embodiments, the polynucleotide can be expressed in an edible plant (and, specifically in edible portions of the plant) so that the material can subsequently be eaten. For example, where the polynucleotide encodes a nutritionally relevant protein or a therapeutic protein that is active after oral delivery (when properly formulated), it may be useful to produce the protein in an edible plant portion, and to formulate the expressed polynucleotide for oral delivery together with some or all of the plant material with which the polynucleotide was expressed.

Where the polynucleotide encodes or produces a therapeutic agent, it may be formulated according to known techniques. For example, an effective amount of a pharmaceutically active product can be formulated together with one or more organic or inorganic, liquid or solid, pharmaceutically suitable carrier materials. A pharmaceutically active product may be employed in dosage forms such as tablets, capsules, troches, dispersions, suspensions, solutions, capsules, creams, ointments, aerosols, powder packets, liquid solutions, solvents, diluents, surface active agents, isotonic agents, thickening or emulsifying agents, preservatives, and solid bindings, as long as the biological activity of the protein is not destroyed by such dosage form.

Materials that can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening agents, flavoring agents, and perfuming agents, preservatives, and antioxidants can also be present in the composition, according to the judgment of the formulator (see also Remington's Pharmaceutical Sciences, Fifteenth Edition, E. W. Martin, Mack Publishing Co., Easton PA, 1975). For example, a polynucleotide expression product may be provided as a pharmaceutical composition by means of conventional mixing granulating dragee-making, dissolving, lyophilizing, or similar processes.

In some embodiments, it may be useful to prolong the effect of a pharmaceutical preparation by slowing the absorption of the pharmaceutically active product (e.g., protein) that is subcutaneously or intramuscularly injected. This may be accomplished by the use of a liquid suspension of crystalline or amorphous material with poor water solubility. The rate of absorption of the product then depends upon its rate of dissolution, which in turn, may depend upon size and form. Alternatively, delayed absorption of a parenterally administered product is accomplished by dissolving or suspending the product in an oil vehicle. Injectable depot forms are made by forming microencapsule matrices of the protein in biodegradable polymers such as polylactide-polyglycolide. Depending upon the ratio of product to polymer and the nature of the particular polymer employed, the rate of release can be controlled. Examples of other biodegradable polymers include poly(orthoesters) and poly (anhydrides). Depot injectable formulations may be prepared by entrapping the product in liposomes or microemulsions, which are compatible with body tissues.

Enterically administered preparations of pharmaceutically active products may be introduced in solid, semi-solid, suspension or emulsion form and may be compounded with any pharmaceutically acceptable carriers, such as water, suspending agents, and emulsifying agents. The expression products may also be administered by means of pumps or sustained-release forms, especially when administered as a preventive measure, so as to prevent the development of disease in a subject or to ameliorate or delay an already established disease.

Pharmaceutically active products, optionally together with plant tissue, can be particularly well suited for oral administration as pharmaceutical compositions. Harvested plant material may be processed in any of a variety of ways (e.g., air drying, freeze drying, extraction etc.), depending on the properties of the desired therapeutic product and its desired form. In preferred embodiments, such compositions as described above are ingested orally alone or ingested together with food or feed or a beverage. Compositions for oral administration include infected plants; extractions of the infected plants, and proteins purified from infected plants provided as dry powders, foodstuffs, aqueous or non-aqueous solvents, suspensions, or emulsions. Examples of non-aqueous solvents are propylene glycol, polyethylene glycol, vegetable oil, fish oil, and injectable organic esters. Aqueous carriers include water, water-alcohol solutions, emulsions or suspensions, including saline and buffered medial parenteral vehicles including sodium chloride solution, Ringer's dextrose solution, dextrose plus sodium chloride solution, Ringer's solution containing lactose or fixed oils. Examples of dry powders include any infected plant biomass that has been dried, for example, freeze dried, air dried, or spray dried. For example, the plants may be air dried by placing them in a commercial air dryer at about 120 degrees Fahrenheit until the biomass contains less than 5% moisture by weight. The dried plants may be stored for further processing as bulk solids or further processed by grinding to a desired mesh sized powder. Alternatively, freeze-drying may be used for products that are sensitive to air-drying. Products may be freeze dried by placing them into a vacuum drier and dried frozen under a vacuum until the biomass contains less than about 5% moisture by weight. The dried material can be further processed.

Infected plants may be administered as or together with one or more herbal preparations. Useful herbal preparations include liquid and solid herbal preparations. Some examples of herbal preparations include tinctures, extracts (e.g., aqueous extracts, alcohol extracts), decoctions, dried preparations (e.g., air-dried, spray dried, frozen, or freeze-dried), powders (e.g., lyophilized powder), and liquid. Herbal preparations can be provided in any standard delivery vehicle, such as a capsule, tablet, suppository, liquid dosage, etc. Those skilled in the art will appreciate the various formulations and modalities of delivery of herbal preparations that may be applied.

Those skilled in the art will also appreciate that a particularly useful method of obtaining the desired pharmaceutically active products is by extraction. Infected plants may be extracted to remove the desired products from the residual biomass, thereby increasing the concentration and purity of the product. Plants also may be extracted in a buffered solution.

For example, the fresh harvested plants may be transferred into an amount of ice-cold water at a ratio of one to one by weight that has been buffered with, e.g., phosphate buffer. Protease inhibitors can also be added as required. The plants can be disrupted by vigorous blending or grinding while suspended in the buffer solution and the extracted biomass removed by filtration or centrifugation. The transgene product carried in solution can be further purified by additional steps or converted to a dry powder by freeze-drying or precipitation. Extraction can also be carried out by pressing. Live plants can also be extracted by pressing in a press or by being crushed as they are passed through closely spaced rollers. The fluids expressed from the crushed plants are collected and processed according to methods well known in the art. Extraction by pressing allows the release of the products in a more concentrated form. However, the overall yield of the product may be lower than if the product were extracted in solution.

Infected plants, extractions, powders, dried preparations and purified protein products, etc., can also be in encapsulated form with or without one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active product may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

In some embodiments, an infected plant expressing a pharmaceutically active product, or biomass of an infected plant, is administered orally as medicinal food. Such edible compositions are consumed by eating raw, if in a solid form, or by drinking, if in liquid form. In some embodiments, the transgenic plant material is directly ingested without a prior processing step or after minimal culinary preparation. For example, the pharmaceutically active protein is expressed in a sprout that can be eaten directly (e.g., an alfalfa sprout, mung bean sprout, or a spinach or lettuce leaf sprout). In some embodiments, the plant biomass is processed and the material recovered after the processing step is ingested.

Therapeutic Methods and Pharmaceutical Compositions.

The antibody or portions thereof disclosed herein, or nucleic acids encoding the antibody or portions thereof, can be used to treat cancer. In several examples, the antibody or portions thereof, or nucleic acid encoding these polypeptides are of use to decrease cancer, such as in a subject. Thus, in several embodiments, the methods include administering to a subject a therapeutically effective amount of one or more of the antibody or portions thereof disclosed herein, or polynucleotides encoding these polypeptides, in order to decrease cancer. However, any of the antibody or portions thereof disclosed herein can be used to decrease cancer. In some embodiments, the peptides can be administered as a unit dose. In some embodiments, the polypeptides are administered as multimers.

A therapeutically effect amount of the antibody(ies) or portion(s) thereof, or polynucleotide encoding the peptide can be administered in the pharmaceutically acceptable carrier. Pharmacologically acceptable carriers (e.g., physiologically or pharmaceutically acceptable carriers) are well known in the art, and include, but are not limited to buffered solutions as a physiological pH (e.g. from a pH of about 7.0 to about 8.0, or at a pH of about 7.4). One specific, non-limiting example of a physiologically compatible buffered solution is phosphate buffered saline. Other pharmacologically acceptable carriers include penetrants, which are particularly suitable for pharmaceutical formulations that are intended to be topically applied (for example in the application of surgical wounds to promote healing).

The pharmacological compositions disclosed herein facilitate the use of at least one the antibody(ies) or portion(s) thereof, or polynucleotide encoding the antibody(ies) or portion(s) thereof, either in vivo or ex vivo, to decrease cancer. Such a composition can be suitable for delivery of the active ingredient to any suitable subject, and can be manufactured in a manner that is itself known, e.g., by means of conventional mixing, dissolving, granulating, emulsifying, encapsulating, entrapping or lyophilizing processes. Pharmacological compositions can be formulated in a conventional manner using one or more pharmacologically (e.g., physiologically or pharmaceutically) acceptable carriers, as well as optional auxiliaries that facilitate processing of the active compounds into preparations which can be used pharmaceutically. Proper formulation is dependent upon the route of administration chosen. Thus, for injection, the active ingredient can be formulated in aqueous solutions. For transmucosal administration, penetrants appropriate to the barrier to be permeated are used in the formulation. Such penetrants are generally known in the art.

For oral administration, a therapeutically effective amount of at least one antibody(ies) or portion(s) thereof, or a nucleic acid encoding the peptide, can be combined with carriers suitable for incorporation into tablets, pills, capsules, liquids, gels, syrups, slurries, suspensions and the like.

Protein drugs are subject to protease-mediated degradation in the digestive tract through the action of enzymes such as trypsin, chymotrypsin, and brush border peptidases, such that oral administration of large protein molecules often does not result in the intended therapeutic effect (Soltero and Ekwruibe, 2001 *Innovations in Pharmaceutical Technology*, 1:106-110).

In some embodiments, for parenteral administration, a therapeutically effective amount of the antibody(ies) or portion(s) thereof, or a nucleic acid encoding the peptide, can be administered by injection, such as by bolus injection or continuous infusion. Such compositions can take such forms as suspensions, solutions or emulsions in oily or aqueous vehicles, and can contain formulatory agents such as suspending, stabilizing and/or dispersing agents. Other pharmacological excipients are known in the art.

Optionally, the antibody(ies) or portion(s) thereof, or polynucleotide encoding the peptide can be contained within or conjugated with a heterologous protein, hydrocarbon or lipid, whether for in vitro or in vivo administration. Co-administration can be such that the antibody(ies) or portion(s) thereof, or polynucleotide encoding the peptide is administered before, at substantially the same time as, or after the protein, hydrocarbon, or lipid. In some embodiments, the antibody(ies) or portion(s) thereof, or polynucleotide encoding the peptide is administered at substantially the same time, as the protein, hydrocarbon, or lipid.

Other delivery systems can include time-release, delayed release or sustained release delivery systems. Such systems can avoid repeated administrations of the compositions of the invention described above, increasing convenience to the subject and the physician. Many types of release delivery systems are available and known to those of ordinary skill in the art. They include polymer based systems such as poly (lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems, such as lipids including sterols such as cholesterol, cholesterol esters and fatty acids or neutral fats such as mono- di- and tri-glycerides; hydrogel release systems; silastic systems; peptide based systems; wax coatings; compressed tablets using conventional binders and excipients; partially fused implants; and the like. Specific examples include, but are not limited to: (a) erosional systems in which the antibody(ies) or portion(s) thereof, or polynucleotide encoding the peptide is contained in a form within a matrix such as those described in U.S. Pat. Nos. 4,452,775; 4,667,014; 4,748,034; 5,239,660; and 6,218,371 and (b) diffusional systems in which an active component permeates at a controlled rate from a polymer such as described in U.S. Pat. Nos. 3,832,253 and 3,854,480. In addition, pump-based hardware delivery systems can be used, some of which are adapted for implantation.

The therapeutically effective amount of the antibody(ies) or portion(s) thereof, or polynucleotide encoding the peptide will be dependent on the antibody(ies) or portion(s) thereof, or polynucleotide encoding the peptide that is utilized, the subject being treated, the severity and type of the affliction, and the manner of administration. For example, a therapeutically effective amount of a polynucleotide encoding the peptide can vary from about 0.01 µg per kilogram (kg) body weight to about 1 g per kg body weight, such as about 1 µg to about 5 mg per kg body weight, or about 5 µg to about 1 mg per kg body weight. The exact dose is readily determined by one of skill in the art based on the potency of the specific compound the age, weight, sex and physiological condition of the subject.

With regard to the administration of nucleic acids, one approach to administration of nucleic acids is direct treatment with plasmid DNA, such as with a mammalian expression plasmid. As described above, the nucleotide sequence encoding the antibody(ies) or portion(s) thereof can be placed under the control of a promoter to increase expression of the molecule.

When a viral vector is utilized for administration in vivo, it is desirable to provide the recipient with a dosage of each recombinant virus in the composition in the range of from about 105 to about $10^{10}$ plaque forming units/mg mammal, although a lower or higher dose can be administered. The composition of recombinant viral vectors can be introduced into a mammal either prior to any evidence of a cancer, or to mediate regression of the disease in a mammal afflicted with the cancer. Examples of methods for administering the composition into mammals include, but are not limited to, exposure of cells to the recombinant virus ex vivo, or injection of the composition into the affected tissue or intravenous, subcutaneous, intradermal or intramuscular administration of the virus. Alternatively the recombinant viral vector or combination of recombinant viral vectors may be administered locally by direct injection into the cancerous lesion in a pharmaceutically acceptable carrier. Generally, the quantity of recombinant viral vector, carrying the nucleic acid sequence of one or more Antibody or portions thereof to be administered is based on the titer of virus particles. An exemplary range of the immunogen to be administered is $10^5$ to $10^{10}$ virus particles per mammal, such as a human.

In one specific, non-limiting example, a pharmaceutical composition for intravenous administration would include about 0.1 µg to 10 mg of the antibody(ies) or portion(s) thereof per patient per day. Dosages from 0.1 up to about 100 mg per patient per day can be used, particularly if the agent is administered to a secluded site and not into the circulatory or lymph system, such as into a body cavity or into a lumen of an organ. Actual methods for preparing administrable compositions will be known or apparent to those skilled in the art and are described in more detail in such publications as Remington's Pharmaceutical Sciences, 19$^{th}$ Ed., Mack Publishing Company, Easton, Pa., 1995.

Single or multiple administrations of the compositions are administered depending on the dosage and frequency as required and tolerated by the subject. In some embodiments, the dosage is administered once as a bolus, but in another embodiment can be applied periodically until a therapeutic result is achieved. Generally, the dose is sufficient to treat or ameliorate symptoms or signs of disease without producing unacceptable toxicity to the subject. Systemic or local administration can be utilized.

In a further method, an additional agent is administered. In one example, this administration is sequential. In other examples, the additional agent is administered simultaneously with the antibody(ies) or portion(s) thereof.

The invention will be further described in the following examples, which do not limit the scope of the invention described in the claims.

Example 1

Materials and Methods. FIG. 1 is a coomasie blue-stained gels showing recovered antibody expressed in the plant expression system. Expression vectors were co-infiltrated into wild-type plants. Plant tissue was harvested and extracted and hD11 antibody was captured and eluted by protein A chromatography and separated by PAGE. HR; heated and reduced. NHNR; non-heated, non-reduced. The anti-CD25 antibody made in a wild-type plant is also referred to as SD-889825-PW-A (IBIO-101, wild type Plant), and the anti-CD25 antibody manufactured in the c-105 strain is SD-889825-PC-A (IBIO-101, c-105 Plant Afucosylated). As used herein, the following nomenclature is used interchangeably: (SD-889825-CW-A is IBIO-101, wild-type CHO cells); (SD-889825-CG-A is IBIO-101, CHO cells Afucosylated); (SD-889825-PW-A is IBIO-101, wild-type plant); and (SD-889825-PC-A is IBIO-101, c-105 plant Afucosylated).

Expression vectors were co-infiltrated into C105 DXT/DFT plants deficient in fucosylation and xylosylation. Plant tissue was harvested and extracted and hD11 antibody was captured and eluted by protein A chromatography and separated by PAGE. HR; heated and reduced. NHNR; non-heated, non-reduced.

FIG. 2 Representative Mass Spectrometry Analysis of Masses of Plant-made hD11Heavy and Light Chains (C105 plants).

Figure 3:
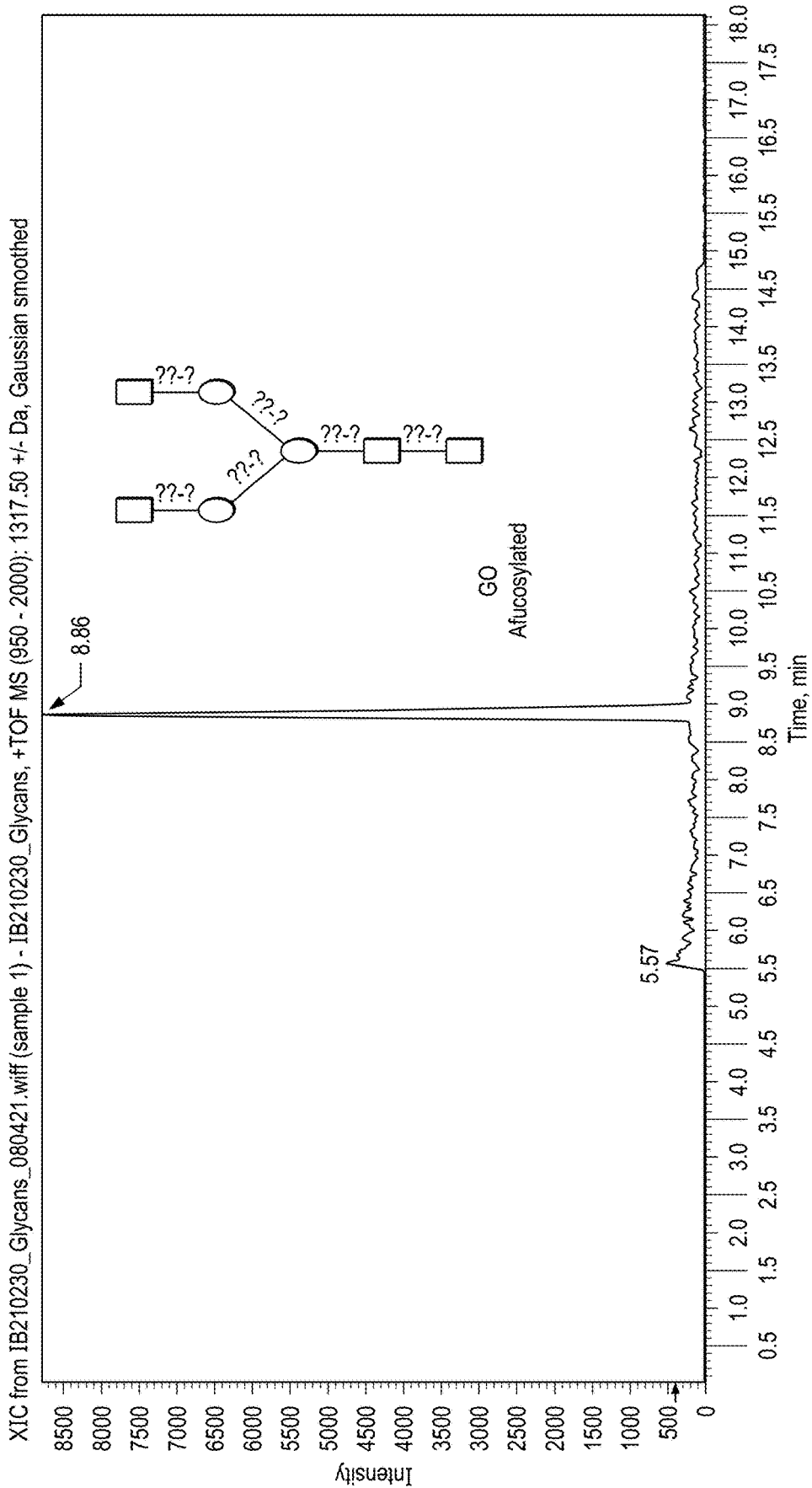
FIG. 3 shows a mass spectrometry analysis of glycans released from plant-made hD11 (C105 plants), hD11was made without fucose to promote high ADCC activity in vivo.

FIG. 3 shows a mass spectrometry analysis of glycans released from plant-made hD11 (C105 plants), hD11was made without fucose to promote high ADCC activity in vivo.

Example 2. Plant-Based Expression and Glyco-Engineering of Novel IL-2 Signaling Permissive Anti-CD25 Antibodies for Effective Treg Depletion in Cancer Monoclonal antibodies that target CD25 for T regulatory cell (Treg) depletion without blocking IL-2-STAT5 signaling on T effector cells in the Tumor Microenvironment have been shown to provide a favorable response against solid tumors in preclinical models as a monotherapy. Additionally, combination therapy of CD25 antibodies with immune checkpoint blockage has shown synergistic effects. A novel AI/ML platform capable of predicting epitope embodiments of structural epitopes was used to steer antibody selection towards specific epitopes. The lead molecule RTX-003 (IBIO-101) is an anti-CD25 antibody selected from a panel of conventional and epitope-selective clones and expressed in a plant-based expression system using *Nicotiana benthamiana* plants. Using a glyco-engineered (GE) deltaXT/FT *N. benthamiana* host, lacking beta 1,2-xylosyltransferase and alpha 1,3-fucosyltransferase activity, we were able to produce afucosylated IBIO-101, with significantly increased effector function. IBIO-101 bound specifically to CD25+ cancerous cells, preserved IL-2 signaling via pSTAT5, and elicited potent antibody-dependent cellular cytotoxicity (ADCC) activity. Preclinical evaluation of IBIO-101, produced with iBio's FASTPHARMING® and GLYCANEERING™ platforms, showed equivalent efficacy and potency compared with a CHO-made IBIO-101. The rapid scalability of GE plant-based expression systems along with the expected time-savings to produce GMP material support the advancement of IBIO-101 into clinical development.

Figure 4:
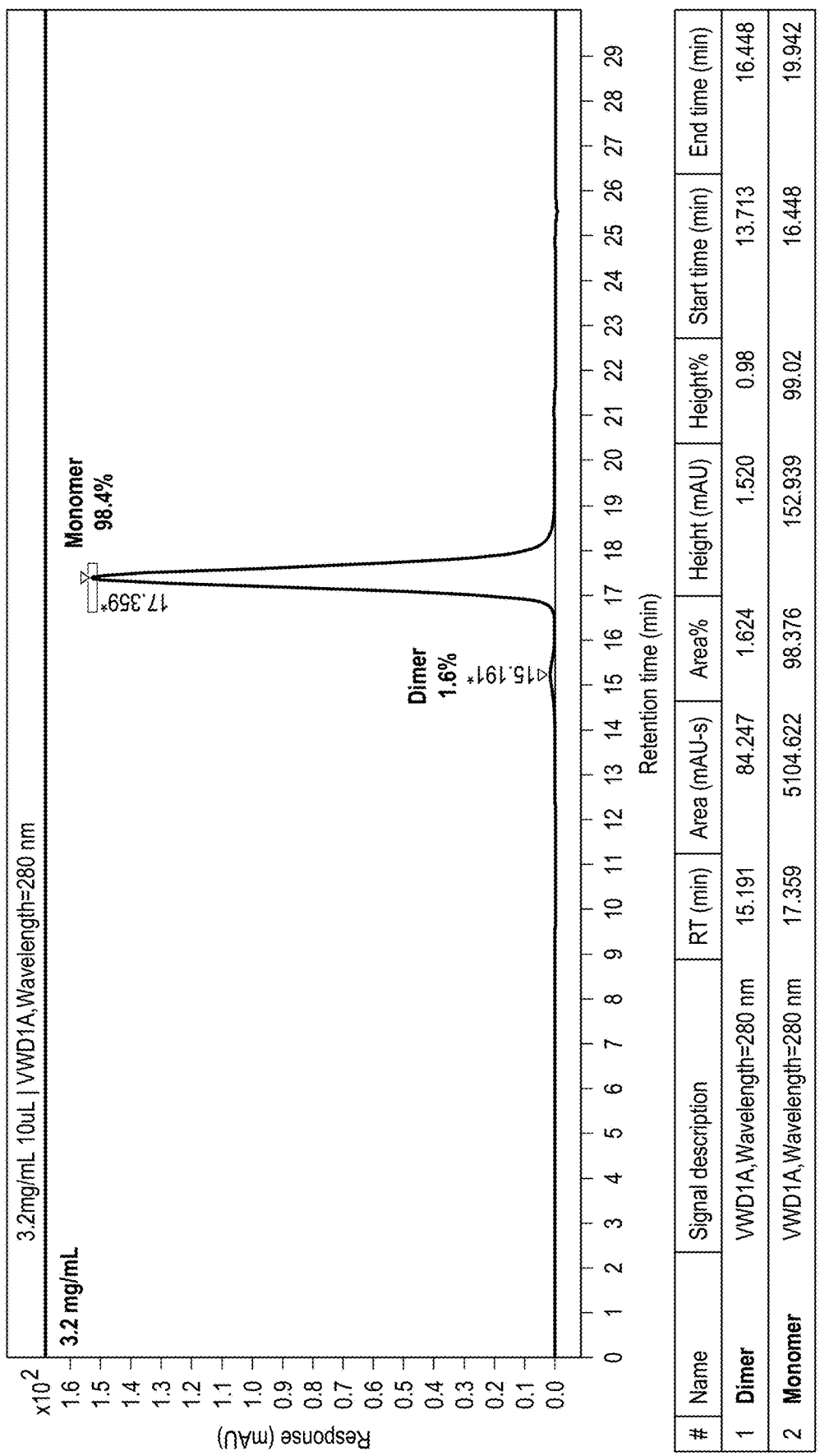
FIG. 4 is a graph that shows an HPLC showing the purity of the antibody produced in plants.
Figure 4:
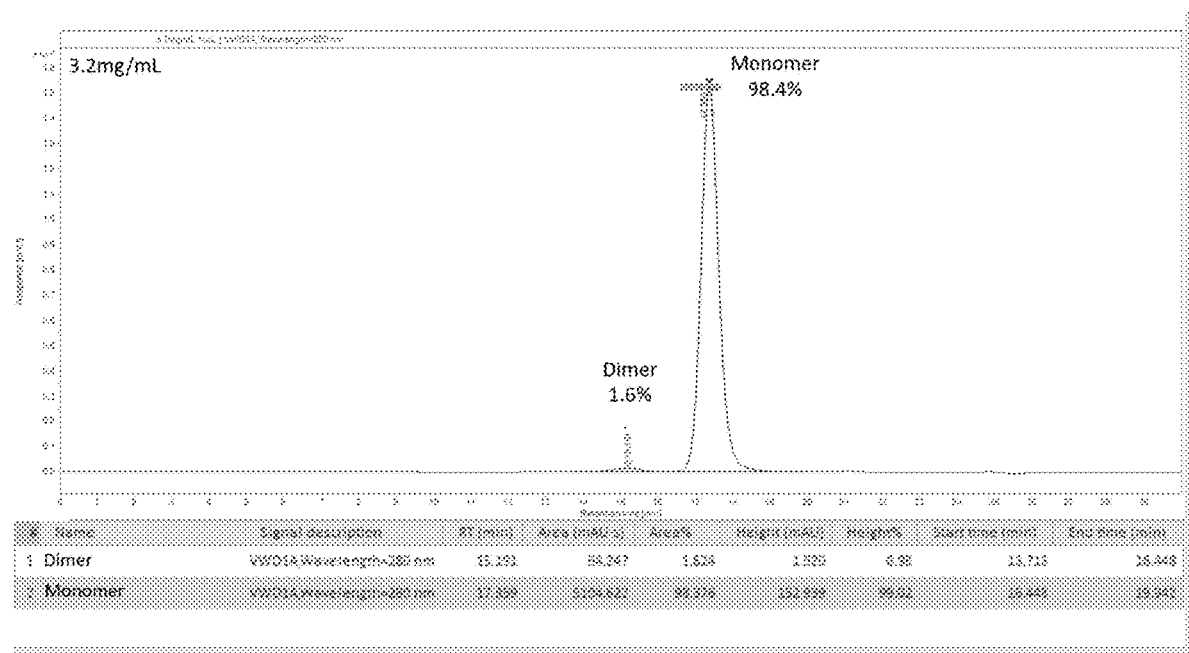
Figure 5:
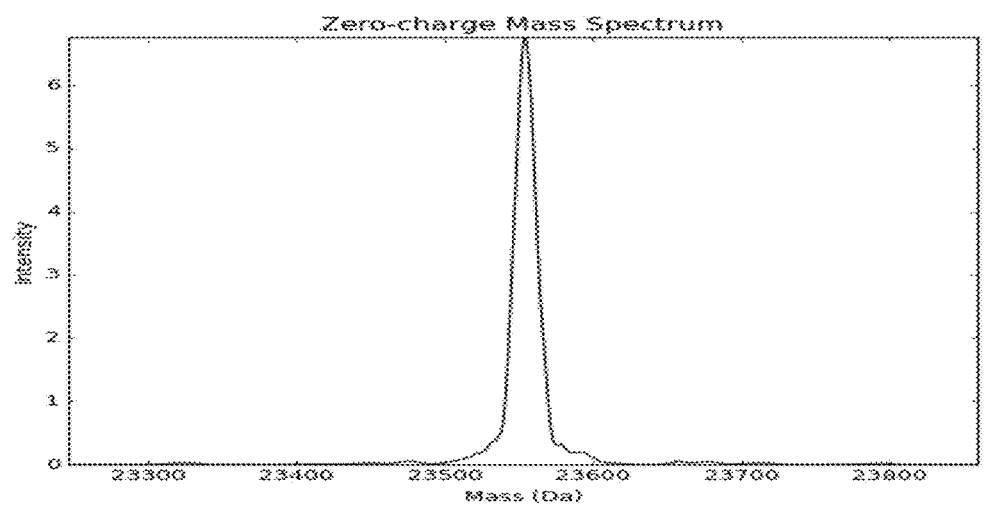
FIG. 5 is a graph that shows mass spectrometry characterization deconvoluted MW of light chain.
Figure 6:
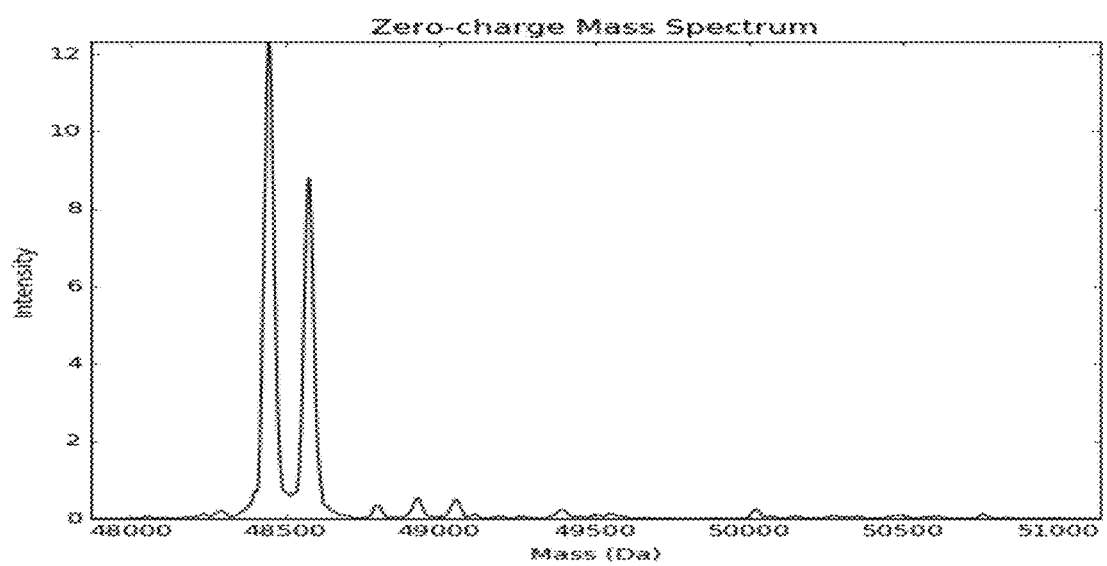
FIG. 6 is a graph that shows mass spectrometry characterization deconvoluted MW of deglycosylated heavy chain.
Figure 7:
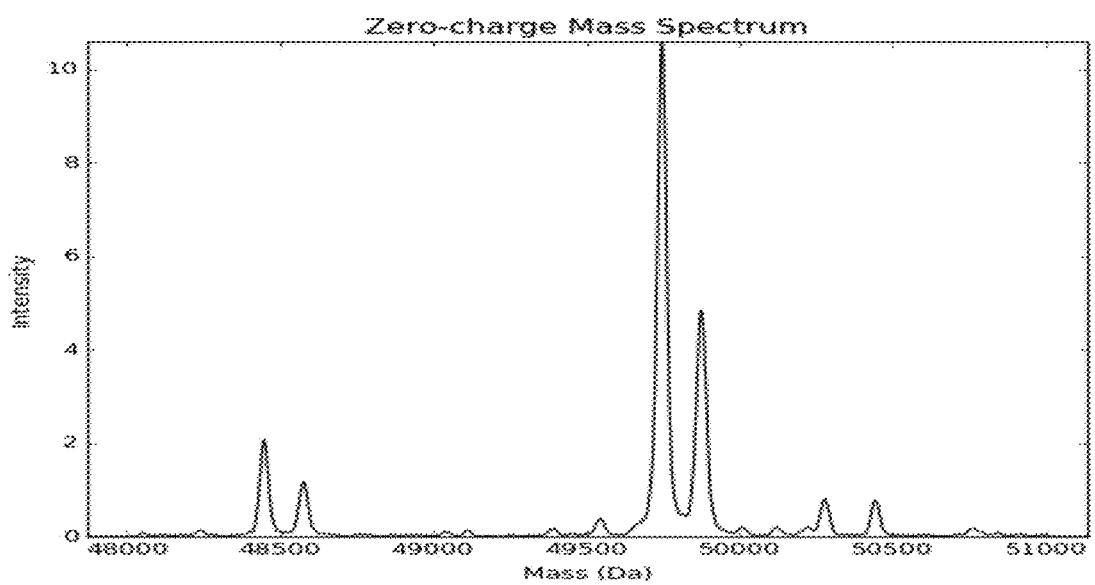
FIG. 7 is a graph that shows mass spectrometry characterization deconvoluted MW of glycosylated heavy chain.
Figure 8:
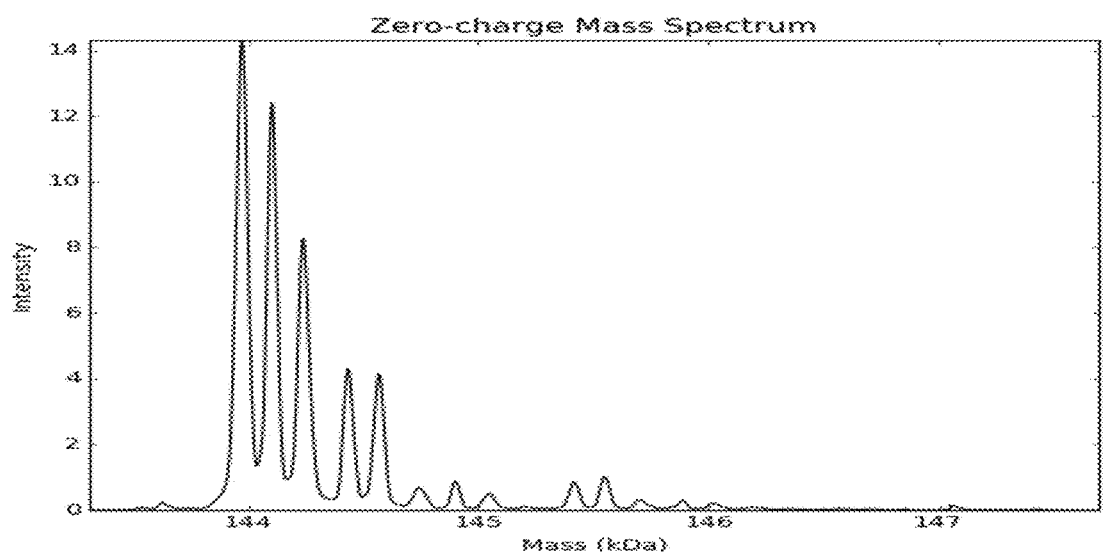
FIG. 8 is a graph that shows mass spectrometry characterization deconvoluted MW of intact deglycosylated sample.
Figure 9:
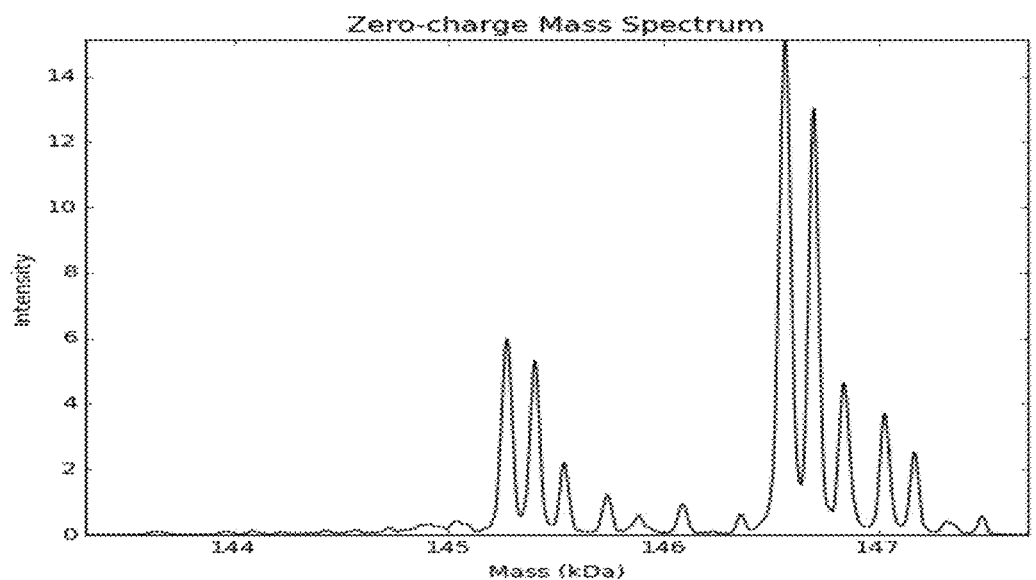
FIG. 9 is a graph that shows mass spectrometry characterization deconvoluted MW of intact glycosylated sample.
Figure 10:
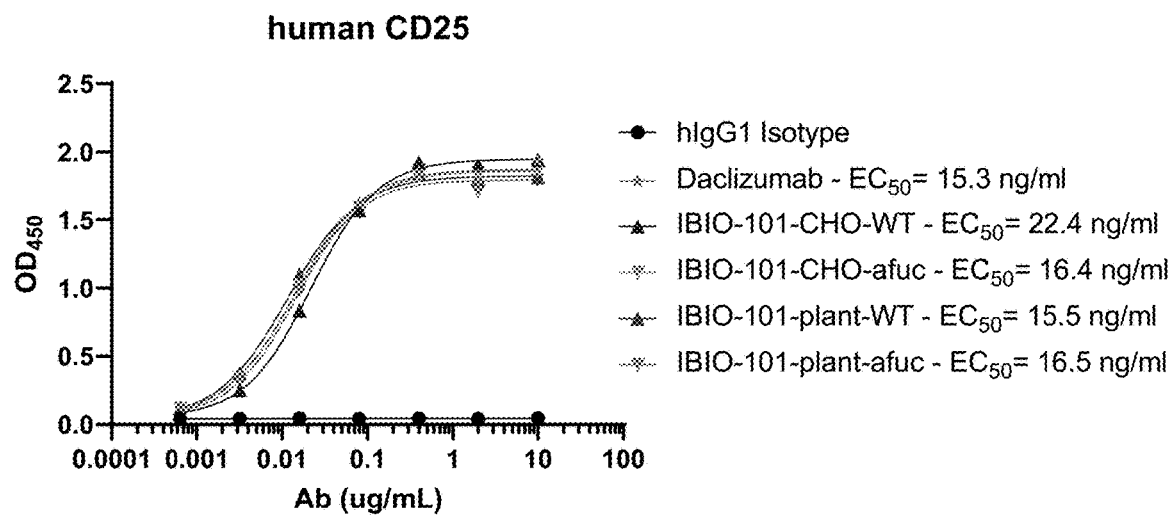
FIG. 10 is a graph that shows CD25 binding ELISA graph for human CD25.
Figure 11:
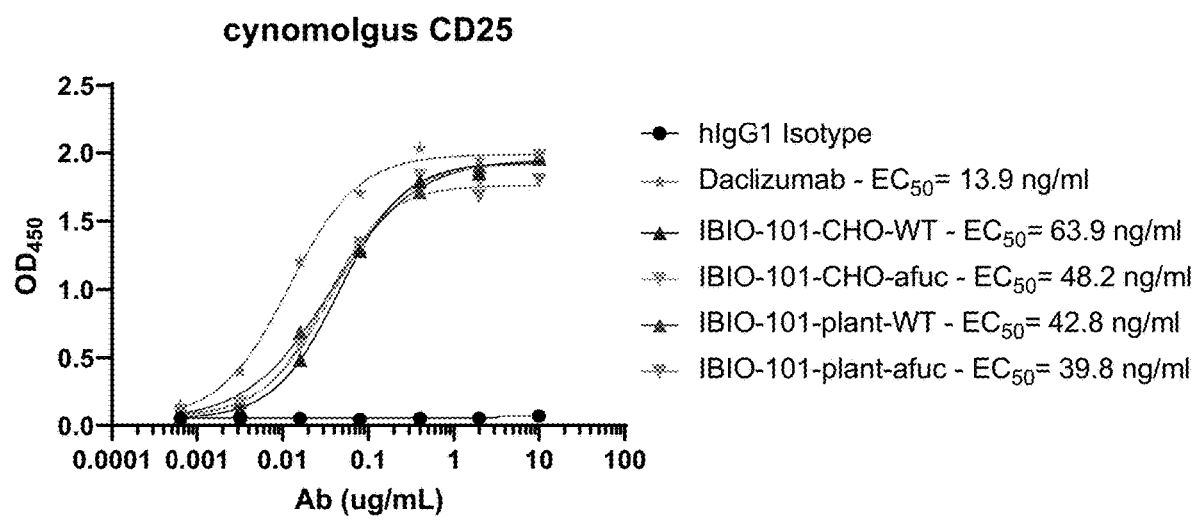
FIG. 11 is a graph that shows CD25 binding ELISA graph for cynomolgus CD25.
Figure 12:
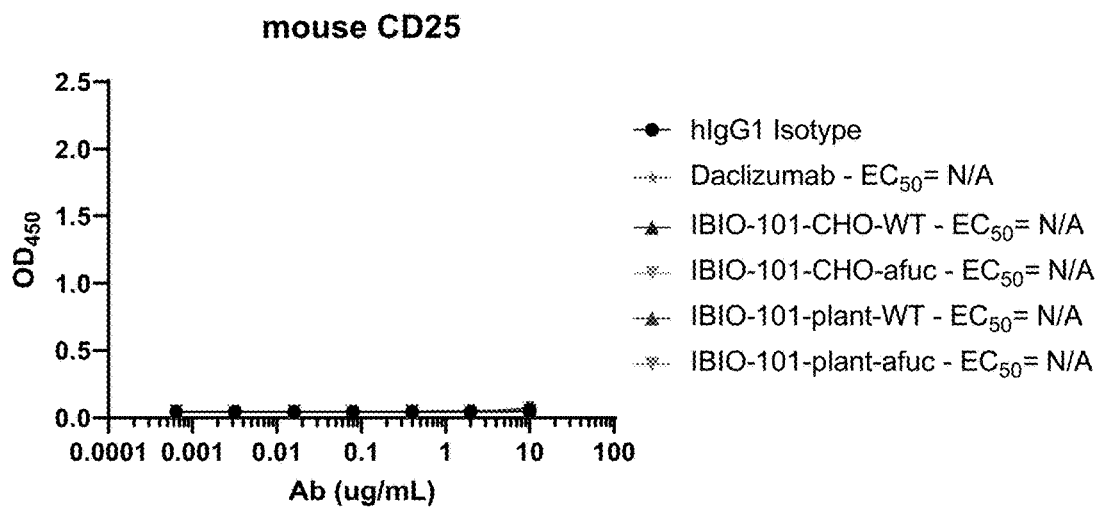
FIG. 12 is a graph that shows CD25 binding ELISA graph for mouse CD25.

FIG. 4 is a graph that shows an HPLC showing the purity of the antibody produced in plants. FIG. 5 is a graph that shows mass spectrometry characterization deconvoluted MW of light chain. FIG. 6 is a graph that shows mass spectrometry characterization deconvoluted MW of deglycosylated heavy chain. FIG. 7 is a graph that shows mass spectrometry characterization deconvoluted MW of glycosylated heavy chain. FIG. 8 is a graph that shows mass spectrometry characterization deconvoluted MW of intact deglycosylated sample. FIG. 9 is a graph that shows mass spectrometry characterization deconvoluted MW of intact glycosylated sample.

It was found that the IBIO-101 molecules bind to human and cynomolgus CD25 but not mouse CD25. The ELISA assay shows that WT fucosylated and afucosylated IBIO-101 molecules made in CHO and plants and Daclizumab binding to immobilized human or cynomolgus CD25 in a concentration-dependent manner. No binding was detected to immobilized mouse CD25. Values plotted are measured absorbance at 450 nm wavelength. EC50 values are averages of n≥3 experiments.

CD25 Binding ELISA. ELISA plates (Biolegend, 423501) were first coated with 1 pg/mL of either human CD25 (Sino Biologicals, 10165-H08H) or cynomolgus CD25 (Sino Biologicals, 90265-C08H) in 50 mM carbonate buffer pH 9.5 (Teknova, S9225) overnight at 4° C. The next day, plates were washed three times with wash buffer [1× PBS with 0.1% Tween-20 (Teknova, P0207)] followed by the addition of blocking buffer [1× PBS, 1% BSA (Teknova, B0101)] for 1 hour at room temperature. After blocking, plates were washed three times with wash buffer followed by the addition of the anti-CD25 or control antibodies in wash buffer at increasing concentrations (0.0006-10 pg/mL) for 1 hour at room temperature. After incubation, plates were washed three times with wash buffer followed by the addition of goat anti-human IgG-HRP secondary antibody (Biorad, STAR126P) at 1:2500 dilution in wash buffer for 1 hour at room temperature. After incubation with secondary antibody, plates were washed six times with wash buffer followed by the addition of TMB substrate (VWR, 95059-154) for 5 minutes at room temperature. After TMB substrate incubation, ELISA stop solution (Thermo Fisher, SSO4) was added to the plate at equal volume to the TMB substrate and the absorbance was read at 450 nm. The data was plotted using GraphPad Prism 9.3.0 software and the $EC_{50}$ values were calculated by the software.

SUDHL-1 and $iT_{reg}$ Cell Binding Assay. SUDHL-1 cells (ATCC, CRL-2955) were cultured in RPMI 1640 (ATCC, 30-2001) supplemented with 10% FBS (ATCC, 30-2020) and 1× Penicillin-Streptomycin (Corning, 30-002-CI). Human induced $T_{reg}$ ($iT_{reg}$) cells were cultured in Immunocult XF Tcell expansion media (Stemcell, 10981) supplemented with 25 µl/ml of Immunocult Human CD3/CD28/CD2 T cell Activator (Stemcell, 10970), and 3000 IU/ml of IL2 (Miltenyi Biotec, 130-097-74).

For the cell binding assay, DPBS (VWR, 45000-436) supplemented with 2% FBS was used as the assay buffer. SUDHL-1 cells or $iT_{reg}$ cells were counted then resuspended in the assay buffer, then seeded onto 96-well plates (VWR, 89089-826) at $1\times10^5$ cells/well. The plates were centrifuged and then kept on ice for the remaining assay steps after aspiration of the supernatant. Following supernatant aspiration, the anti-CD25 or control antibodies in the assay buffer were added to the cells at increasing concentrations (0.64-10,000 ng/mL) for 20 minutes on ice. After incubation, the plates were centrifuged and the supernatant was aspirated, then the cells were washed once with the assay buffer followed by centrifugation and supernatant aspiration. After wash, rat-anti-human IgG Alexa Fluor 647 secondary antibody (Biolegend, 410714) was added at 1:200 dilution in the assay buffer for 20 minutes on ice. After incubation, the plates were centrifuged and the supernatant was aspirated, then the cells were washed once with the assay buffer followed by centrifugation and supernatant aspiration. After wash, DAPI (Biolegend, 422801) was added to the cells at 1:5000 dilution in the assay buffer. Cell binding was analyzed on a Miltenyi MACSQuant 16 flow cytometer. Flow cytometry data were analyzed with the FlowJo flow cytometry analysis software. For making graphs and calculation of the $EC_{50}$ values GraphPad Prism 9.3.0 was used.

SUDHL-1 and $iT_{reg}$ ADCC Reporter Assay. SUDHL-1 cells (ATCC, CRL-2955) were cultured in RPMI 1640 (ATCC, 30-2001) supplemented with 10% FBS (ATCC, 30-2020) and 1× Penicillin-Streptomycin (Corning, 30-002-CI). Human induced $T_{reg}$ ($iT_{reg}$) cells were Immunocult XF Tcell expansion media (Stemcell, 10981), 25 µl/ml of Immunocult Human CD3/CD28/CD2 T cell Activator (STEMCELL, 10970), and 3000 IU/ml of TL2 (Miltenyi, 130-097-74). Jurkat NFAT/CD16 cells (Invivogen, jktl-nfat-cd16) were cultured in IMDM (ATCC, 30-2005) supplemented with 10% FBS (Sigma, F4135500) and 100 pg/ml Normocin. To maintain selection, 10 pg/ml of blasticidin and 100 pg/ml of Zeocin was added to the growth medium at every second passage of Jurkat NFAT/CD16 cells.

For ADCC reporter assay, SUDHL-1 cells or $iT_{reg}$ cells were counted to assess the cell number and viability. Cells were centrifuged and resuspended in Xvivo 15 medium (Lonza, BE02-053Q) at $1 \times 10^6$ cells/ml. $5 \times 10^4$ cells were seeded per well onto 96 well plates (VWR, 89131-676). After seeding, anti-CD25 or control antibodies in Xvivo 15 media were added to the cells at increasing concentrations (0.32-5000 ng/mL) for 20 minutes at 37° C., 5% $CO_2$. After incubation with the antibodies, $1 \times 10^5$ Jurkat NFAT/CD16 cells were added into each well then incubated at 37° C., 5% $CO_2$ for 16-17 hrs. After incubation, the assay plates were equilibrated at room temperature for 15 minutes prior to plate reading. To look at reporter cell activation, 20 pL of media from each well of the assay plate was added into the corresponding well of a flat-bottom white 96-well plate (VWR, 89130-330), along with 50 μL/well of the QUANTI-Luc Gold (Invivogen, rep-qlcgl) solution. The plates were read using Promega GloMax plate reader set for luminescence reading with an integration time of 0.5 sec/well. The data was normalized by subtracting the mean baseline luminescence values from the blank wells from all other wells and analyzed using Graphpad Prism 9.3.0, including calculation of the $EC_{50}$ values.

PhosphoSTAT5 (pSTAT5) assay. HEK-Blue IL-2 cells (Invivogen, Hkb-il2) were cultured in DMEM (VWR, 45001-304) supplemented with 10% FBS (VWR, 45001-108), 1× Penicillin-Streptomycin (VWR, 45000-652), 100 mg/mL normocin (Invivogen, Ant-nr-1), 1 pg/mL puromycin (Invivogen, Ant-pr-1). 1× HEK-Blue CLR selection (Invivogen, HB-csm) were used in this assay. For the pSTAT5 assay, DMEM supplemented with 10% FBS, 1× Penicillin-Streptomycin, and 100 mg/mL normocin, was used as the test medium. HEK-Blue IL-2 cells were counted then resuspended in PBS at $1 \times 10^6$ cells/mL. The cells were stained with the LIVE/DEAD Fixable Aqua Dead Cell Stain (Thermo Fisher, L34957) for 30 minutes on ice. After staining, the cells were centrifuged then washed with PBS. After wash, the cells were centrifuged and resuspended with the test medium, then seeded into 96-well plates (VWR, 89089-826) at $1 \times 10^5$ cells/well. After seeding, the plates were centrifuged, the supernatant was removed, and the cells were resuspended in the test medium containing increasing concentrations (0.1-100 pg/mL) of anti-CD25 or control antibodies and incubated for 15 minutes at 37° C., 5% $CO_2$. After incubation with the antibodies, the test medium containing IL-2 (VWR, 10779-568) was added to the cells at a final IL-2 concentration of 100 ng/mL and incubated for another 10 minutes at 37° C., 5% $CO_2$. After incubation with IL-2, the plates were centrifuged, the supernatant was removed, and the cells were resuspended in the fixation buffer (BD Biosciences, 554655) and incubated for 15 minutes at room temperature. After fixation, the plates were centrifuged, the supernatant was removed, and the cells were washed with ice-cold the FACS buffer (PBS with 2% FBS and 2 mM EDTA). Following wash, the plate was centrifuged, the supernatant was removed, and the cells were resuspended in ice-cold the permeabilization buffer (BD Biosciences, 558050) and incubated for 15 minutes on ice. After that, the plates were centrifuged, the supernatant was removed, and the cells were washed with ice-cold the FACS buffer one more time before adding mouse anti-Stat5 (pY694) Alexa Fluor 488 (BD Biosciences, 562075) to the cells and incubating for 30 minutes on ice. After incubation, the plate was centrifuged, the supernatant was removed, and the cells were washed with ice-cold the FACS buffer. pSTAT5 levels were analyzed on a Miltenyi MACSQuant 16 flow cytometer. Flow cytometry data were analyzed with FlowJo flow cytometry analysis software and plotted in GraphPad Prism 9.3.0. GraphPad Prism 9.3.0. was also used to calculate the $EC_{50}$ values.

In vitro $iT_{reg}$ ADCC assay. $iT_{reg}$ isolation and expansion. $T_{reg}$ cells were isolated from human peripheral blood mononuclear cells using EasySep $T_{reg}$ negative isolation kit (Stemcell, 19232). Freshly isolated $T_{reg}$ were seeded at $10^6$ cell/mL in the human induced Treg ($iT_{reg}$) cells growth media (Immunocult XF Tcell expansion media (Stemcell, 10981), supplemented with 25 μl/ml of Immunocult Human CD3/CD28/CD2 T cell Activator (Stemcell, 10970), and 3000 IU/mL of IL-2 (Miltenyi Biotec, 130-097-743) for $T_{reg}$ induction. Cells was monitored for viability and viable cell density was adjusted to ~ $1 \times 10^6$-$2 \times 10^6$ cells/mL every 2-3 days by adding fresh $iT_{reg}$ growth media. The purity of isolated $iT_{reg}$ were evaluated be staining with CD3-BV605 (BioLegend, 317322), CD4-PerCP/cy5.5 (BioLegend, 300530), CD25-APC-cy7 (BioLegend, 302614) and FoxP3-FITC (BioLegend, 320106).

ADCC evaluation. $iT_{reg}$ cells were counted and cell viability was assessed. Cells were centrifuged and resuspended in the assay media (RPMI 1640, 10% FBS, 1% of penicillin/streptomycin, 5 ng/ml of IL2). 5000 $iT_{reg}$ cells were seeded per well of 96 well plate. After seeding the cells, hIgG1 isotype control or anti-CD25 antibodies were added to the cells at increasing concentrations (0.64-10000 ng/mL) for 10 minutes at 37° C., 5% $CO_2$. After that, 105 peripheral blood mononuclear cells (PBMC) (Stemcell, 70025.1) were added per well of 96 well plate. Cells and antibodies were incubated at 37° C. in 5% $CO_2$ incubator for 3 days. Samples were stained with LIVE/DEAD™ fixable Aqua Dead Cell Stain Kit (Thermo Fisher, L34957), followed by staining with TruStain FCX blocking antibody (BioLegend, 422302) for 15 minutes on ice. After that, the cells were stained with anti-human CD3-BV605 (BioLegend, 317322), CD4-PerCP/Cy5.5 (BioLegend, 300530), CD8a-APC (BioLegend, 300912), CD69-PE (BioLegend, 31090), CD25-APC-Cy7 (BioLegend, 302614) for 30 minutes on ice. Samples then fixed, permeabilized, and stained for FoxP3-FITC (BioLegend, 320106) for 30 minutes on ice.

$iT_{reg}$ cells were gated (CD3$^+$, CD4$^+$, CD25$^+$, Foxp3$^+$). % of $iT_{reg}$ cell lysis was calculated by % dead $iT_{reg}$ (CD3$^+$, CD4$^+$, CD25$^+$, Foxp3$^+$, aqua Live/dead$^+$) per total $iT_{reg}$. Activated CD4$^+$ cells were gated (CD3$^+$, CD4$^+$, Foxp3$^-$, CD69$^+$). % of activated CD4$^+$ cell lysis was calculated by % dead activated CD4$^+$ (CD3$^+$, CD4$^+$, Foxp3$^-$, CD69$^+$, aqua Live/dead$^+$) per total activated CD4$^+$ cells. Activated CD8$^+$ cells were gated (CD3$^+$, CD8$^+$, CD69$^+$), % of activated CD8$^+$ cell lysis was calculated by % dead activated CD8$^+$ (CD3$^+$, CD8$^+$, CD69$^+$, aqua Live/dead$^+$) per total activated CD8$^+$ cells.

In vivo $iT_{reg}$ ADCC assay. The IL2RA$^{human/human}$ humanized mice were used for these experiments. The sequences encoding the extracellular domain of human IL2RA were inserted to replace the sequences encoding the extracellular domain of murine IL2RA. Homozygous mice were used for the experiments. The experiments were performed at Biocytogen Pharmaceuticals (Beijing, China).

Approximately 120 μL of blood was collected from mice's orbital sinus with anticoagulant (EDTA-K2) 3 days after treatment with hIgG1 isotype control or anti-CD25 antibodies (4 mice per group). For flow cytometry analysis, 100 μL of blood sample was mixed with 1 mL of red blood cell lysis buffer for 5 minutes at room temperature, followed by centrifugation at 500 g for 5 minutes at 4° C. Counting and recording of total cell numbers was done using an automated cell counter. Blood cells were resuspended in PBS to the required volume for flow cytometry. Samples were divided into two sets to detect $T_{reg}$ and Teff cells.

For $T_{reg}$ detection, samples were stained with anti-CD16/CD32 (Biolegend, 101302) at room temperature for 15 minutes followed by staining with antibodies cocktail containing mouse CD45+ -APC/cy7 antibody (Biolegend, 103116), mouse CD3+ -Alexa Fluor 700 antibody (Biolegend, 100216), mouse CD4+ -FITC (Biolegend, 100406) antibody, mouse CD8+ -BV605 (Biolegend, 100748) antibody, human CD25+ -APC (Biolegend, 302610) antibody for 30 minutes on ice. After that, samples were fixed, permeabilized and stained with mouse Foxp3-PE/Cy7 (eBioscience, 25-5773-82) antibody.

For CD4+ and CD8+ T effector cells detection, samples were stained with antibodies cocktail containing mouse CD45+ -APC/Cy7 antibody (Biolegend, 103116), mouse CD3+ -Alexa Fluor 700 antibody (Biolegend, 100216), mouse CD4+ -FITC (Biolegend, 100406) antibody, mouse CD8+ -BV605 (Biolegend, 100748) antibody, mouse CD44-PE antibody (Biolegend, 103008), mouse CD62L-PerCP/Cy5.5 antibody (Biolegend, 104432). Counts were analyzed by flow cytometry.

Primary immune cell binding assay. $iT_{reg}$ was isolated from human PBMC as described in section [0222]. SUDHL-1 cells (ATCC, CRL-2955), human monocyte (Stemcell, 70034), human pan B cells (Stemcell, 70023), human pan T cells (Stemcell, 700024.1), human effector memory CD8+ T cells (Stemcell, 200-0383) and human NK cells (Stemcell, 70036) were cultured in RPMI 1640 (ATCC, 30-2001) supplemented with 10% FBS (Sigma, F4135) and 1× Penicillin-Streptomycin (Corning, 30-002-CI).

Assay buffer consisting of DPBS (VWR, 45000-436), 2% FBS and 0.1% EDTA (Quality Biological, 351-027-721) was prepared and kept on ice until used. Cells were counted and seeded in 96 well plate (VWR, 89089-826) at 1×105 cells/well in assay buffer. The plate was centrifuged at 300 g for 5 minutes, and the supernatant were removed. Human IgG1 Isotype (Biolegend, 403502), Daclizumab (Absolute antibody, Ab00187-10.0), IBIO-101-CHO-WT (SD-889825-CW), IBIO-101-CHO-afuc (SD-889825-CG), IBIO-101-plant-WT (SD-889825-PW), IBIO-101-plant-afuc (SD-889825-PC) were added to individual well at concentration 10 pg/mL in assay buffer. Cells were incubated on ice for 20 minutes. After incubation, the cells were washed by centrifuging the plate at 300 g for 5 min and removing the supernatant, then the cells were washed once with assay buffer and the supernatant was removed following centrifugation. Rat-anti-human IgG Alexa Fluor 647 secondary antibody (Biolegend, 410714) diluted in assay buffer (1:200) was added to the cells followed by incubation on ice for 20 minutes in dark. After incubation with secondary antibody, cells were washed once with assay buffer. Afterwards, DAPI (Biolegend, 422801) was added to the cells at 1:5000 dilution in assay buffer. Cells were analyzed on a Miltenyi MACSQuant 16 flow cytometer. Flow cytometry data were analyzed with FlowJo (Becton, Dickinson & Company) analysis software. Cell population was first identified and gated by their forward and side scatter. Singlet were gated by using side scatter area and side scatter height. Live singlet cells were identified using negative stain of DAPI (BV-421). CD25-APC cells were then determined from the live cell population.

SEC-HPLC. Sample preparation for sec analysis. All samples were filtered using 0.2 μm spin filters primed with mobile phase, 200 mm phosphate, pH 6.2, 250 mm potassium chloride before transferring to 300 μl autosampler vial for analysis.

SEC data acquisition. IBIO-101 sample were loaded onto TSKG3SWxl, 5 μm 7.8 mm×30 cm and TSKGuard SWxl 7 μm, 6.0 mm×4 cm. Chromatography was performed at 0.5 mL/min with 200 mM phosphate, pH6.2, 250 mM potassium chloride as mobile phase, with 30 min analysis time at 20-25° C. BEH200 SEC standard (Waters) was used to assess system performance and provide retention time references.

Data processing. Peak integration was performed in automatic setting. Peaks were integrated in the range from 7.5-22 min. Baseline was calculated from 7.5 min, and shoulders were dropped. The main peak presumed to be intact fully assembled IBIO-101.

LC-MS—released glycan analysis. Sample preparation for LC-MS analysis. The deglycosylated intact sample is used for this analysis.

LC-MS data acquisition. LC-MS analysis for intact sample was performed normal MS method. Analyte ionization was performed using Turbo VTM ion source at electrospray potential of 5.3 kV. Curtain gas was set up at 30 psi. Gas 1 and 2 pressure were both set to 80 psi. Gas 2 temperature was set up 675° C. Mass range for MS scan was 900 Da-2000 Da. Accumulation time was 0.4 s. TOF bin size was 80. Method duration was 22 min. Following parameters were used for HPLC: (i) BioZen Glycan(150×2.1, 2.6 um, (ii) Phase A was 0.10% FA in H20 (iii) Phase B was 0.10% FA in ACN; column oven was set to 65° C., (iv) flow rate was set to 0.43 mL/min; gradient time=25 min.

LC-MS data processing. Raw data in the *.wiff format were directly uploaded to PeakView software without additional processing. Extracted ion chromatograms are generated based on the glycans molecular weight.

Table 1 is a CD25 binding ELISA summary table. Table 2A is an SUDHL-1 cell binding assay summary table. Table 2B is an iTreg cell binding assay summary table.

TABLE 1

CD25 Binding ELISA: summary table.

| | CD25 EC50 (ng/ml, n ≥ 3) | | | | | |
|---|---|---|---|---|---|---|
| | Human | | Cynomolgus | | Mouse | |
| | Average | SD | Average | SD | Average | SD |
| hIgG1 Isotype | N/A | N/A | N/A | N/A | N/A | N/A |
| Daclizumab | 18.7 | 4.4 | 19.1 | 5.1 | N/A | N/A |
| IBIO-101-CHO-WT | 19.9 | 4.9 | 54.4 | 19.5 | N/A | N/A |
| IBIO-101-CHO-afuc | 15.6 | 2.5 | 43.1 | 12.3 | N/A | N/A |
| IBIO-101-plant-WT | 16.0 | 3.3 | 43.9 | 8.8 | N/A | N/A |
| IBIO-101-plant-afuc | 17.4 | 3.2 | 42.4 | 9.8 | N/A | N/A |

TABLE 2A

SUDHL-1 cell binding assay: summary table.

| | EC50 (ng/ml, n ≥ 6) | |
|---|---|---|
| SUDHL-1 | Average | SD |
| hIgG1 Isotype | N/A | N/A |
| Daclizumab | 149.8 | 49.3 |
| IBIO-101-CHO-WT | 123.1 | 26.2 |
| IBIO-101-CHO-afuc | 125.9 | 39.9 |
| IBIO-101-plant-WT | 126.3 | 39.71 |
| IBIO-101-plant-afuc | 123.4 | 38.12 |

TABLE 2B iTreg cell binding assay: summary table.

iTreg

EC50 (ng/ml, n = 3)

| | Average | SD |
|---|---|---|
| hIgG1 Isotype | NA | NA |
| Daclizumab | 178.45 | 24.96 |
| IBIO-101-CHO-WT | 222.63 | 44.59 |
| IBIO-101-CHO-afuc | 218.73 | 40.50 |
| IBIO-101-plant-WT | 235.07 | 63.88 |
| IBIO-101-plant-afuc | 217.73 | 83.94 |

TABLE 3A

SUDHL-1/NFAT CD16 ADCC reporter assay: summary table.

EC50 (ng/ml, n ≥ 6)

| SUDHL-1/NFAT CD16 | Average | SD |
|---|---|---|
| hIgG1 Isotype | N/A | N/A |
| Daclizumab | 137.0 | 62.01 |
| IBIO-101-CHO-WT | 84.5 | 26.8 |
| IBIO-101-CHO-afuc | 7.2 | 3.8 |
| IBIO-101-plant-WT | 32.5 | 11.3 |
| IBIO-101-plant-afuc | 8.9 | 2.99 |

TABLE 3B $iT_{reg}$/NFAT CD16 ADCC reporter assay: summary table

EC50 (ng/ml, n ≥ 3)

| $iT_{reg}$/NFAT CD16 | Average | SD |
|---|---|---|
| hIgG1 Isotype | NA | NA |
| Daclizumab | 125.67 | 74.45 |
| IBIO-101-CHO-WT | 53.77 | 15.43 |
| IBIO-101-CHO-afuc | 4.71 | 3.60 |
| IBIO-101-plant-WT | 30.31 | 13.90 |
| IBIO-101-plant-afuc | 7.14 | 6.23 |

TABLE 4

IL-2 reporter HEK293 pSTAT5 assay: summary table.

EC50 (ng/ml, n ≥ 3)

| | Average | SD |
|---|---|---|
| IL-2 | 0.11 | 0.06 |
| Daclizumab | 3.42 | 1.62 |
| IBIO-101-CHO-WT | 0.17 | 0.07 |
| IBIO-101-CHO-afuc | 0.17 | 0.067 |
| IBIO-101-plant-WT | 0.21 | 0.115 |
| IBIO-101-plant-afuc | 0.17 | 0.089 |

Figure 17A:
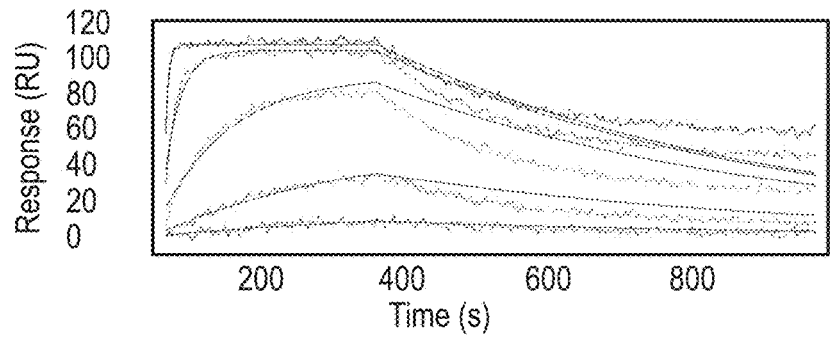
FIGS. 17A to 17E show the binding of a monoclonal antibody (IBIO-101) that bind to CD25 characterized using a Carterra LSA, FIG. 17A IBIO-101 made in CHO cells wild-type Ab, FIG. 17B IBIO-101 made in plant cells wild-type Ab, FIG. 17C IBIO-101 made in CHO cells afucosylated, FIG. 17D IBIO-101 made in plant cells afucosylated, FIG. 17E Daclizumab.
Figure 17B:
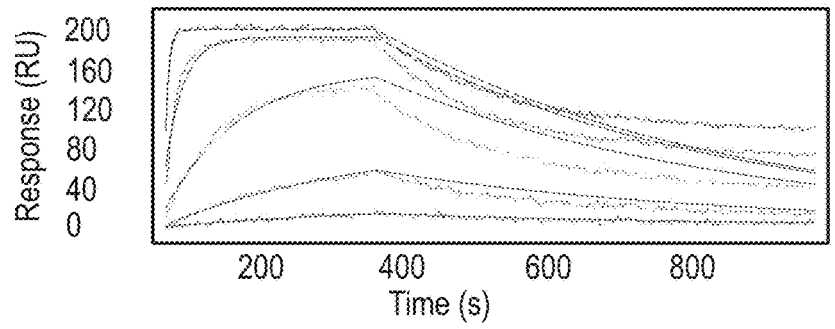
Figure 17C:
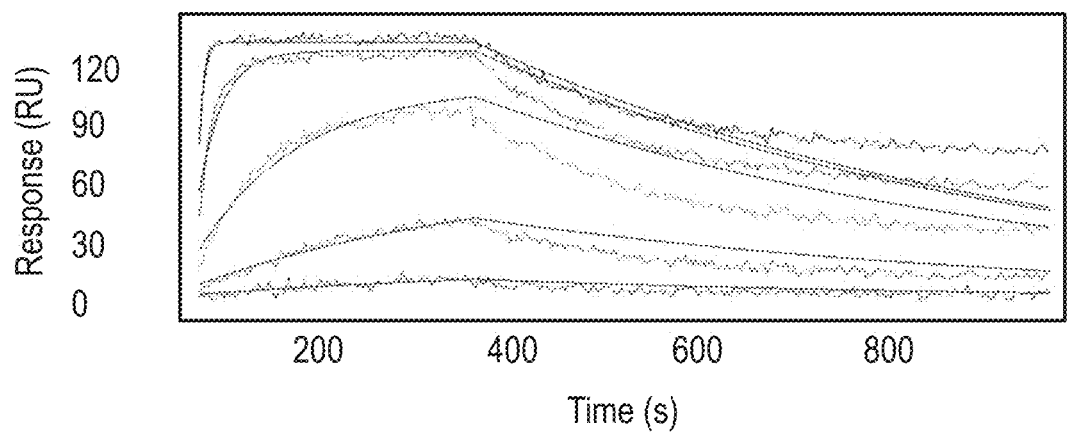
Figure 17D:
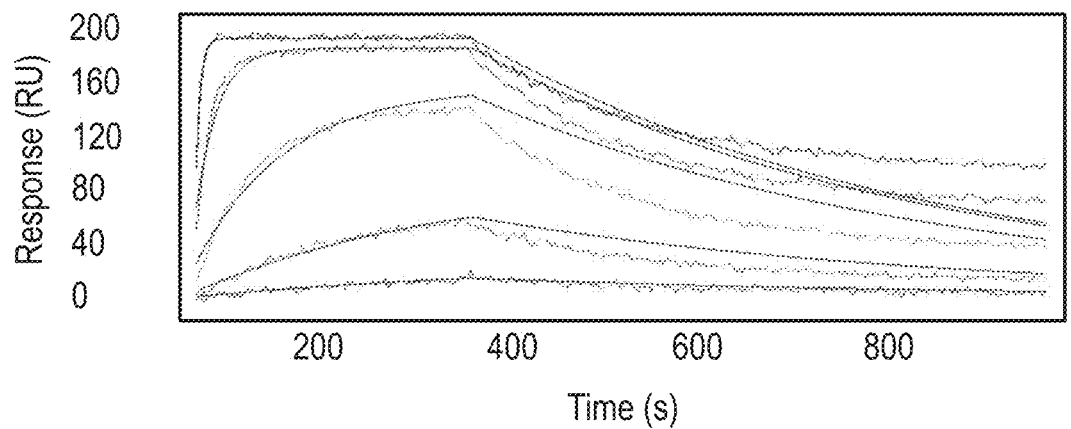
Figure 17E:
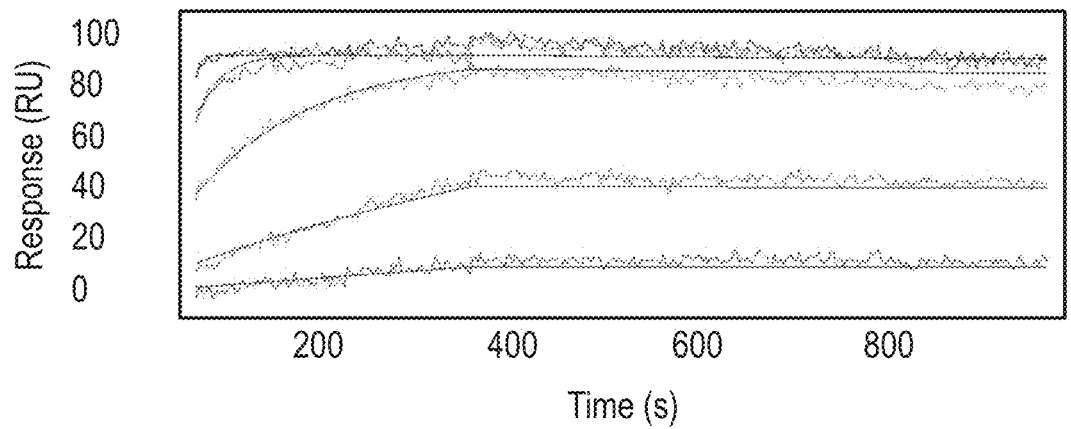

FIGS. 17A to 17E show the binding of a monoclonal antibody (IBI-01) that bind to CD25 characterized using a Carterra LSA, FIG. 17A IBIO-101 made in CHO cells wild-type Ab, FIG. 17B IBIO-101 made in plant cells wild-type Ab, FIG. 17C TIO-101 made in CHO cells afucosylated, FIG. 17D IBIO-101 made in plant cells afucosylated, FIG. 17E Daclizumab.

TABLE 5

IBIO-101 Binding Kinetic Profiles are Similar in CHO and Plant Expression System.

| Antibody | $K_{on}$ (M$^{-1}$ s$^{-1}$) | $K_{off}$ (s$^{-1}$) | $K_D$ (nM) | $K_D$ SD (nM) |
|---|---|---|---|---|
| IBIO-101-CHO WT | 4.71E+05 | 1.92E-03 | 4.10 | 0.37 |
| IBIO-101-CHO afuc | 4.99E+05 | 1.191E-03 | 3.9 | 1.03 |
| IBIO-101-Plant WT | 4.85E+05 | 1.196E-03 | 4.20 | 0.69 |
| IBIO-101-Plant afuc | 4.92E+05 | 2.07E-03 | 4.27 | 1.27 |
| Daclizumab | 4.15E+05 | 7.40E-05 | 0.18 | 0.07 |

Figure 13:
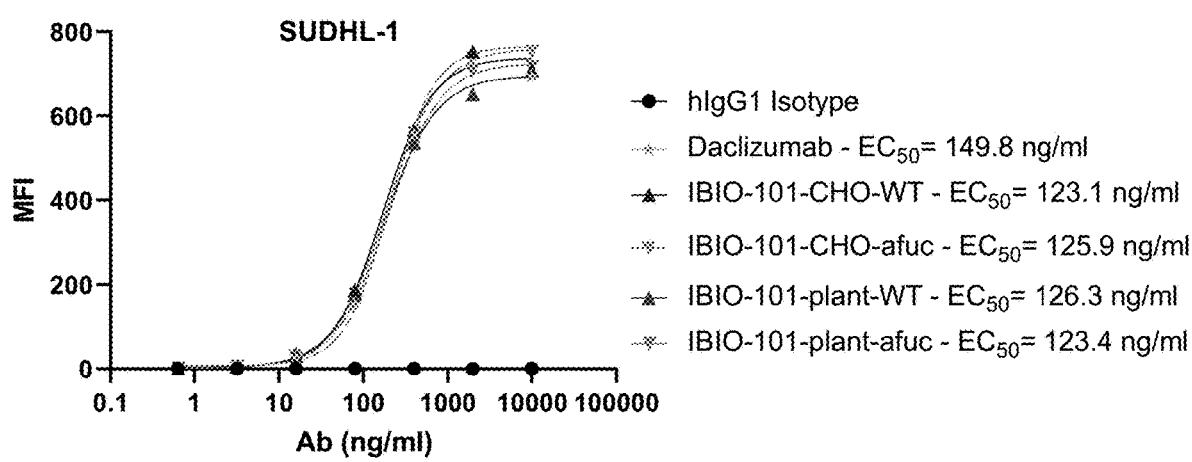
FIG. 13 shows that IBIO-101 exhibits strong binding to CD25 endogenously expressed on SUDHL-1 human lymphoma cell line.
Figure 18:
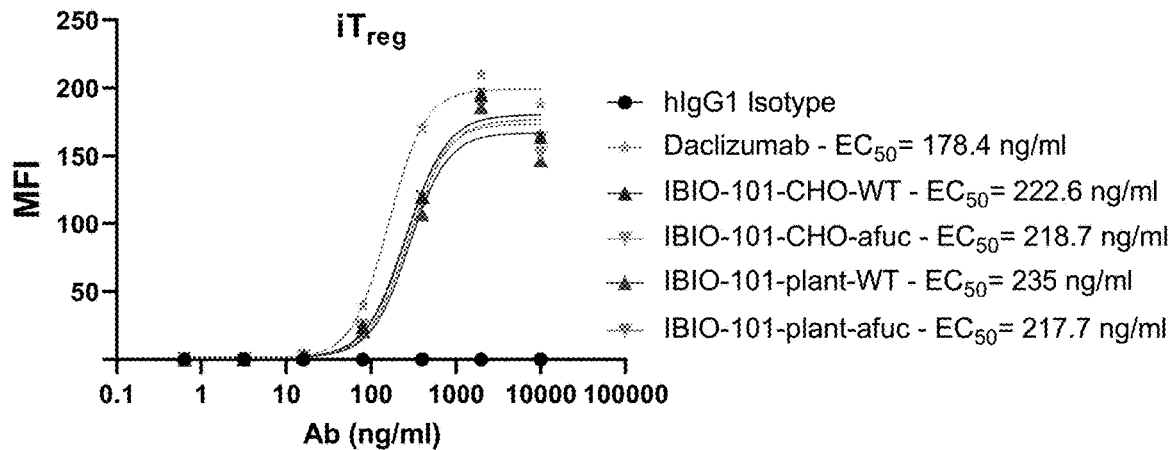
FIG. 18 shows that IBIO-101 exhibits strong binding to CD25 endogenously expressed on induced human $T_{reg}$ ($iT_{reg}$).

FIGS. 13 and 18 show that TIO-101 exhibit strong binding to CD25 endogenously expressed on SUDHL-1 human lymphoma cell line (FIG. 13) and induced human $T_{reg}$ ($iT_{reg}$) (FIG. 18). FACS analysis showing WT and afucosylated IBIO-101 molecules made in CHO and plants and Daclizumab binding to CD25 on SUDHL-1 and $iT_{reg}$. Values plotted are Median Fluorescent Intensity. $EC_{50}$ values are averages of n≥3 experiments.

Figure 14:
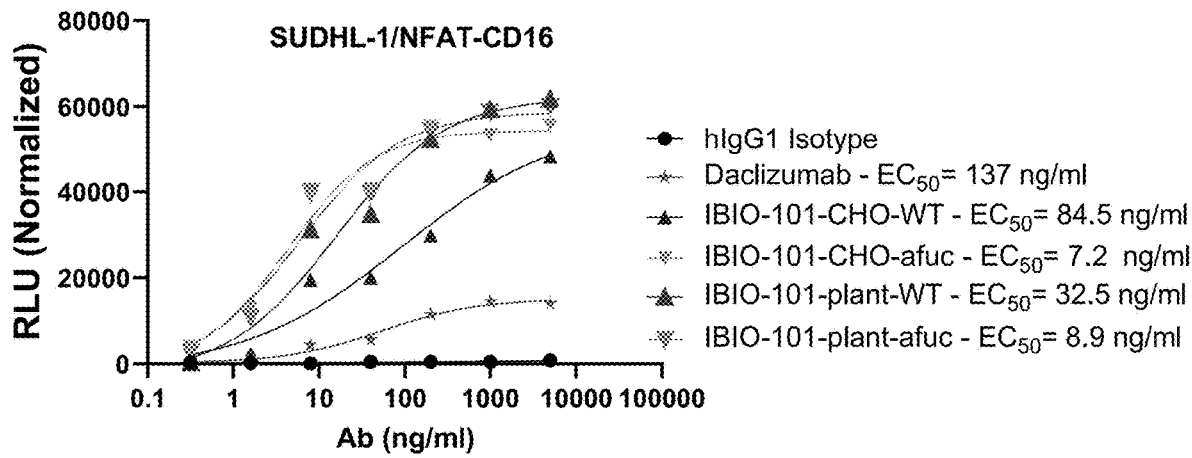
FIG. 14 shows that CHO and plant afucosylated IBIO-101 similarly enhanced ADCC potency against the SUDHL-1 human lymphoma cell line.
Figure 19:
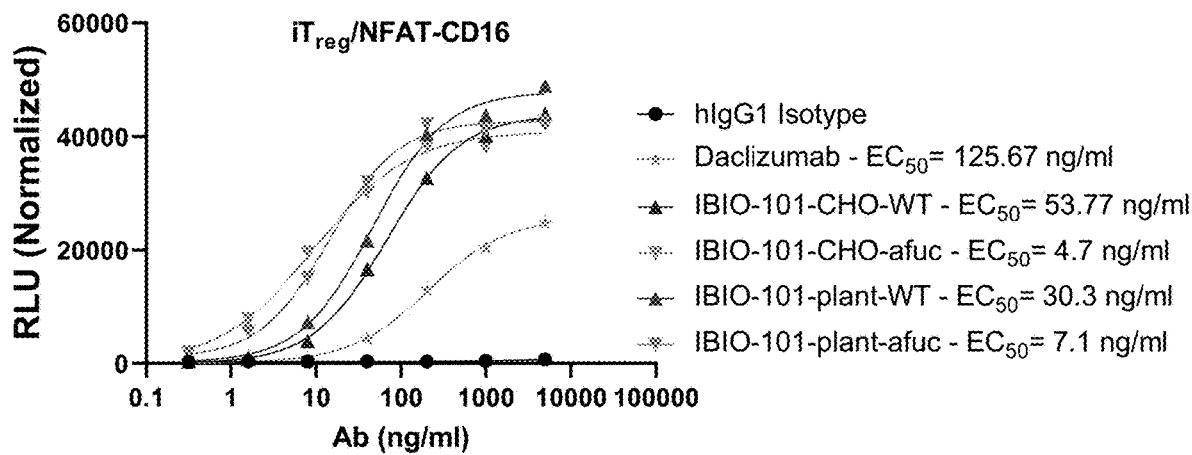
FIG. 19 shows that CHO and plant afucosylated IBIO-101 similarly enhanced ADCC potency against induced human $T_{reg}$ ($iT_{reg}$)

FIGS. 14 and 19 show that CHO and plant afucosylated IBIO-101 similarly enhanced ADCC potency against SUDHL-1 human lymphoma cell line (FIG. 14) and induced human $T_{reg}$ ($iT_{reg}$) (FIG. 19). NFAT CD16 Jurkat ADCC reporter cell line is used to show ADCC potency by WT and afucosylated IBIO-101 made in CHO and plants and Daclizumab against CD25 expressing SUDHL-1 and $iT_{reg}$ target cells. $EC_{50}$ values are averages of n≥3 experiments.

Figure 15:
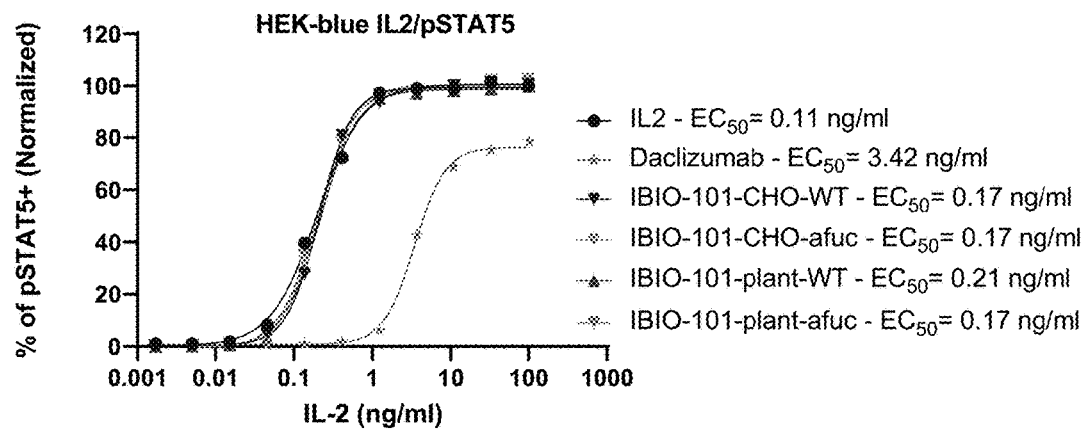
FIG. 15 is a graph that shows that the IBIO-101 molecules do not inhibit IL2/STAT5 signaling pathway.
Figure 16:
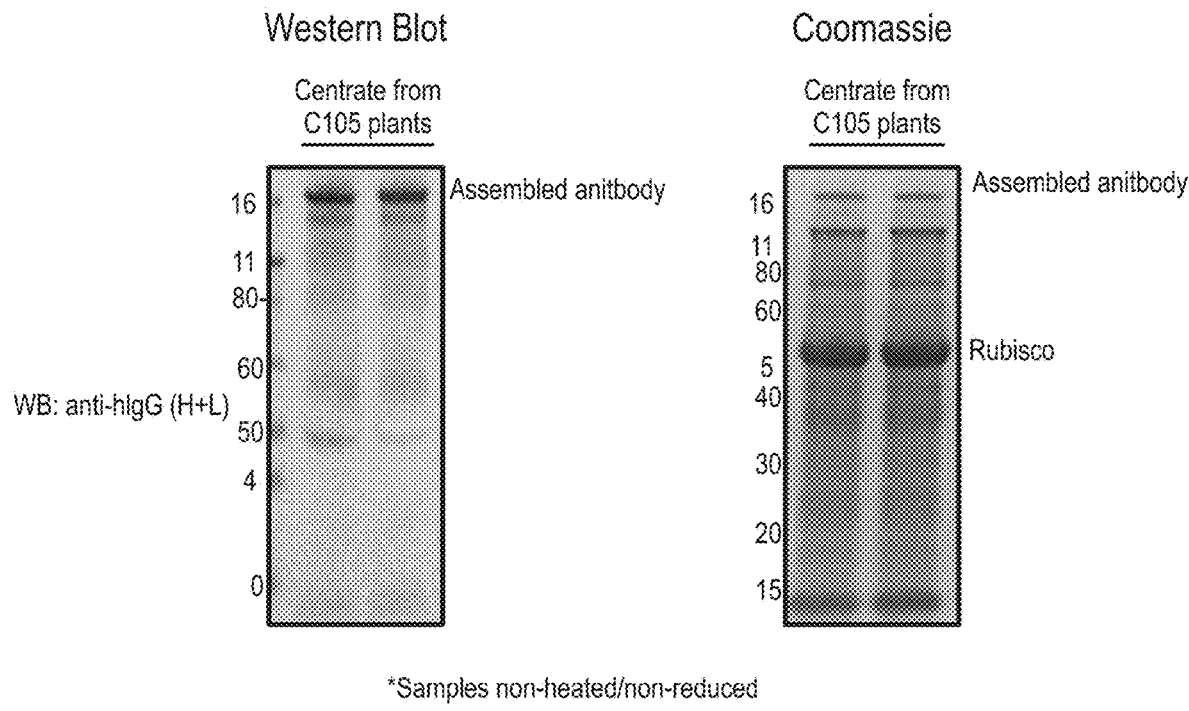
FIG. 16 shows a Western blot and a Coomasie blue stained gel of the antibody of the present invention, the anti-CD25 antibody made in a wild-type plant is also referred to as SD-889825-PW-A (IBIO-101, wild type Plant), and the anti-CD25 antibody manufactured in the c-105 strain is SD-889825-PC-A (IBIO-101, c-105 Plant Afucosylated).

FIG. 15 is a graph that shows that the IBIO-101 molecules do not inhibit IL2/STAT5 signaling pathway. FACS analysis showing the dose-dependent activation of STAT5 by IL2 or in presence of Daclizumab, IBIO-101-CHO-WT, IBIO-101-CHO-afuc, IBIO-101-plant-WT, or IBIO-101-plant-afuc in HEK blue human IL2R overexpressing cell line. STAT5 activation is measured by staining for phosphorylated STAT5 protein. The fucosylated and afucosylated IBIO-101 molecules that are produced in CHO or plant shows no inhibitory effect on IL2/STAT5 signaling while Daclizumab significantly inhibit STAT5 activation by IL2. $EC_{50}$ values are averages of n≥3 experiments.

Figure 20:
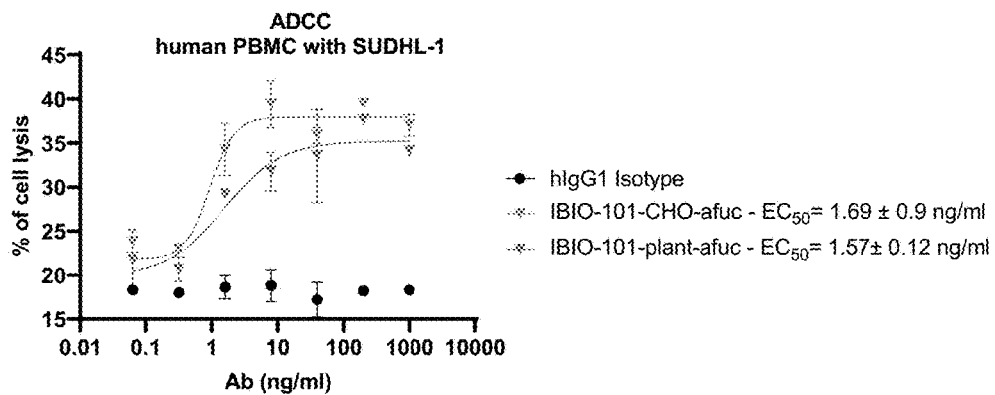
FIG. 20 shows that afucosylated IBIO-101 exhibits strong SUDHL-1 human lymphoma cell killing.
Figure 21:
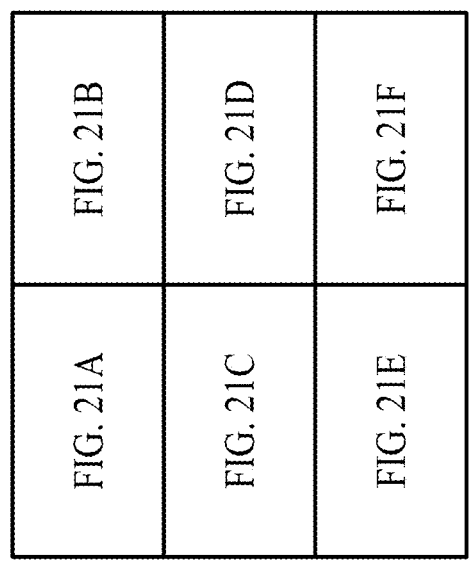
FIGS. 21A-21F show that IBIO-101 molecules show high binding to CD25 expressing SUDHL-1 and induced human $T_{reg}$ ($iT_{reg}$) cells but low binding to other primary immune cells.
Figure 21A:
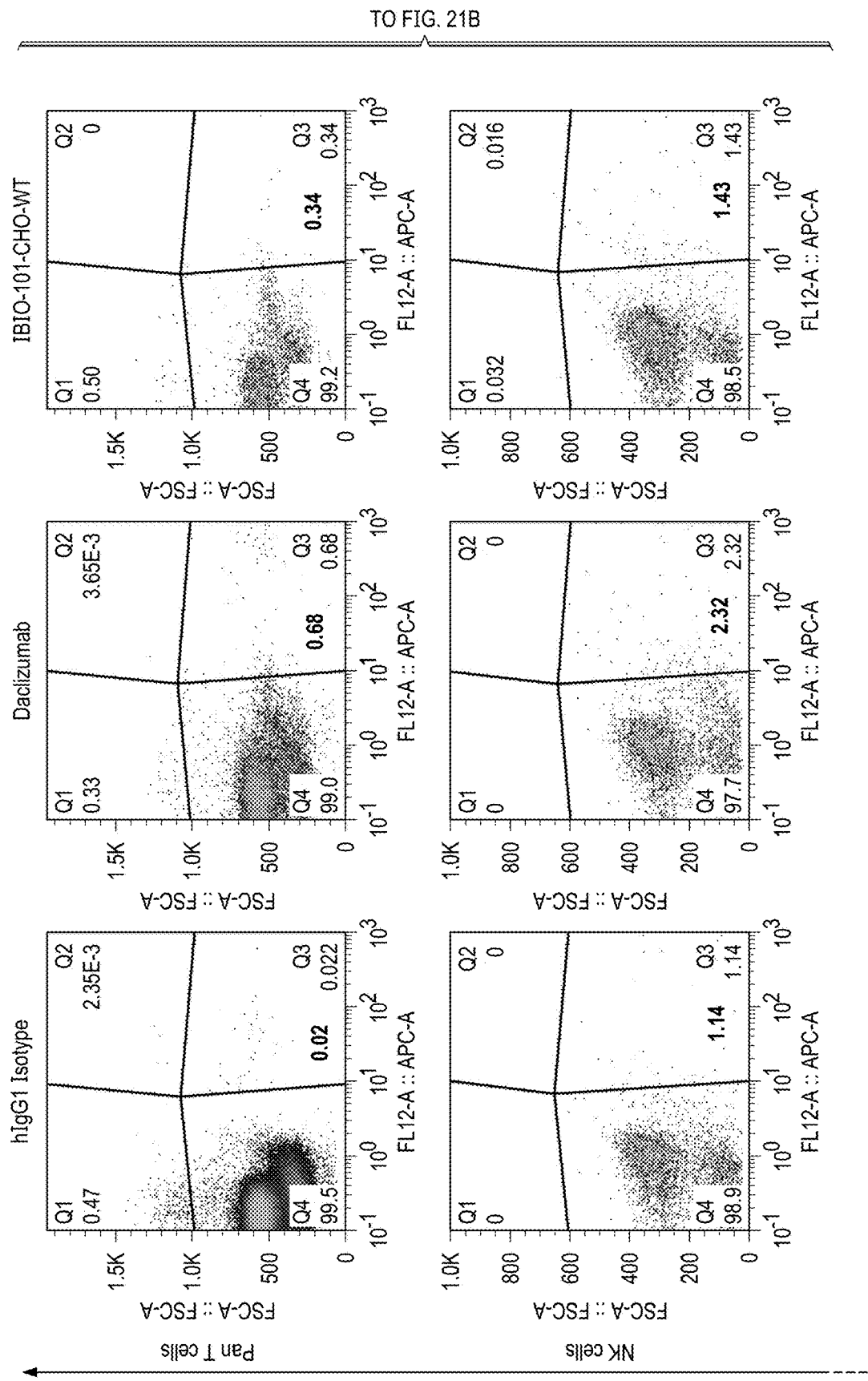
Figure 21B:
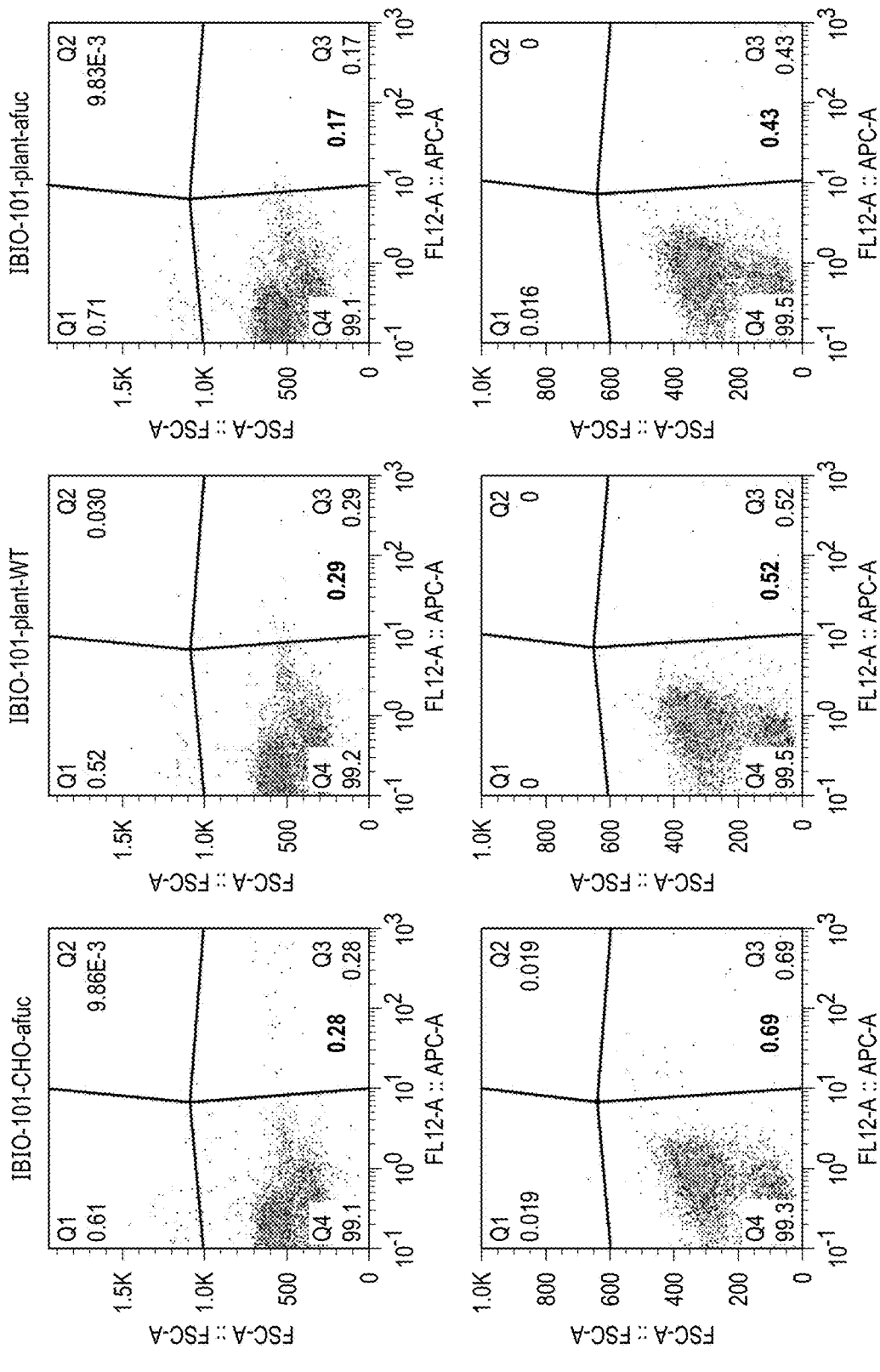
Figure 21D:
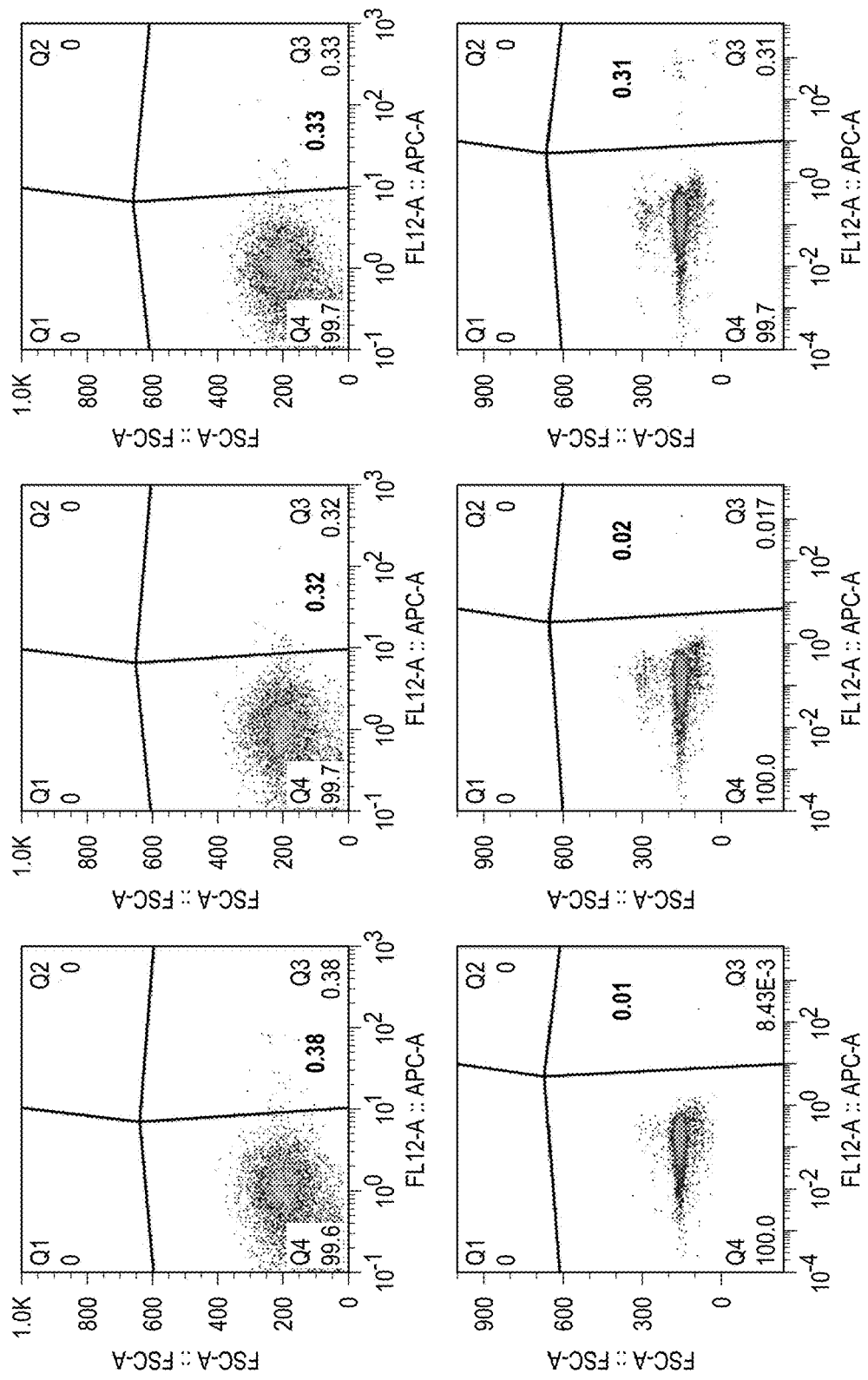

FIG. 20 shows that afucosylated IBIO-101 exhibits strong SUDHL-1 human lymphoma cell killing. FACS analysis showing cell death triggered by CHO or plant made afucosylated IBIO-101 against CD25 expressing SUDHL-1 target cells and human PBMC as effector cells. Cell cytotoxicity was measured by live/dead BV510 dye staining of CFSE-stained target cells. $EC_{50}$ values are averages of n=3 experiments.

FIGS. 21A-21F show that IBIO-101 molecules show high binding to CD25 expressing SUDHL-1 and induced human $T_{reg}$ ($iT_{reg}$) cells but low binding to other primary immune cells. FACS analysis showing WT fucosylated and afucosylated IBIO-101 molecules made in CHO and plants and Daclizumab with high levels of binding to human lymphoma SUDHL-1 cells and $iT_{reg}$ cells. Pan T cell, NK cell, monocyte, and CD8+ effector T cells demonstrated low levels of binding to IBIO-101 molecules. Representative FACS plots shown with Forward Scatter (FSC) versus CD25 in indicated cell types, with percentage of binding to human IgG1 isotype, IBIO-101 molecules, or Daclizumab indicated on each plot; n=2.

Figure 22:
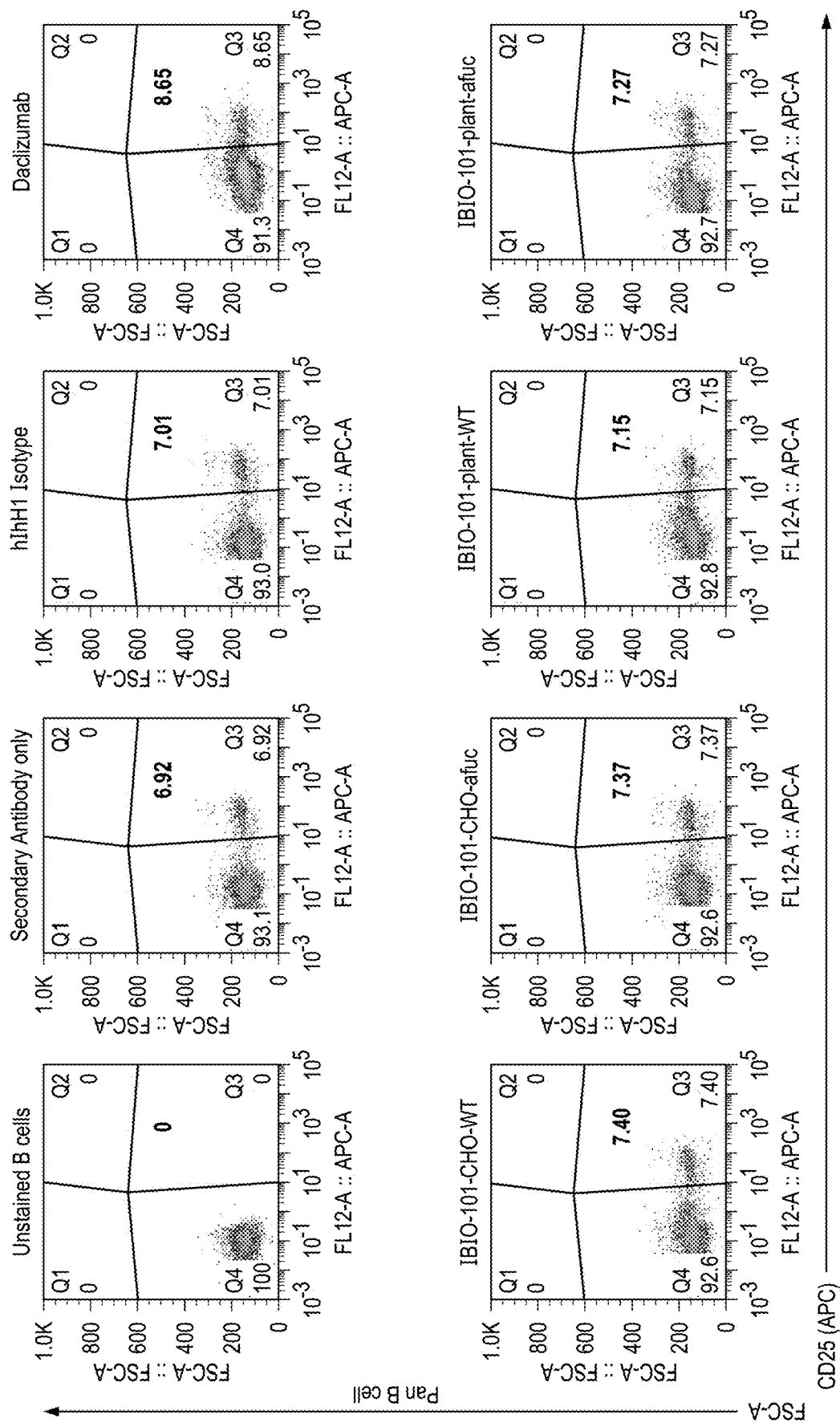
FIG. 22 shows that IBIO-101 molecules do not show specific binding to Pan B cells. FACS analysis showing WT fucosylated and afucosylated IBIO-101 molecules made in CHO and plants and Daclizumab binding similarly to Pan B cells.

FIG. 22 shows that IBIO-101 molecules do not show specific binding to Pan B cells. FACS analysis showing WT fucosylated and afucosylated IBIO-101 molecules made in CHO and plants and Daclizumab binding similarly to Pan B cells. The level of binding signal is comparable to staining with secondary antibody only. Representative FACS plots shown with Forward Scatter (FSC) versus CD25 in pan B cells, with percentage of binding to human IgG1 isotype, IBIO-101 molecules, or Daclizumab indicated on each plot; n=2.

TABLE 6 iT$_{reg}$ depletion assay: summary table.

| | EC50 (ng/ml, n = 3) | |
| --- | --- | --- |
| | Average | SD |
| hIgG1 Isotype | N/A | N/A |
| Daclizumab | N/A | N/A |
| IBIO-101-CHO-afuc | 7.09 | 4.96 |
| IBIO-101-plant-afuc | 12.01 | 7.51 |

Figure 23A:
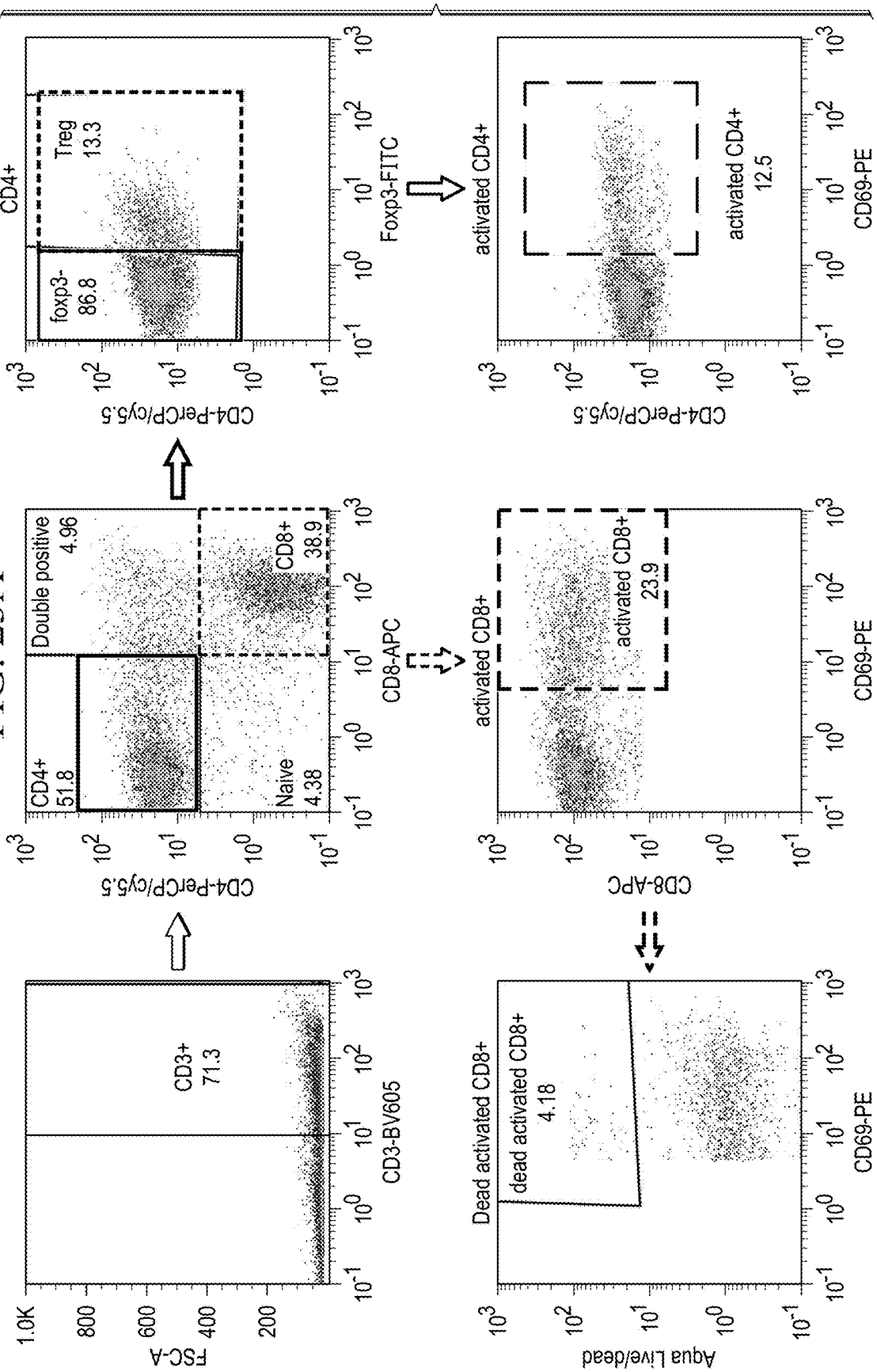
FIGS. 23A-23B show the $iT_{reg}$ depletion assay gating strategy.
Figure 23B:
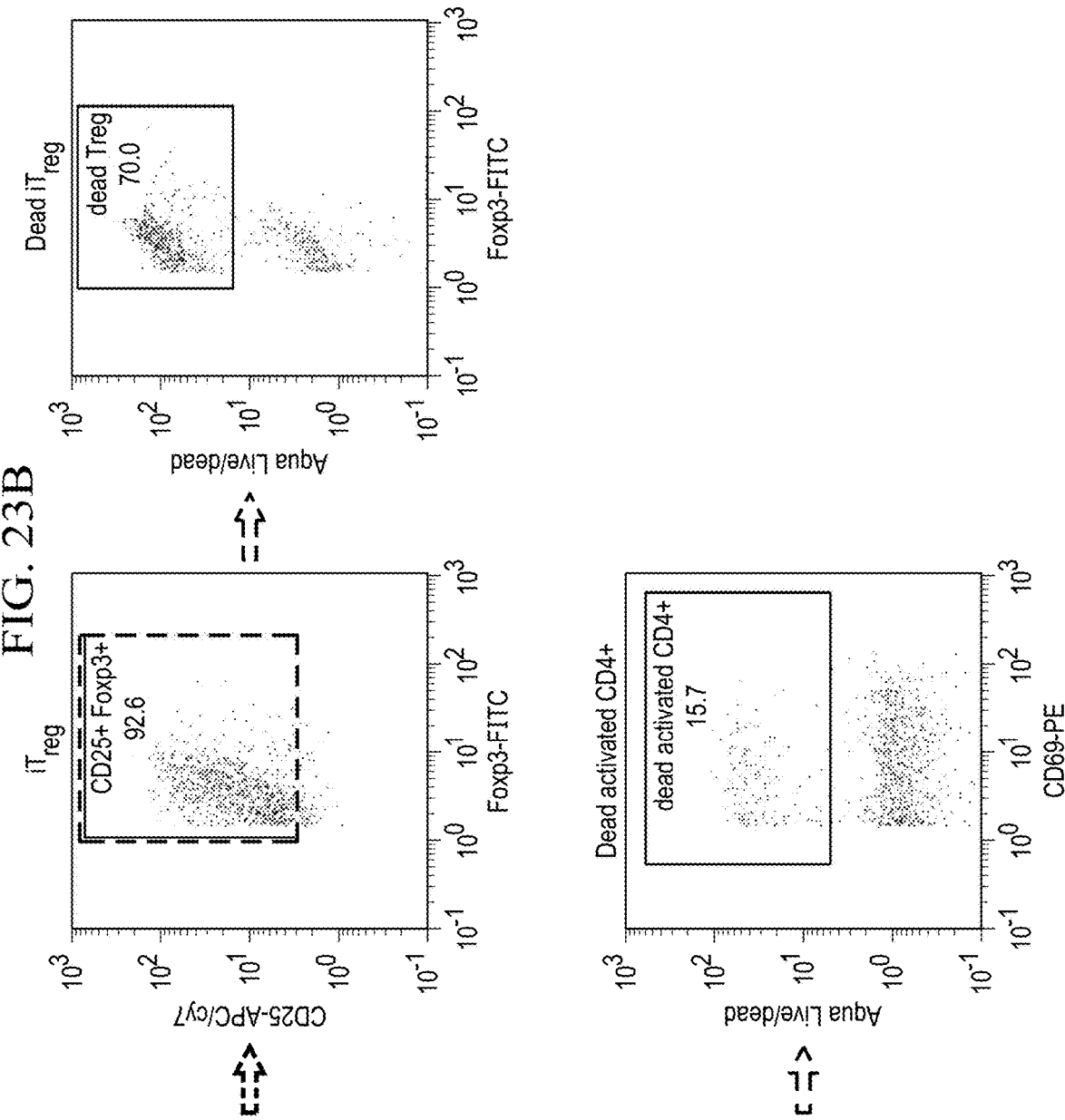

FIGS. 23A-23B show the iTreg depletion assay gating strategy.

Figure 24:
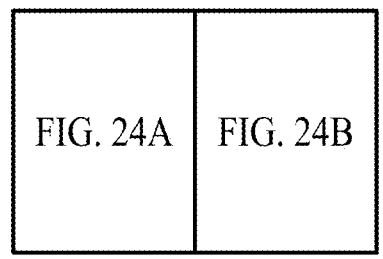
FIGS. 24A-24B show the $iT_{reg}$ depletion of representative FACS plots showing the percent cytotoxicity from treatment with hIgG1 isotype, Daclizumab, IBIO-101-plant-afuc and IBIO-101-CHO-afuc in $iT_{reg}$, activated CD4+ and activated CD8+ cells.
Figure 24A:
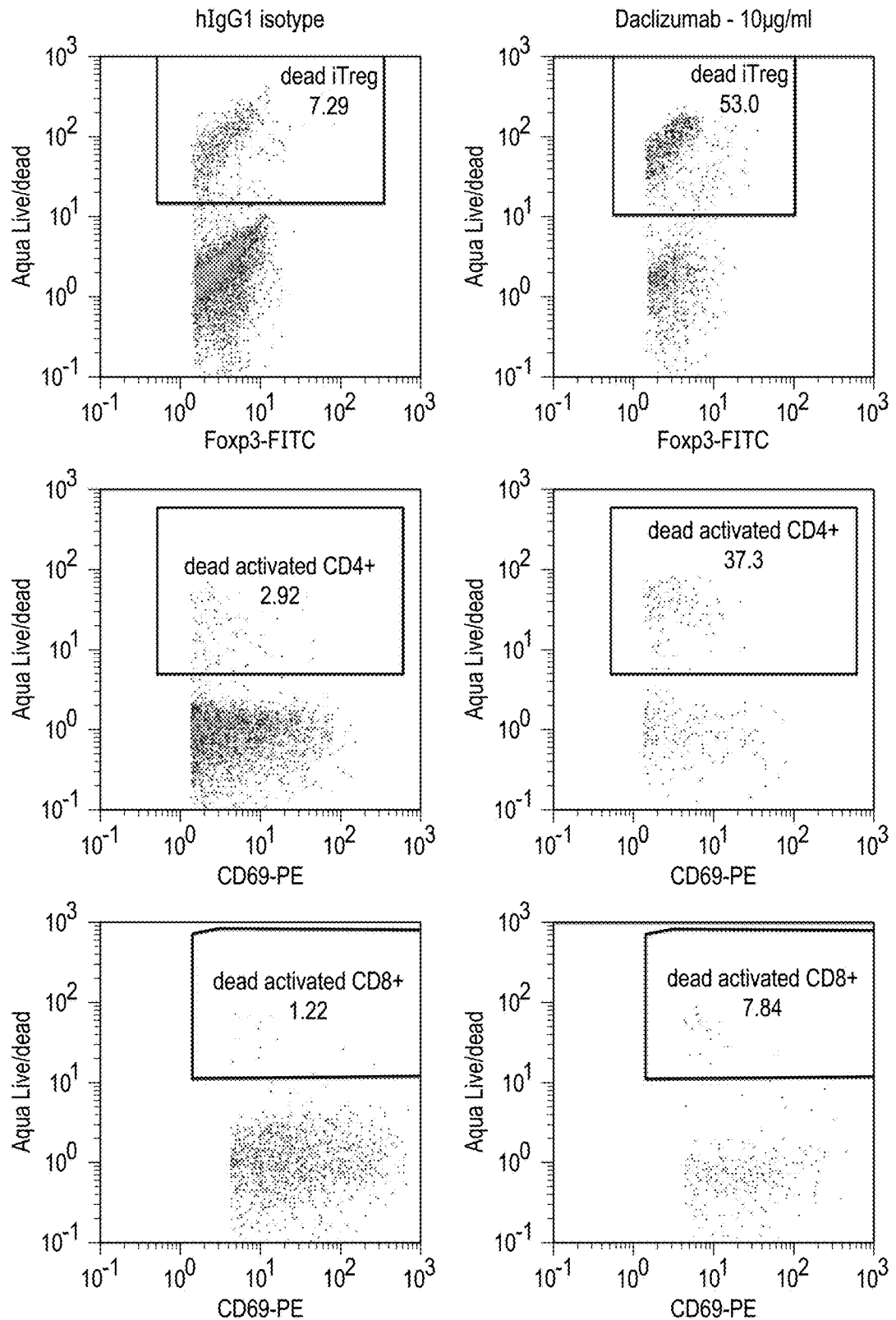
Figure 24B:
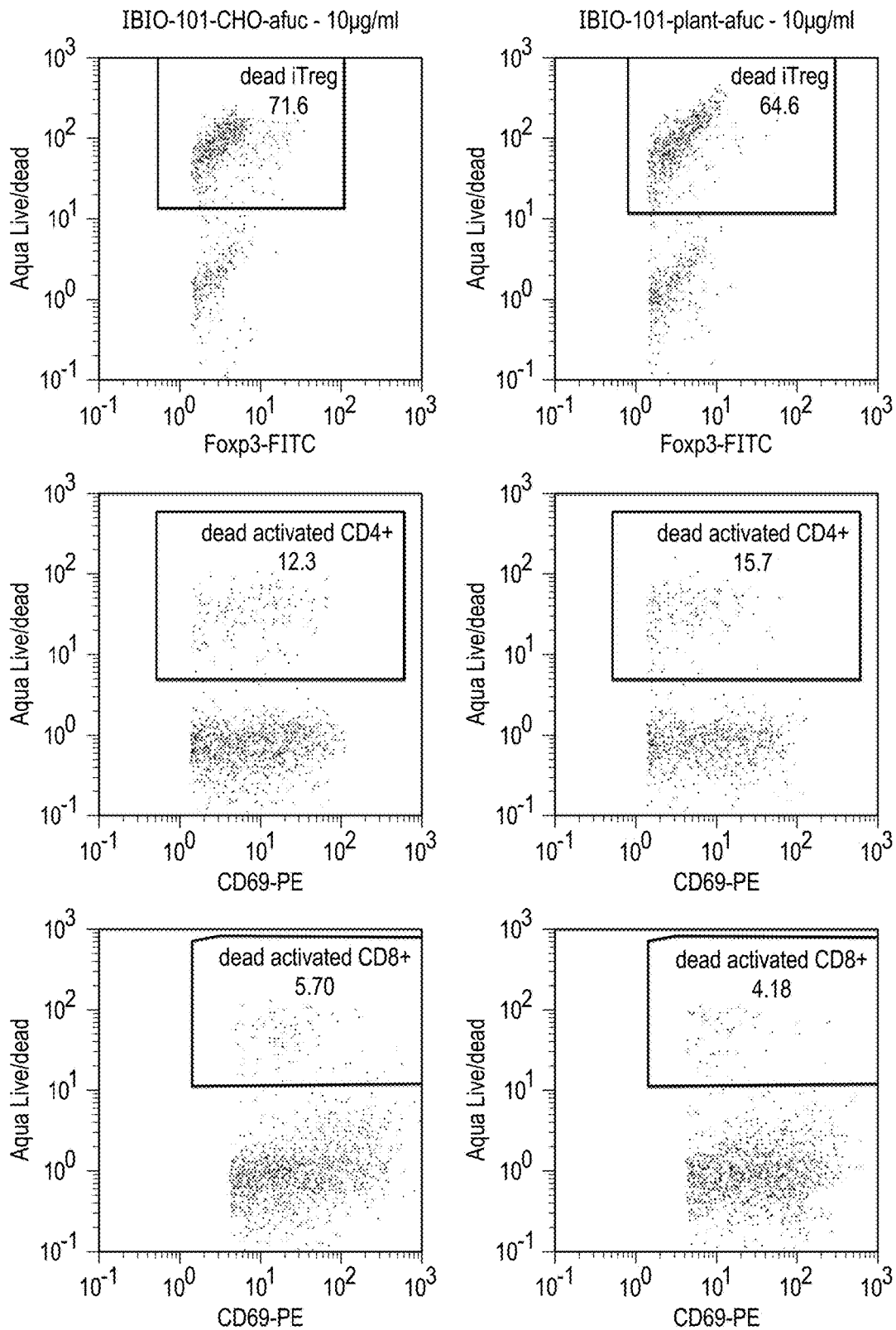

FIGS. 24A-24B show the iT$_{reg}$ depletion of representative FACS plots showing the percent cytotoxicity from treatment with hIgG1 isotype, Daclizumab, IBIO-101-plant-afuc and IBIO-101-CHO-afuc in iT$_{reg}$, activated CD4+ and activated CD8+ cells.

Figure 25A:
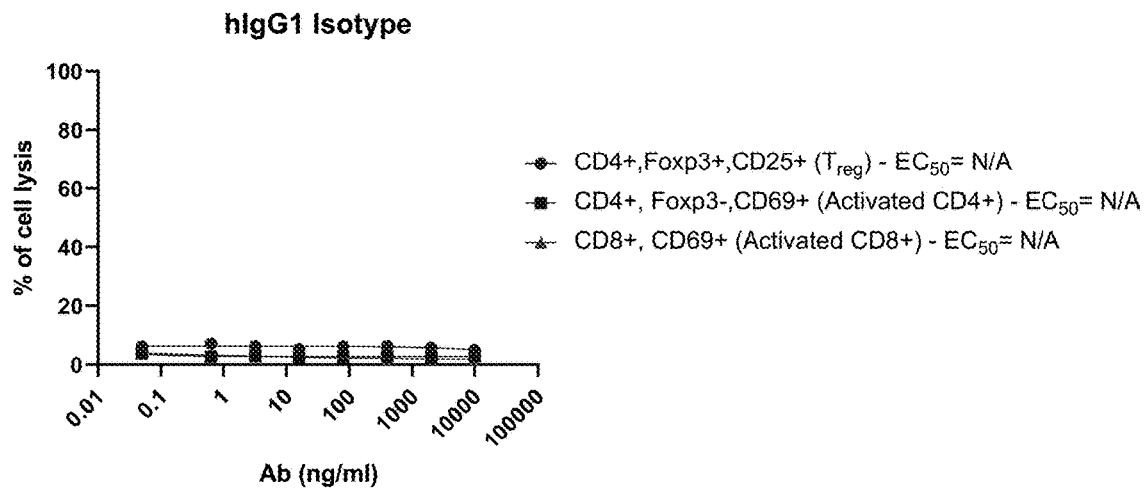
FIGS. 25A to 25D show the selective depletion of induced human $T_{reg}$ ($iT_{reg}$) after iBio-101 treatment.
Figure 25B:
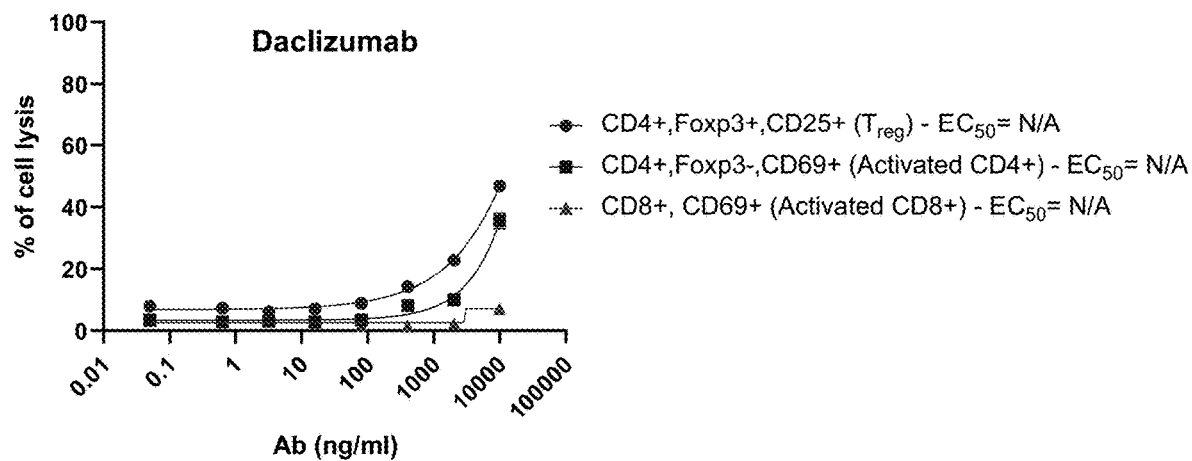
Figure 25C:
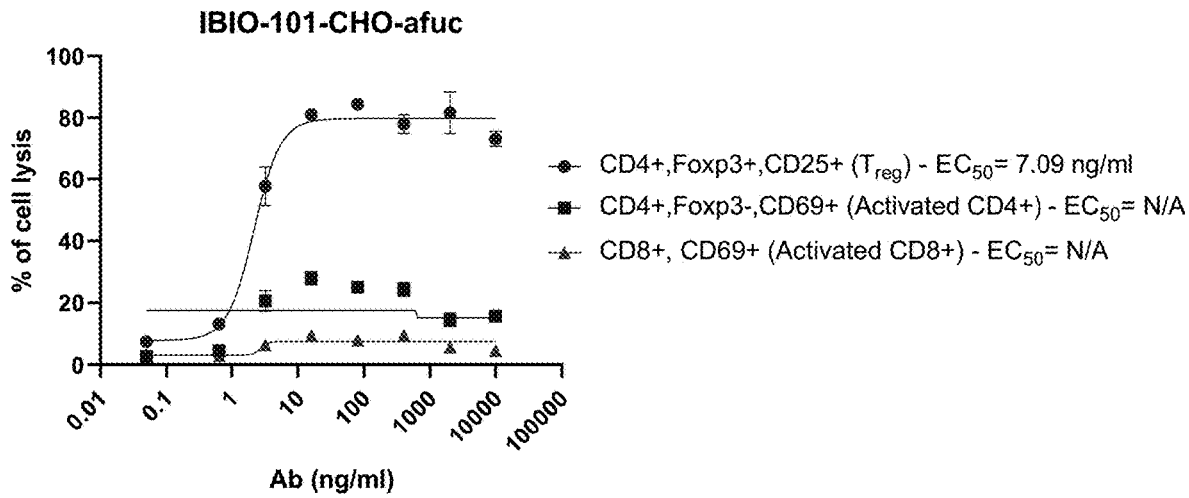
Figure 25D:
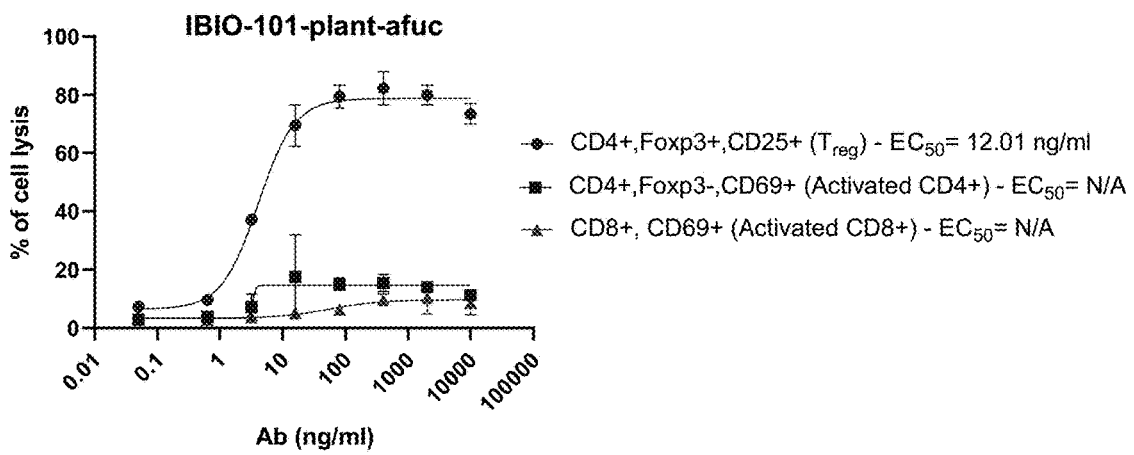

FIGS. 25A to 25D show the selective depletion of induced human T$_{reg}$ (iT$_{reg}$) after iBio-101 treatment. FACS analysis showing human IgG1 isotype and Daclizumab does not significantly deplete iT$_{reg}$, activated CD4+ and CD8+ cells at 3 days post-treatment in culture (FIGS. 25A and 25B, respectively). However, afucosylated iBio-101 molecules made in CHO and plants strongly induced iT$_{reg}$ lysis, with minimal levels of cytotoxicity observed in activated CD4+ and CD8+ cells within the same treatment period (FIGS. 25C and 25D, respectively).

Tg-hCD25 mice. The sequences encoding the extracellular domain of human IL2RA were inserted to replace the sequences encoding the extracellular domain of murine IL2RA. The genotype of the mice in this study were homozygotes (IL2RA$^{human/human}$). Tg-hCD25 mice intraperitoneal (IP) administration with 2.5 mpk of IBIO-101-plant-afuc. Blood samples were collected post administration at 5, 15, + mins, 1, 2, 4 and 8 hours, daily from Day 1 to Day 7, every other day from Day 7 to 17, twice a week from Day 17 to Day 28. IBIO-101-plant-afuc demonstrated half-life of ~47 hours, with T$_{max}$ at 2 hours and C$_{max}$ at 10.1 ug/ml in Tg-hCD25 mice. 2.5 mpk twice weekly intraperitoneal administration will provide EC$_{90}$ coverage of human PBMC ADCC activity. Thus, twice weekly IP injection was implemented for efficacy study in Tg-hCD25 mice.

Figure 26:
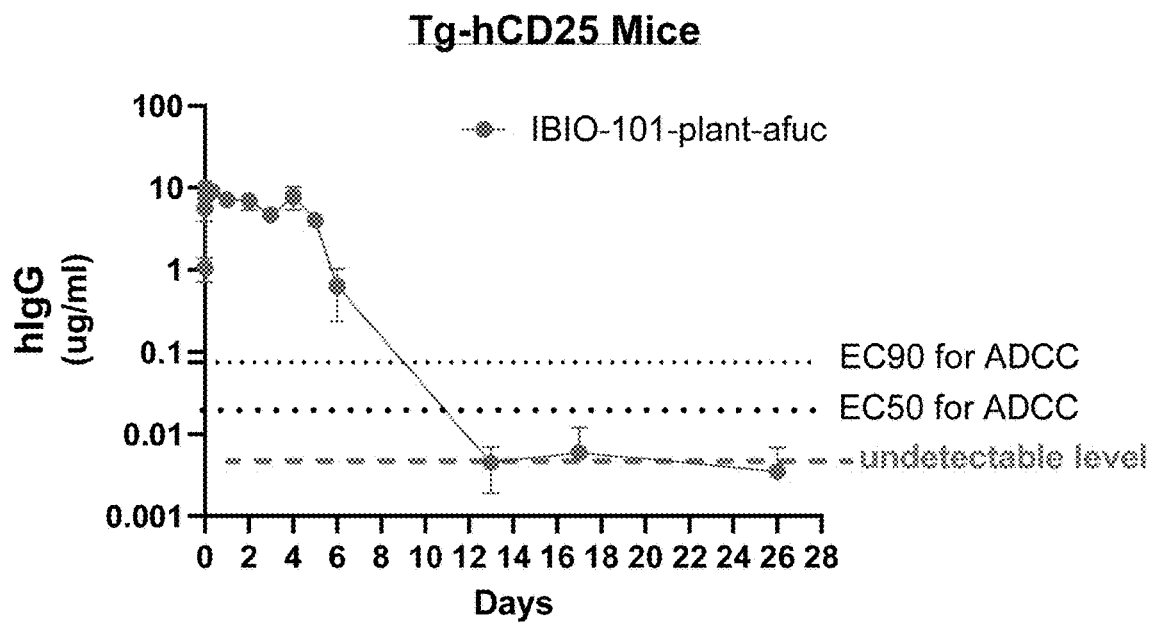
FIG. 26 is a graph that shows the iBio-101 Pharmacokinetic Profile in hCD25 TG Mice.

FIG. 26 is a graph that shows the iBio-101 Pharmacokinetic Profile in hCD25 TG Mice.

Figure 27:
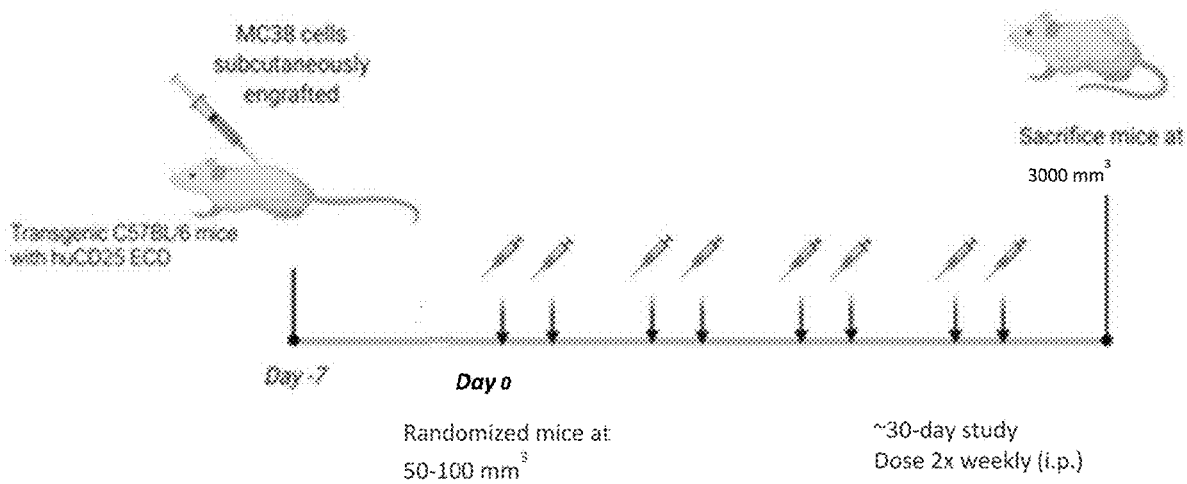
FIG. 27 shows the iBio-101 In Vivo Efficacy Study Design.

FIG. 27 shows the iBio-101 In Vivo Efficacy Study Design. Evaluate IBIO-101-plant and IBIO-101-CHO efficacy against current S.O.C. Investigate IBIO-101 as single agent or in combination with anti-PD-1 antibody. Determine IBIO-101 mechanism of action in immune cells of treated mice.

In vivo Efficacy Evaluation of IBIO-101-plant and IBIO-101-CHO efficacy in the Treatment of Subcutaneous MC38 Colon Carcinoma Models in B-hIL2RA Mice. B-hIL2RA mice were subcutaneously injected with MC38 tumor cells. Approximately 7 days after tumor inoculation, tumor-bearing animals were randomly enrolled into eight study groups when the mean tumor size reaches approximately 50-100 mm$^3$. Each group consists of 7 mice. The initial treatment was administered on the grouping day (Day 0). Test articles were administered twice weekly based on PK study profile. Tumor sizes were measured two times weekly in two dimensions using a caliper, and the volume is expressed in mm$^3$ using the formula: V=0.5 a×b$^2$ where a and b are the long and short dimensions of the tumor, respectively. Blood was collected at day 3, middle point of high range of C$_{max}$ region for immunoprofiling (ratio of T$_{reg}$ to Teff) mechanism of action.

Figure 28:
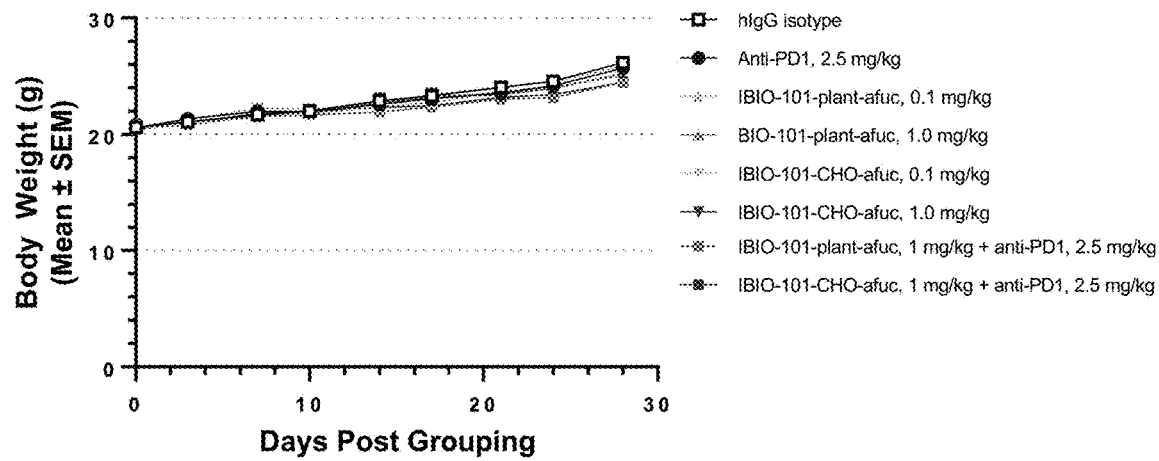
FIG. 28 is a graph that shows the iBio-101 In Vivo Efficacy Study Results—body weight (BW) for all groups.

FIG. 28 is a graph that shows the iBio-101 In Vivo Efficacy Study Results—body weight (BW) for all groups. Animals were randomized in group by weight, then weighed two times per week during the experiment and right before the endpoint of the experiment. No obvious clinical signs and animal death were observed during the experiment, indicating a good tolerance of animals to all test articles. The mean body weight change over time were similar in all treatment group, indicating there is no safety issue for all the treatments.

Figure 29:
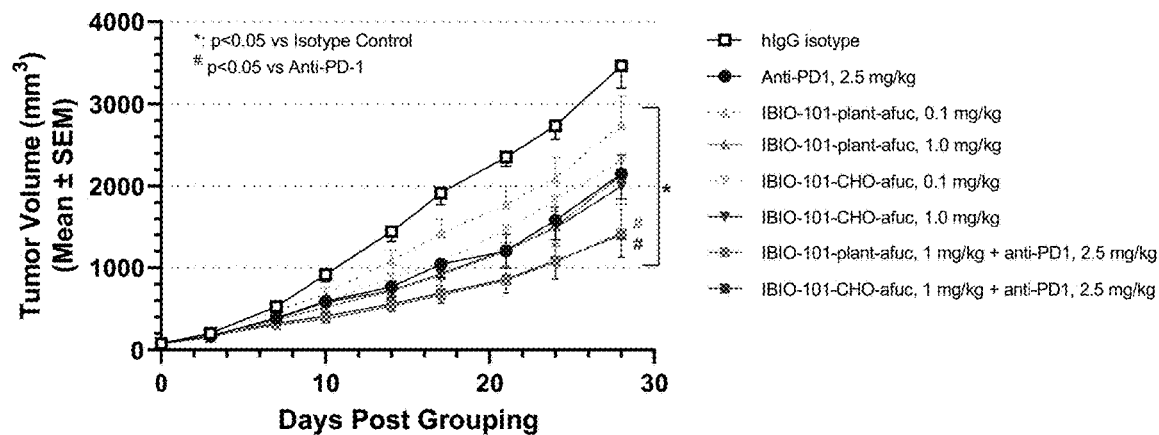
FIG. 29 is a graph that shows the results for iBio-101 In Vivo Efficacy Study Results-Tumor Volume.

FIG. 29 is a graph that shows the results for iBio-101 In Vivo Efficacy Study Results-Tumor Volume. All treatment groups were significantly different from that of isotype vehicle at the terminal day. Both afucosylated Planta and CHO iBio-101 antibody demonstrated a dose-dependent anti-tumor effect. Combination of the afucosylated Planta or CHO iBio-101 (at 1 mpk) with anti-PD1(2.5 mpk) antibody show significantly greater tumor suppression than anti PD-1 antibody alone. Data is Mean±SEM. N=7 per group. * p<0.05 vs. Isotype Control, #: p<0.05 vs. anti-PD1, Two-way ANOVA multiple Comparison followed by Tukey test.

Figure 30A:
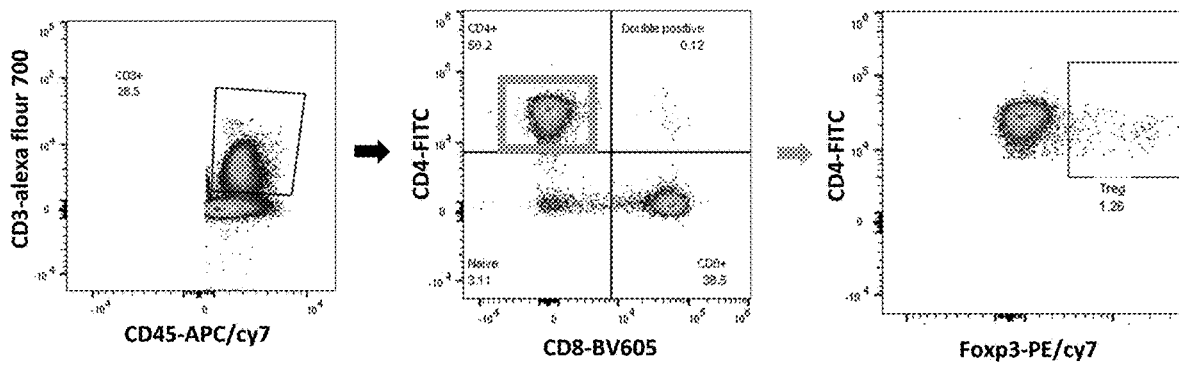
FIG. 30A shows the gating strategy for Tregs in an Efficacy Study—Day 3 blood sample FACS analysis.
Figure 30A:
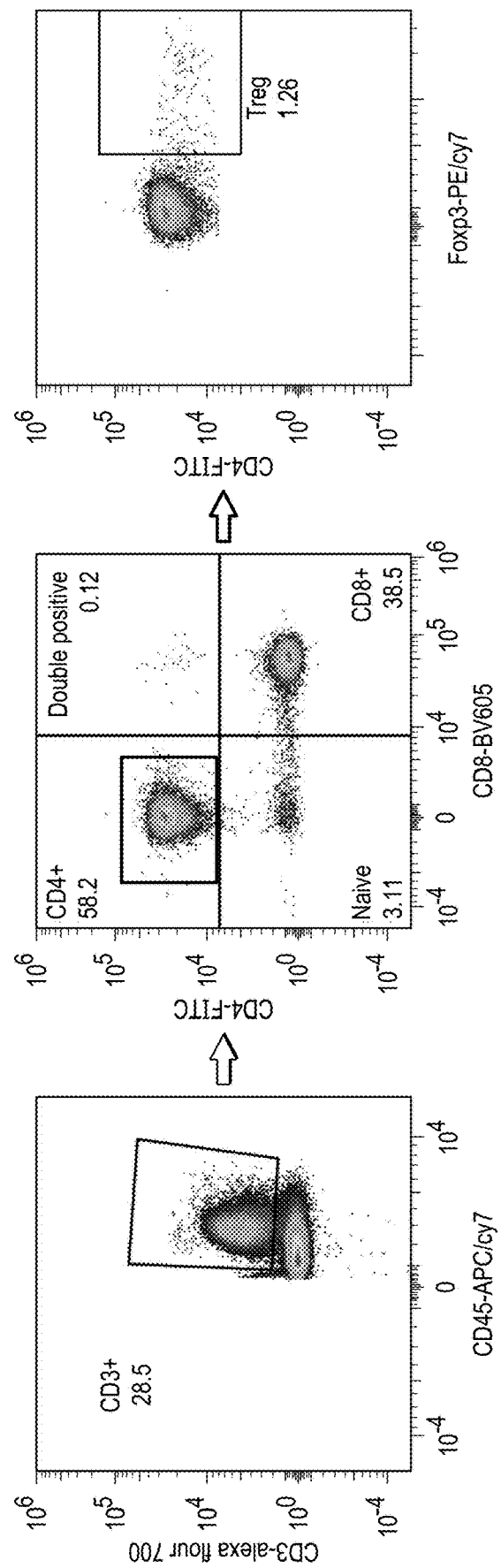
Figure 30B:
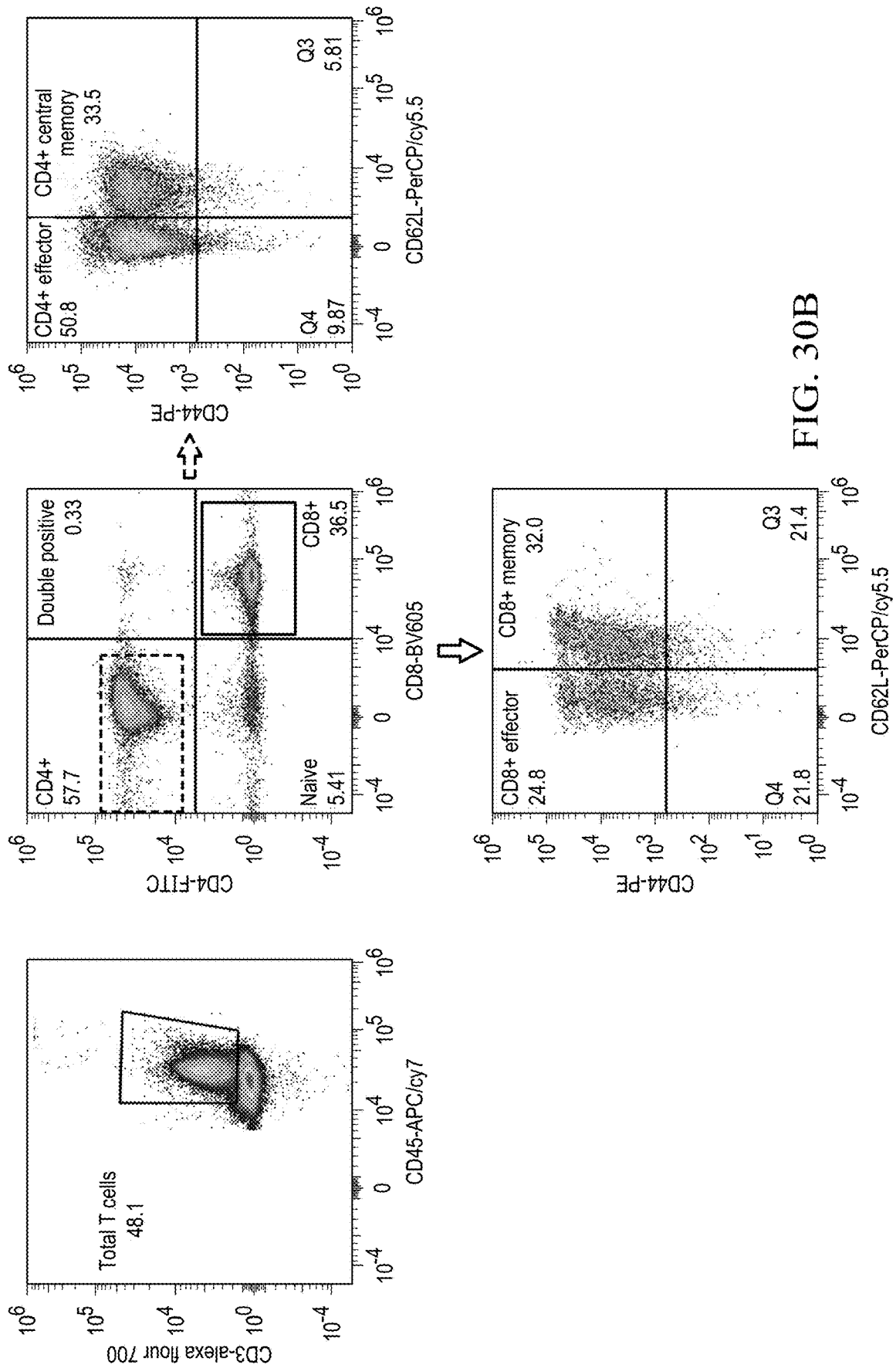
FIG. 30B shows the gating strategy for CD4+ and CD8+ effector cells in an Efficacy Study—Day 3 blood sample FACS analysis.

FIG. 30A shows the gating strategy for Tregs in an Efficacy Study—Day 3 blood sample FACS analysis. FIG. 30B shows the gating strategy for CD4+ and CD8+ effector cels in the Efficacy Study—Day 3 blood sample FACS analysis.

Figure 31:
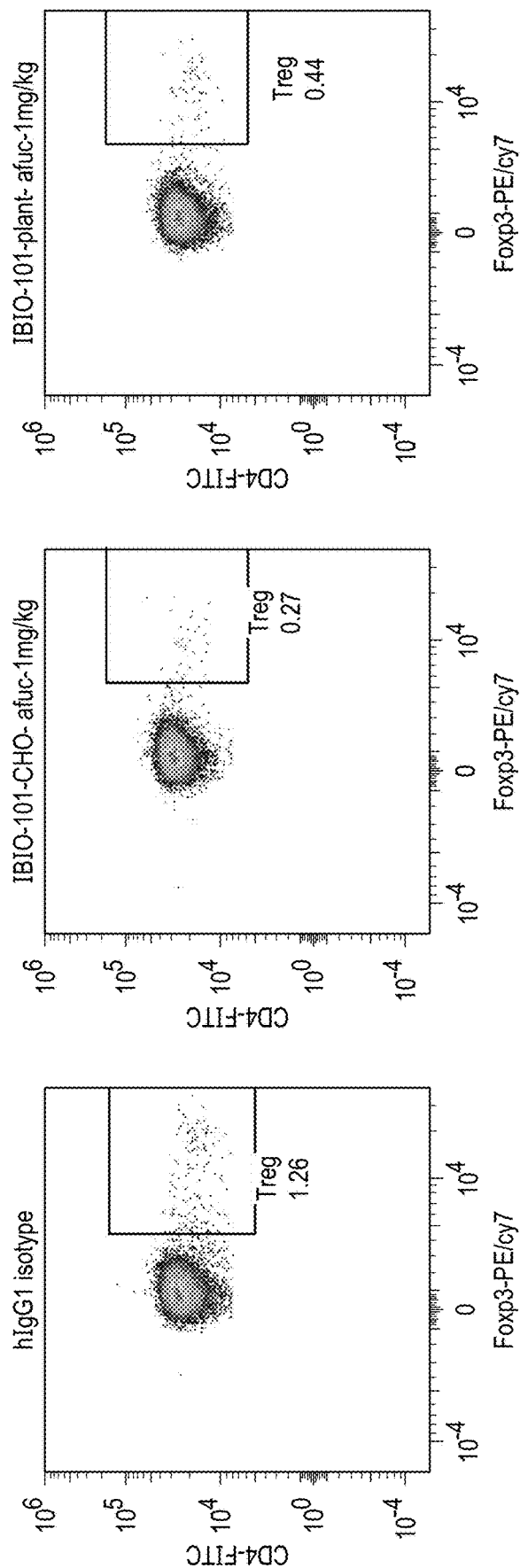
FIG. 31 shows Day 3 post dosed blood sample from Efficacy Study FACS analysis of representative FACS plots showing the $T_{reg}$ percentage in blood after treatment with hIgG1 isotype, IBIO-101-CHO-afuc and IBIO-101-plant-afuc.
Figure 32A:
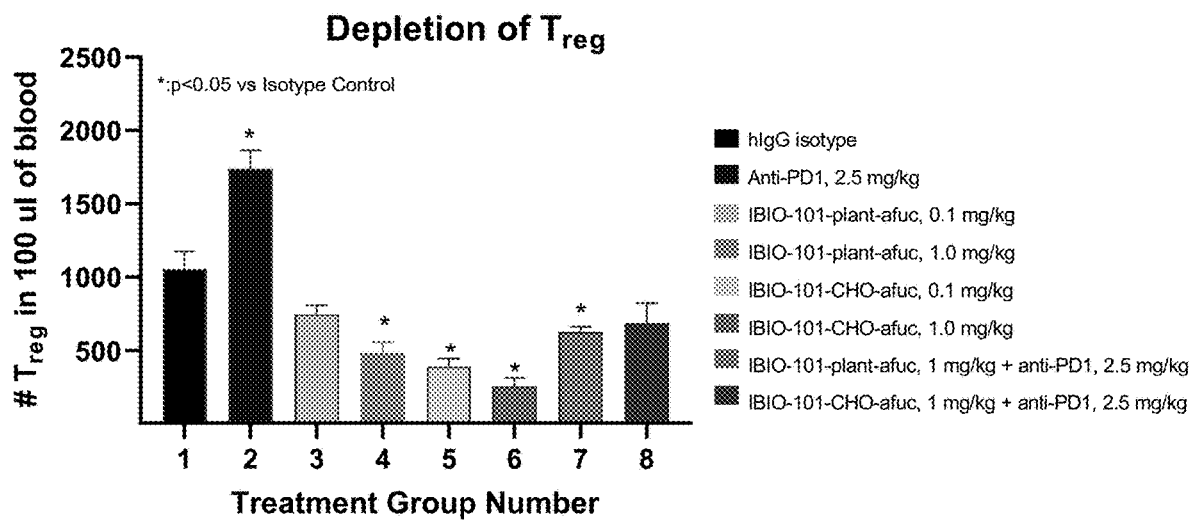
FIGS. 32A to 32E show that IBIO-101 molecules reduce $T_{reg}$ cells in blood at 3 days post-treatment of Efficacy study.
Figure 32B:
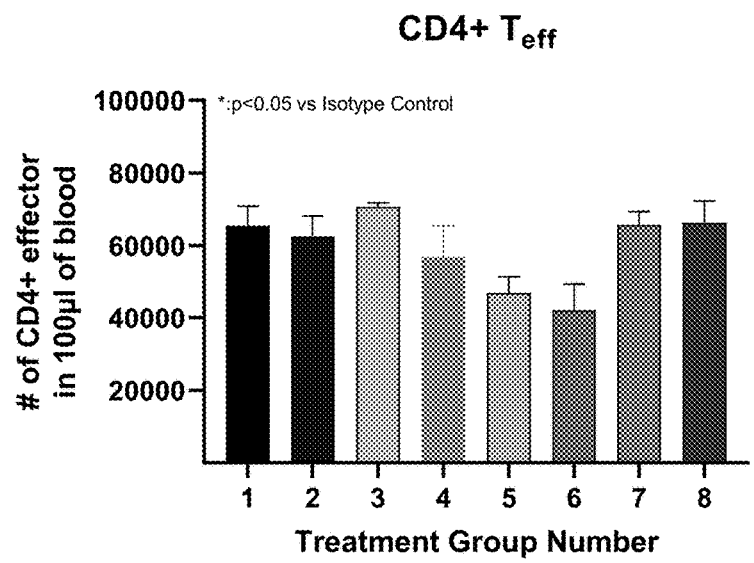
Figure 32C:
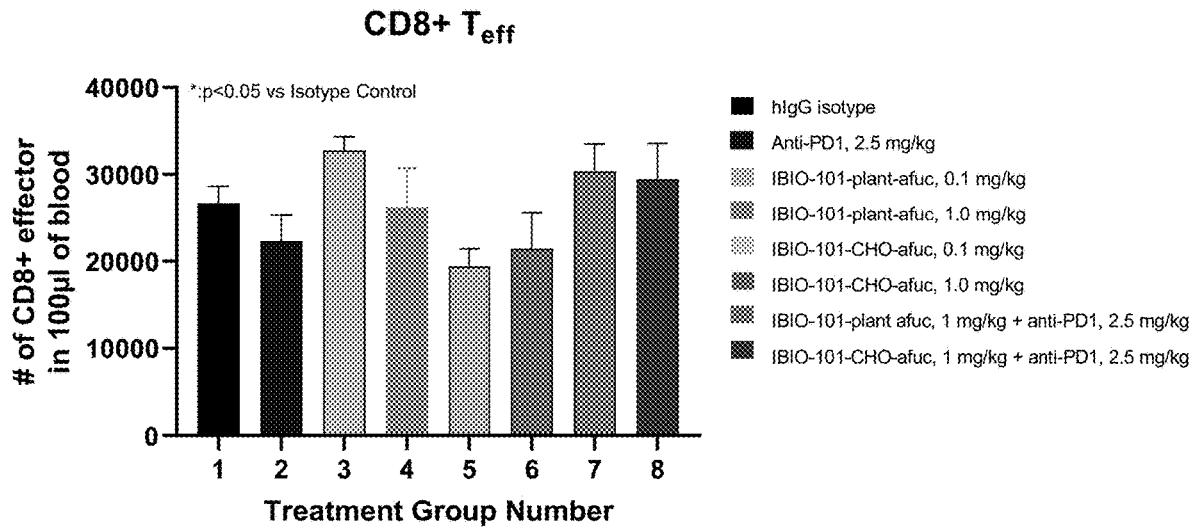
Figure 32D:
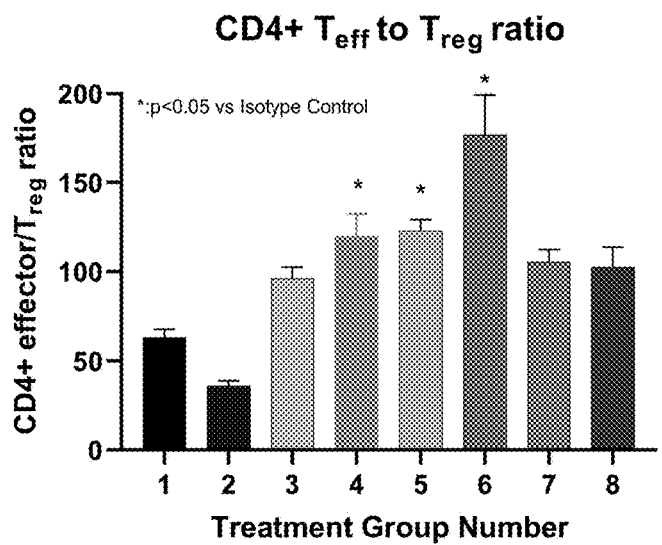
Figure 32E:
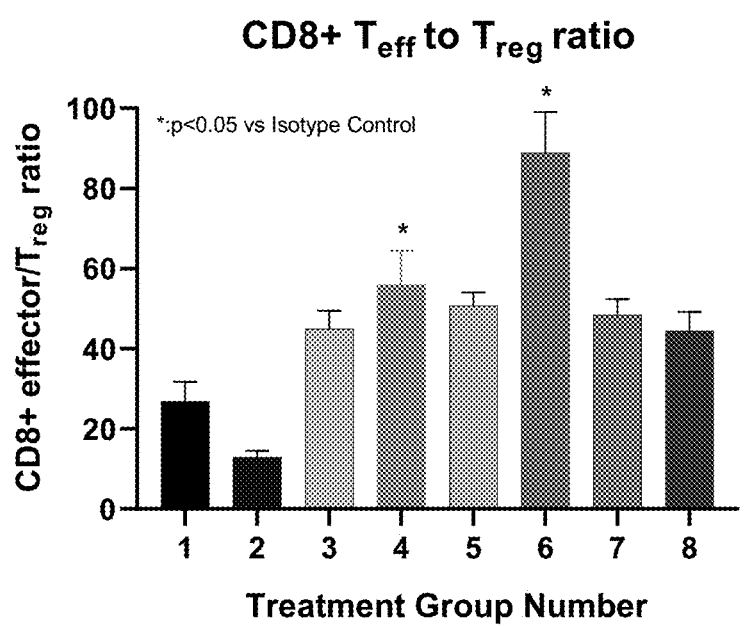

FIG. 31 shows Day 3 blood sample FACS analysis of representative FACS plots showing the T$_{reg}$ percentage in blood after treatment with hIgG1 isotype, IBIO-101-CHO-afuc and IBIO-101-plant-afuc.

FIG. 32 is a graph that shows Day 3, planta or CHO depleted T$_{reg}$ compared to that of isotype control.

FIGS. 32A to 32E show that IBIO-101 molecules reduce T$_{reg}$ cells in blood at 3 days post-treatment. FACS analysis showing dose-dependent, cytotoxic effect of afucosylated IBIO-101 molecules made in CHO and plants as compared with anti-PD1 only or human isotype control on circulating T$_{reg}$ (FIG. 33A), CD4+ effector cells (FIG. 33B), and CD8+ effector cells in blood (FIG. 33C). Ratio between CD4+ effector/T$_{reg}$ and CD8+ effector/T$_{reg}$ cells are shown in FIGS. 33D and 33E, respectively. Values plotted are average cell number±SEM (n=4/group). Row 1—hIgG1 isotype control; Row 2 Anti-PD1, 2.5 mg/kg; Row 3—IBIO-101-plant-afuc, 0.1 mg/kg; Row 4—IBIO-101-plant-afuc, 1.0 mg/kg; Row 5—-IBIO-101-CHO-afuc, 0.1 mg/kg; Row 6—IBIO-101-CHO-afuc, 1.0 mg/kg; Row 7—IBIO-101-plant-afuc, 1.0 mg/kg+Anti-PD1, 2.5 mg/kg; Row 8—IBIO-101-CHO-afuc, 1.0 mg/kg+Anti-PD1, 2.5 mg/kg.

Using Artificial Intelligent injunction with epitope-selective antibody discovery platform, IBIO-101, a novel CD25 mAb was designed. Glyco-Engineered transgenic N. benthamiana plant line (AXT/FT) was implemented to produce plant-based IBIO-101. Plant-based IBIO-101 is comparable to CHO made IBIO-101 in kinetic affinity and selectively binding to human and cynos monkey but not mouse CD25. Both Plant and CHO made IBIO-101 have high affinity to SUDHL1, a CD25 high expression cancer cell line and human iTreg cells while evading IL-2 blocking signaling pathway. Glyco-Engineered afucosylated IBIO-101 enhanced ADCC activity and cancer cell killing via human PBMC while also depleting human Treg. Both Plant and CHO made IBIO-101 demonstrated dose dependent in reducing MC38 (colon cancer) tumor in hTg CD25 mice by depleting Treg cells while preserving Teff cells. IBIO-101 showed an additive effect in tumor reducing with anti-PD1 antibody combination therapy in MC38 TgCD25 mouse xenograft model. The equivalency of potency between plant and CHO made IBIO-101 demonstrates that both CHO and plant-based biologic are suitable and viable options for human cancer therapy.

As embodied and broadly described herein, an aspect of the present disclosure relates to a humanized antibody or binding fragments that binds human CD25, wherein the antibody or binding fragment thereof comprises, consists essentially of or consists of: a variable heavy chain amino acid sequence of SEQ ID NO:1 or 9, or a sequence comprising at least 70% sequence identity thereto; and a variable light chain amino acid sequence of SEQ ID NO: 4 or 11, or a sequence comprising at least 70% sequence identity thereto. In one aspect, the antibody or binding fragments comprises a variable heavy chain amino acid sequence of SEQ ID NO: 1 or 9, or a sequence comprising at least 75, 80, 85, 90, 91, 92, 93, 94, 95, 96, 97, 98, 99, or 100% sequence identity to SEQ ID NO:1 or 9. In another aspect, the antibody or binding fragment comprises a variable light chain amino acid sequence of SEQ ID NO: 4 or 11, or a sequence comprising at least 75, 80, 85, 90, 91, 92, 93, 94, 95, 96, 97, 98, 99, or 100% sequence identity to SEQ ID NO: 4 or 11. In another aspect, a nucleic acid that encodes SEQ ID NO: 1 or 9, has at least 75, 80, 85, 90, 91, 92, 93, 94, 95, 96, 97, 98, 99, or 100% sequence identity to the nucleic acid sequence as set forth in SEQ ID NO: 2, 3, or 10, respectively. In another aspect, a nucleic acid that encodes SEQ ID NO: 4 or 11, has at least 75, 80, 85, 90, 91, 92, 93, 94, 95, 96, 97, 98, 99, or 100% sequence identity to the nucleic acid sequence as set forth in SEQ ID NO: 5, 6, or 12, respectively. In another aspect, the nucleic acid that encodes SEQ ID NO: 4 or 9 are sequence optimized for expression in plants. In another aspect, the antibody further comprises one or more mutations to the framework region. In another aspect, the antibody binds human CD25 and cynomologous monkey CD25, but not mouse or rat CD25. In another aspect, an EC50 ratio of binding to human CD25 and cynomologous monkey CD25 is from about 0.75 to about 1.25. In another aspect, the antibody is afucosylated. In another aspect, the antibody is afucosylated in cellulo in a CHO cell or a plant cell. In another aspect, the antibody or binding fragment increases effector T cell function when contacted with the antibody or binding fragment.

In another embodiment, the present invention is a pharmaceutical composition that comprises, consists essentially of, or consists of: any one of the humanized CD25 antibodies or fragments thereof described hereinabove.

In another embodiment, the present invention is an isolated nucleic acid sequence encoding any one of the humanized CD25 antibodies described hereinabove.

In another embodiment, the present invention is an expression vector comprising the isolated nucleic acid described hereinabove.

In another embodiment, the present invention is a vector comprising the nucleic acid sequence described hereinabove.

In another embodiment, the present invention is a method of treating a subject in need thereof that comprises, consists essentially of, or consists of: administering to the subject a therapeutically effective amount of any one of the humanized CD25 antibodies or the pharmaceutical composition described hereinabove.

In another embodiment, the present invention is a method of depleting the number of regulatory T cells in a subject that comprises, consists essentially of, or consists of: administering to the subject a therapeutically effective amount of any one of the humanized CD25 antibodies or the pharmaceutical composition described hereinabove. In one aspect, the subject suffers from cancer. In another aspect, the subject suffers from an autoimmune-related disease or disorder. In another aspect, the subject is provided a co-therapy.

In another embodiment, the present invention is a method of depleting the number of regulatory T cells in a sample that comprises, consists essentially of, or consists of: peripheral blood mononuclear cells comprising contacting the sample with any one of the humanized CD25 antibodies described hereinabove.

In another embodiment, the present invention is a kit that comprises, consists essentially of, or consists of: any one of the antibodies or the pharmaceutical composition described hereinabove.

In another embodiment, the present invention is an *Agrobacterium tumefaciens* cell that comprises, consists essentially of, or consists of the expression vector described hereinabove.

In another embodiment, the present invention is a method for making an antibody having anti-cancer activity, the method that comprises, consists essentially of, or consists of (a) introducing into a plant a plant viral vector that includes a polynucleotide encoding the polypeptide of SEQ ID NO:1 and 2 having anticancer activity, or a sequence comprising at least 75, 80, 85, 90, 91, 92, 93, 94, 95, 96, 97, 98, 99, or 100% sequence identity to; and (b) maintaining the plant under conditions and for a time sufficient that the antibody is expressed in at least some plant cells. In another aspect, the introducing comprises vacuum infiltration. In another aspect, the plant comprises the antibody having anti-cancer activity. In another aspect, the antibody having anti-cancer activity from the plant. In another aspect, the antibody has anti-cancer activity.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

Additionally, the section headings herein are provided for consistency with the suggestions under 37 CFR 1.77 or otherwise to provide organizational cues. These headings shall not limit or characterize the invention(s) set out in any claims that may issue from this disclosure. Specifically and by way of example, although the headings refer to a "Field of Invention," such claims should not be limited by the language under this heading to describe the so-called technical field. Further, a description of technology in the "Background of the Invention" section is not to be construed as an admission that technology is prior art to any invention(s) in this disclosure. Neither is the "Summary" to be considered a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings set forth herein.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

To aid the Patent Office, and any readers of any patent issued on this application in interpreting the claims appended hereto, applicants wish to note that they do not intend any of the appended claims to invoke paragraph 6 of 35 U.S.C. § 112, U.S.C. § 112 paragraph (f), or equivalent, as it exists on the date of filing hereof unless the words "means for" or "step for" are explicitly used in the particular claim.

For each of the claims, each dependent claim can depend both from the independent claim and from each of the prior dependent claims for each and every claim so long as the prior claim provides a proper antecedent basis for a claim term or element.

What is claimed is:

1. A humanized anti-CD25 or binding fragment thereof that binds human CD25, which comprises:
   a variable heavy chain comprising an amino acid sequence that is at least 95% identical to SEQ ID NO: 1 or 9 and comprises complementarity determining regions (CDRs) identical to the CDRs in the amino acid sequence of SEQ ID NO: 1 or 9; and
   a variable light chain comprising an amino acid sequence that is at least 95% identical to SEQ ID NO: 4 or 11 and comprises complementarity determining regions (CDRs) identical to the CDRs in the amino acid sequence of SEQ ID NO: 4 or 11.

2. The humanized anti-CD25 antibody of claim 1, wherein the antibody or binding fragments comprises a variable heavy chain amino acid sequence of SEQ ID NO: 1 or 9, or a sequence comprising at least 96, 97, 98, 99, or 100% sequence identity to SEQ ID NO:1 or 9.

3. The humanized anti-CD25 antibody of claim 1, wherein the antibody or binding fragment comprises a variable light chain amino acid sequence of SEQ ID NO: 4 or 11, or a sequence comprising at least 96, 97, 98, 99, or 100% sequence identity to SEQ ID NO: 4 or 11.

4. The humanized anti-CD25 antibody of claim 1, wherein a nucleic acid that encodes SEQ ID NO: 1 or 9, has at least 96, 97, 98, 99, or 100% sequence identity to the nucleic acid sequence as set forth in SEQ ID NO: 2, 3, or 10, respectively.

5. The humanized anti-CD25 antibody of claim 1, wherein a nucleic acid that encodes SEQ ID NO: 4 or 11, has at least 95, 96, 97, 98, 99, or 100% sequence identity to the nucleic acid sequence as set forth in SEQ ID NO: 5, 6, or 12, respectively.

6. The humanized CD25 antibody of claim 1, wherein the nucleic acid that encodes SEQ ID NO: 4 or 9 are sequence optimized for expression in plants.

7. The humanized CD25 of claim 1, wherein the antibody or binding fragment further comprises one or more mutations to the framework region.

8. The humanized anti-CD25 of claim 1, wherein the antibody or binding fragment binds human CD25 and cynomolgus monkey CD25, but not mouse or rat CD25.

9. The humanized anti-CD25 of claim 1, wherein an EC50 ratio of binding to human CD25 and cynomolgus monkey CD25 is from about 0.75 to about 1.25.

10. The humanized anti-CD25 antibody of claim 1, wherein the antibody or binding fragment is afucosylated.

11. The humanized anti-CD25 antibody of claim 1, wherein the antibody or binding fragment is afucosylated in cellulo in a CHO cell or a plant cell.

12. The humanized anti-CD25 antibody of claim 1, wherein the antibody or binding fragment increases effector T cell function when contacted with the antibody or binding fragment.

13. A pharmaceutical composition comprising any one of the humanized anti-CD25 antibodies or binding fragments of claim 1.

14. An isolated nucleic acid sequence encoding any one of the humanized anti-CD25 antibodies or binding fragments of claim 1.

15. An expression vector comprising the isolated nucleic acid of claim 14.

16. A vector comprising the isolated nucleic acid sequence of claim 14.

17. A method of depleting regulatory T cells in a subject comprising administering to the subject a therapeutically effective amount of the humanized anti-CD25 antibody or binding fragments of claim 1.

18. The method of claim 17, wherein the subject suffers from cancer.

19. The method of claim 17, wherein the subject suffers from an autoimmune-related disease or disorder.

20. The method of claim 17, wherein the humanized anti-CD25 is provided as a co-therapy.

21. A method of depleting regulatory T cells in a sample comprising peripheral blood mononuclear cells comprising contacting the sample with any one of the humanized anti-CD25 antibodies or binding fragments of claim 1.

22. An *Agrobacterium tumefaciens* cell comprising the expression vector of claim 16.

* * * * *